(12) United States Patent
Volker et al.

(10) Patent No.: US 7,668,661 B2
(45) Date of Patent: *Feb. 23, 2010

(54) LIVER DISEASE-RELATED METHODS AND SYSTEMS

(75) Inventors: Michael Volker, Cologne (DE); Michael Becka, Ense (DE); Werner Kroll, Stamford, CT (US); Andreas Knorr, Erkrath (DE); Sylvia Unger, Heidelberg (DE); Mathias Gehrmann, Leverkusen (DE); Guido Hennig, Krefeld (DE); Elmar-Reinhold Burchardt, Schwerte (DE); Michael J. Arthur, West Wellow (GB); Alastair D. Burt, Fairmoor Morphet (GB); Massimo Pinzani, Scandicci (IT); Detlef Schuppan, Bubenreuth (DE); Robert P. Thiel, Oxford, CT (US); Christoph Petry, Leverkusen (DE); William Rosenberg, Eastleigh (GB)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 470 days.

This patent is subject to a terminal disclaimer.

(21) Appl. No.: 10/868,437

(22) Filed: Jun. 15, 2004

(65) Prior Publication Data

US 2007/0172907 A1 Jul. 26, 2007

Related U.S. Application Data

(63) Continuation-in-part of application No. 10/258,689, filed on Oct. 7, 2003, now Pat. No. 7,141,380.

(30) Foreign Application Priority Data

Apr. 26, 2001 (EP) ...................... PCT/EP01/04696

(51) Int. Cl.
G06F 7/00 (2006.01)

(52) U.S. Cl. .......................... 702/19; 702/20; 707/102; 703/11; 435/7.1

(58) Field of Classification Search .................... None
See application file for complete search history.

(56) References Cited

U.S. PATENT DOCUMENTS

| | | | |
|---|---|---|---|
| 5,019,498 A | 5/1991 | Chichibu | |
| 5,316,914 A | 5/1994 | Oshima et al. | |
| 6,000,828 A | 12/1999 | Leet | |
| 7,225,080 B2 * | 5/2007 | Poynard | 702/19 |
| 2004/0053242 A1 | 3/2004 | Volker et al. | |

FOREIGN PATENT DOCUMENTS

| | | |
|---|---|---|
| EP | 1150123 | 12/2006 |
| EP | 1283989 | 7/2007 |
| WO | WO 01/86304 | 11/2001 |
| WO | WO0186304 | 11/2001 |

OTHER PUBLICATIONS

Pilette et al. Histopathological evaluation of Liver Fibrosis: quantitive image analysis vs simi-quantitative scores 1998. vol. 28, pp. 439-446.
International Search Report PCT/US05/21002-Filed: Jun. 15, 2005.
Alexandrakis et al., "Use of a Variety of Biological Parameters in Distinguishing Cirrhotic From Malignant Ascites," Int. J. Biol. Markers, 16:45-49, 2001.
H. Franklin Bunn & Wendell Rosse, "Hemolytic Anemias and Acute Blood Loss," in *Harrison's Principles of Internal Medicine*, 681, 681 (Eugene Braunwald, Stephen L. Hauser, Anthony S. Fauchi, Dan L. Longo, Dennis L. Kasper & J. Larry Jameson eds., McGraw-Hill 15th ed. 2001.
Daniluk et al., "Serum Cytokine Levels in Alcohol-Related Liver Cirrhosis," Alcohol, 23:29-34, 2001.
Henry N. Ginsberg & Ira J. Goldberg, *Disorders of Lipoprotein Metabolism, in Harrison's Principles of Internal Medicine*, 2245, 2246-2247 (Eugene Braunwald, Stephen L. Hauser, Anthony S. Fauchi, Dan L. Longo, Dennis L. Kasper & J. Larry Jameson eds., McGraw-Hill 15th ed 2001.
Jensen et al., "Collagen: Scaffold for Repair or Execution," Cardiovasc. Res. 33:535-539, 1997.
Kerrigan et al., "Matrix Turnover," J. Orthod., 27:227-233, 2000.
Daniel S. Pratt & Marshall M. Kaplan, *Evaluation of Liver Function, in Harrison's Principles of Internal Medicine*, 1714, 1711-1714 (Eugene Braunwald, Stephen L. Hauser, Anthony S. Fauchi, Dan L. Longo, Dennis L. Kasper & J. Larry Jameson eds., McGraw-Hill 15th ed. 2001).
Peter J. Quesenberry & Gerald A Colvin, *Hematopoiesis, in Harrison's Principles of Internal Medicine*, 653, 655-657 (Eugene Braunwald, Stephen L. Hauser, Anthony S. Fauchi, Dan L. Longo, Dennis L. Kasper & J. Larry Jameson eds., McGraw-Hill 15th ed 2001.
S. Ramakrishnan et al., *Textbook of Medical Biochemistry*, 155-158 (Orient BlackSwan 3rd ed. 2004).
Rochling, "Evaluation of Abnormal Liver Tests," Clin. Cornerstone, 3(6):1-12, 2001.
Shah et al., "Apolipoprotein Deficiency and Chronic Liver Disease," J. Assoc. Physicians India, 49:274-278, 2001.
Poon T C-W et al: "Application of Classification Tree and Neural Network Algorithms to the Identification of Serological Liver Marker Profiles for the Diagnosis of Hepatocellular Carcinoma" Oncology, S. Karger, Basel, CH, vol. 61, No. 4, 1 Nov. 001, pp. 275- 283, XP009044316 ISSN: 0030-2414 2001.

(Continued)

*Primary Examiner*—Mary K Zeman
(74) *Attorney, Agent, or Firm*—Kevin Stein, Esq.

(57) ABSTRACT

The invention provides diagnostic methods, kits, and systems, and related computer-readable media, which use multiple blood marker values, including serum and plasma marker values, to aid in the diagnosis of the status or progress of a liver disease in a patient.

The invention also provides methods and systems, and related computer-readable media, that use blood marker values, including serum and plasma marker values: (1) to screen for active ingredients useful in the treatment of a liver disease; (2) to aid in the selection of treatment regimens for patients that are predisposed to, or suffer from, liver disease; and (3) to aid in the design of clinical programs useful in monitoring the status or progress of liver disease in one or more patients.

19 Claims, 11 Drawing Sheets

OTHER PUBLICATIONS

Fortunato G et al: "Multivariate Discriminant Function Based on Six Biochemical Markers in Blood Can Predict the Cirrhotic Evolution of Chronic Hepatitis" Clinical Chemistry, American Association for Clinical Chemistry, Washington, DC, vol. 47, No. 9, 1. Sep. 2001, pp. 1696-1700, XP002996105 ISSN: 0009-9147 "abstract" 2001.

Duda R et al: "Pattern Classification - Chapter 1" 2001, John Wiley & Sons, New York, US, XP002536377, pp. 14-17 2001.

Sylvie Naveau et al: "Alpha -2- Macroglobulin and Hepatic Fibrosis - Diagnostic Interest", Digestive Diseases and Sciences, vol. 39, No. 11, Nov. 1994.

Giuseppe Castaldo: "Differential diagnosis between heptocellular carcinoma and cirrhosis through a discriminant function based on results for serum analytes", Clinical Chemistry, vol. 42, No. 8, 1996.

D. Schuppan et al: "Serummarker der Leberfibrose", Deutsche medizinische Wochenzeitschrift, Nr. 124, 1999.

Ji Xuhuai et al: "Clinical significance of serum 7S collagen and type VI collagen levels for the diagnosis of hepatic fibrosis", Chinese Medical Journal 1997, 110(3), 1997.

J P Teare et al: "Comparison of serum procollagen III peptide concentrations and PGA index for assessment of hepatic fibrosis", The Lancet, vol. 342, 1993.

J. Guechot et al: "Diagnostic accuracy of hyaluronan and type III procollagen amino-terminal peptide serum assays as markers of liver fibrosis in chronic viral hepatitis C evaluated by ROC curve analysis", Clinical Chemistry, vol. 42, No. 4, 1996.

Enrico Rossi et al: "Validation of the Fibro TEst Biochemical Markers Score in Assessing Liver Fibrosis in Hepatitis C Patients" Clinical Chemistry vol. 49, No. 3, 2003.

Christophe Pilette et al: "Histopathological evaluation of liver fibrosis: quantitative image analysis vs smiquantitative scores - Comparison with serum markers", Journal of Hepatology, 1998, vol. 28.

* cited by examiner

Receiver Operator Characteristic Curve

Scheuer Modified Scoring System

Validation Data

Receiver Operator Characteristic Curve

Ishak Modified Scoring System

Validation Data

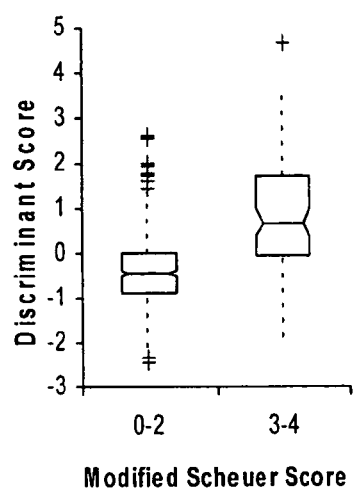
Figure 4: Box and Whisker Plot for the Validation Data Set (Gv) showing Scheuer Fibrosis Score v. Discriminant Score

FIGURE 5 (SEQ ID NO: 1)

ref|NM_003254.1| Homo sapiens tissue inhibitor of metalloproteinase 1 (erythroid potentiating activity, collagenase inhibitor) (TIMP1), mRNA AGGGGCCTTAGCGTGCCGCATCGCCGAGATCCAGCGCCCAGAGAGACACCAGA
GAACCCACCATGGCCCCCTTTGAGCCCCTGGCTTCTGGCATCCTGTTGTTGCTGT
GGCTGATAGCCCCCAGCAGGGCCTGCACCTGTGTCCCACCCCACCCACAGACGG
CCTTCTGCAATTCCGACCTCGTCATCAGGGCCAAGTTCGTGGGGACACCAGAAG
TCAACCAGACCACCTTATACCAGCGTTATGAGATCAAGATGACCAAGATGTATA
AAGGGTTCCAAGCCTTAGGGGATGCCGCTGACATCCGGTTCGTCTACACCCCCG
CCATGGAGAGTGTCTGCGGATACTTCCACAGGTCCCACAACCGCAGCGAGGAG
TTTCTCATTGCTGGAAAACTGCAGGATGGACTCTTGCACATCACTACCTGCAGT
TTCGTGGCTCCCTGGAACAGCCTGAGCTTAGCTCAGCGCCGGGGCTTCACCAAG
ACCTACACTGTTGGCTGTGAGGAATGCACAGTGTTTCCCTGTTTATCCATCCCCT
GCAAACTGCAGAGTGGCACTCATTGCTTGTGGACGGACCAGCTCCTCCAAGGCT
CTGAAAAGGGCTTCCAGTCCCGTCACCTTGCCTGCCTGCCTCGGGAGCCAGGGC
TGTGCACCTGGCAGTCCCTGCGGTCCCAGATAGCCTGAATCCTGCCCGGAGTGG
AACTGAAGCCTGCACAGTGTCCACCCTGTTCCCACTCCCATCTTTCTTCCGGACA
ATGAAATAAAGAG TTACCACCCAGC

FIGURE 6 (Page 1 of 2)(SEQ ID NO: 2)

ref|NM_004530.1| Homo sapiens matrix metalloproteinase 2 (gelatinase A, 72kDa gelatinase, 72kDa type IV collagenase) (MMP2), mRNA

```
TGTTTCCGCTGCATCCAGACTTCCTCAGGCGGTGGCTGGAGGCTGCGCATCTGG
GGCTTTAAACATACAAAGGGATTGCCAGGACCTGCGGCGGCGGCGGCGGCGGC
GGGGGCTGGGGCGCGGGGGCCGGACCATGAGCCGCTGAGCCGGGCAAACCCCA
GGCCACCGAGCCAGCGGACCCTCGGAGCGCAGCCCTGCGCCGCGGACCAGGCT
CCAACCAGGCGGCGAGGCGGCCACACGCACCGAGCCAGCGACCCCCGGGCGAC
GCGCGGGGCCAGGGAGCGCTACGATGGAGGCGCTAATGGCCCGGGGCGCGCTC
ACGGGTCCCCTGAGGGCGCTCTGTCTCCTGGGCTGCCTGCTGAGCCACGCCGCC
GCCGCGCCGTCGCCCATCATCAAGTTCCCCGGCGATGTCGCCCCAAAACGGAC
AAAGAGTTGGCAGTGCAATACCTGAACACCTTCTATGGCTGCCCCAAGGAGAG
CTGCAACCTGTTTGTGCTGAAGGACACACTAAAGAAGATGCAGAAGTTCTTTGG
ACTGCCCCAGACAGGTGATCTTGACCAGAATACCATCGAGACCATGCGGAAGC
CACGCTGCGGCAACCCAGATGTGGCCAACTACAACTTCTTCCCTCGCAAGCCCA
AGTGGGACAAGAACCAGATCACATACAGGATCATTGGCTACACACCTGATCTG
GACCCAGAGACAGTGGATGATGCCTTTGCTCGTGCCTTCCAAGTCTGGAGCGAT
GTGACCCCACTGCGGTTTTCTCGAATCCATGATGGAGAGGCAGACATCATGATC
AACTTTGGCCGCTGGGAGCATGGCGATGGATACCCCTTTGACGGTAAGGACGG
ACTCCTGGCTCATGCCTTCGCCCCAGGCACTGGTGTTGGGGGAGACTCCCATTT
TGATGACGATGAGCTATGGACCTTGGGAGAAGGCCAAGTGGTCCGTGTGAAGT
ATGGCAACGCCGATGGGGAGTACTGCAAGTTCCCCTTCTTGTTCAATGGCAAGG
AGTACAACAGCTGCACTGATACTGGCCGCAGCGATGGCTTCCTCTGGTGCTCCA
CCACCTACAACTTTGAGAAGGATGGCAAGTACGGCTTCTGTCCCCATGAAGCCC
TGTTCACCATGGGCGGCAACGCTGAAGGACAGCCCTGCAAGTTTCCATTCCGCT
TCCAGGGCACATCCTATGACAGCTGCACCACTGAGGGCCGCACGGATGGCTAC
CGCTGGTGCGGCACCACTGAGGACTACGACCGCGACAAGAAGTATGGCTTCTG
CCCTGAGACCGCCATGTCCACTGTTGGTGGGAACTCAGAAGGTGCCCCCTGTGT
CTTCCCCTTCACTTTCCTGGGCAACAAATATGAGAGCTGCACCAGCGCCGGCCG
CAGTGACGGAAAGATGTGGTGTGCGACCACAGCCAACTACGATGACGACCGCA
AGTGGGGCTTCTGCCCTGACCAAGGGTACAGCCTGTTCCTCGTGGCAGCCCACG
AGTTTGGCCACGCCATGGGGCTGGAGCACTCCCAAGACCCTGGGGCCCTGATG
GCACCCATTTACACCTACACCAAGAACTTCCGTCTGTCCCAGGATGACATCAAG
GGCATTCAGGAGCTCTATGGGGCCTCTCCTGACATTGACCTTGGCACCGGCCCC
ACCCCCACACTGGGCCCTGTCACTCCTGAGATCTGCAAACAGGACATTGTATTT
GATGGCATCGCTCAGATCCGTGGTGAGATCTTCTTCTTCAAGGACCGGTTCATTT
```

FIGURE 6 (Page 2 of 2)(SEQ ID NO: 2)(cont.)

ref|NM_004530.1| Homo sapiens matrix metalloproteinase 2 (gelatinase A, 72kDa gelatinase, 72kDa type IV collagenase) (MMP2), mRNA (cont.)

GGCGGACTGTGACGCCACGTGACAAGCCCATGGGGCCCCTGCTGGTGGCCACA
TTCTGGCCTGAGCTCCCGGAAAAGATTGATGCGGTATACGAGGCCCCACAGGA
GGAGAAGGCTGTGTTCTTTGCAGGGAATGAATACTGGATCTACTCAGCCAGCAC
CCTGGAGCGAGGGTACCCCAAGCCACTGACCAGCCTGGGACTGCCCCCTGATGT
CCAGCGAGTGGATGCCGCCTTTAACTGGAGCAAAAACAAGAAGACATACATCT
TTGCTGGAGACAAATTCTGGAGATACAATGAGGTGAAGAAGAAAATGGATCCT
GGCTTTCCCAAGCTCATCGCAGATGCCTGGAATGCCATCCCCGATAACCTGGAT
GCCGTCGTGGACCTGCAGGGCGGCGGTCACAGCTACTTCTTCAAGGGTGCCTAT
TACCTGAAGCTGGAGAACCAAAGTCTGAAGAGCGTGAAGTTTGGAAGCATCAA
ATCCGACTGGCTAGGCTGCTGAGCTGGCCCTGGCTCCCACAGGCCCTTCCTCTC
CACTGCCTTCGATACACCGGGCCTGGAGAACTAGAGAAGGACCCGGAGGGGCC
TGGCAGCCGTGCCTTCAGCTCTACAGCTAATCAGCATTCTCACTCCTACCTGGTA
ATTTAAGATTCCAGAGAGTGGCTCCTCCCGGTGCCCAAGAATAGATGCTGACTG
TACTCCTCCCAGGCGCCCCTTCCCCCTCCAATCCCACCAACCCTCAGAGCCACC
CCTAAAGAGATCCTTTGATATTTTCAACGCAGCCCTGCTTTGGGCTGCCCTGGTG
CTGCCACACTTCAGGCTCTTCTCCTTTCACAACCTTCTGTGGCTCACAGAACCCT
TGGAGCCAATGGAGACTGTCTCAAGAGGGCACTGGTGGCCCGACAGCCTGGCA
CAGGGCAGTGGGACAGGGCATGGCCAGGTGGCCACTCCAGACCCCTGGCTTTT
CACTGCTGGCTGCCTTAGAACCTTTCTTACATTAGCAGTTTGCTTTGTATGCACT
TTGTTTTTTTCTTTGGGTCTTGTTTTTTTTTCCACTTAGAAATTGCATTTCCTGAC
AGAAGGACTCAGGTTGTCTGAAGTCACTGCACAGTGCATCTCAGCCCACATAGT
GATGGTTCCCCTGTTCACTCTACTTAGCATGTCCCTACCGAGTCTCTTCTCCACT
GGATGGAGGAAAACCAAGCCGTGGCTTCCCGCTCAGCCCTCCCTGCCCCTCCC
TTCAACCATTCCCCATGGGAAATGTCAACAAGTATGAATAAAGACACCTACTGA
GTGGC

FIGURE 7 (Page 1 of 2)(SEQ ID NO: 3)

ref|NM_004994.1| Homo sapiens matrix metalloproteinase 9 (gelatinase B, 92kDa gelatinase, 92kDa type IV collagenase) (MMP9), mRNA

```
AGACACCTCTGCCCTCACCATGAGCCTCTGGCAGCCCCTGGTCCTGGTGCTCCT
GGTGCTGGGCTGCTGCTTTGCTGCCCCAGACAGCGCCAGTCCACCCTTGTGCT
CTTCCCTGGAGACCTGAGAACCAATCTCACCGACAGGCAGCTGGCAGAGGAAT
ACCTGTACCGCTATGGTTACACTCGGGTGGCAGAGATGCGTGGAGAGTCGAAA
TCTCTGGGGCCTGCGCTGCTGCTTCTCCAGAAGCAACTGTCCCTGCCCGAGACC
GGTGAGCTGGATAGCGCCACGCTGAAGGCCATGCGAACCCCACGGTGCGGGGT
CCCAGACCTGGGCAGATTCCAAACCTTTGAGGGCGACCTCAAGTGGCACCACC
ACAACATCACCTATTGGATCCAAAACTACTCGGAAGACTTGCCGCGGGCGGTG
ATTGACGACGCCTTTGCCCGCGCCTTCGCACTGTGGAGCGCGGTGACGCCGCTC
ACCTTCACTCGCGTGTACAGCCGGGACGCAGACATCGTCATCCAGTTTGGTGTC
GCGGAGCACGGAGACGGGTATCCCTTCGACGGGAAGGACGGGCTCCTGGCACA
CGCCTTTCCTCCTGGCCCCGGCATTCAGGGAGACGCCCATTTCGACGATGACGA
GTTGTGGTCCCTGGGCAAGGGCGTCGTGGTTCCAACTCGGTTTGGAAACGCAGA
TGGCGCGGCCTGCCACTTCCCCTTCATCTTCGAGGGCCGCTCCTACTCTGCCTGC
ACCACCGACGGTCGCTCCGACGGCTTGCCCTGGTGCAGTACCACGGCCAACTAC
GACACCGACGACCGGTTTGGCTTCTGCCCCAGCGAGAGACTCTACACCCGGGAC
GGCAATGCTGATGGGAAACCCTGCCAGTTTCCATTCATCTTCCAAGGCCAATCC
TACTCCGCCTGCACCACGGACGGTCGCTCCGACGGCTACCGCTGGTGCGCCACC
ACCGCCAACTACGACCGGGACAAGCTCTTCGGCTTCTGCCCGACCCGAGCTGAC
TCGACGGTGATGGGGGGCAACTCGGCGGGGGAGCTGTGCGTCTTCCCCTTCACT
TTCCTGGGTAAGGAGTACTCGACCTGTACCAGCGAGGGCCGCGGAGATGGGCG
CCTCTGGTGCGCTACCACCTCGAACTTTGACAGCGACAAGAAGTGGGGCTTCTG
CCCGGACCAAGGATACAGTTTGTTCCTCGTGGCGGCGCATGAGTTCGGCCACGC
GCTGGGCTTAGATCATTCCTCAGTGCCGGAGGCGCTCATGTACCCTATGTACCG
CTTCACTGAGGGGCCCCCCTTGCATAAGGACGACGTGAATGGCATCCGGCACCT
CTATGGTCCTCGCCCTGAACCTGAGCCACGGCCTCCAACCACCACCACACCGCA
GCCCACGGCTCCCCCGACGGTCTGCCCCACCGGACCCCCCACTGTCCACCCCTC
AGAGCGCCCCACAGCTGGCCCCACAGGTCCCCCCTCAGCTGGCCCCACAGGTCC
CCCCACTGCTGGCCCTTCTACGGCCACTACTGTGCCTTTGAGTCCGGTGGACGA
TGCCTGCAACGTGAACATCTTCGACGCCATCGCGGAGATTGGGAACCAGCTGTA
TTTGTTCAAGGATGGGAAGTACTGGCGATTCTCTGAGGGCAGGGGGAGCCGGC
CGCAGGGCCCCTTCCTTATCGCCGACAAGTGGCCCGCGCTGCCCCGCAAGCTGG
ACTCGGTCTTTGAGGAGCCGCTCTCCAAGAAGCTTTTCTTCTTCTCTGGGCGCCA
```

FIGURE 7 (Page 2 of 2)(SEQ ID NO: 3)(cont.)

ref|NM_004994.1| Homo sapiens matrix metalloproteinase 9 (gelatinase B, 92kDa gelatinase, 92kDa type IV collagenase) (MMP9), mRNA (cont.)

GGTGTGGGTGTACACAGGCGCGTCGGTGCTGGGCCCGAGGCGTCTGGACAAGC
TGGGCCTGGGAGCCGACGTGGCCCAGGTGACCGGGGCCCTCCGGAGTGGCAGG
GGGAAGATGCTGCTGTTCAGCGGGCGGCGCCTCTGGAGGTTCGACGTGAAGGC
GCAGATGGTGGATCCCCGGAGCGCCAGCGAGGTGGACCGGATGTTCCCCGGGG
TGCCTTTGGACACGCACGACGTCTTCCAGTACCGAGAGAAAGCCTATTTCTGCC
AGGACCGCTTCTACTGGCGCGTGAGTTCCCGGAGTGAGTTGAACCAGGTGGACC
AAGTGGGCTACGTGACCTATGACATCCTGCAGTGCCCTGAGGACTAGGGCTCCC
GTCCTGCTTTGCAGTGCCATGTAAATCCCCACTGGGACCAACCCTGGGGAAGGA
GCCAGTTTGCCGGATACAAACTGGTATTCTGTTCTGGAGGAAAGGGAGGAGTG
GAGGTGGGCTGGGCCCTCTCTTCTCACCTTTGTTTTTTGTTGGAGTGTTTCTA
ATAAACTTGGATTCTCTAACCTTT

SEQUENCE LISTING

```
<160> NUMBER OF SEQ ID NOS: 3

<210> SEQ ID NO 1
<211> LENGTH: 782
<212> TYPE: DNA
<213> ORGANISM: Homo sapiens

<400> SEQUENCE: 1 agggqccttta gcgtgccgca tcgccgagat ccagcgccca gagagacacc agagaaccca    60
ccatggcccc ctttgagccc ctggcttctg gcatcctgtt gttgctgtgg ctgatagccc   120
ccagcagggc ctgcacctgt gtcccacccc acccacagac ggccttctgc aattccgacc   180
tcgtcatcag ggccaagttc gtggggacac cagaagtcaa ccagaccacc ttataccagc   240
gttatgagat caagatgacc aagatgtata aagggttcca agccttaggg gatgccgctg   300
acatccggtt cgtctacacc cccgccatgg agagtgtctg cggatacttc cacaggtccc   360
acaaccgcag cgaggagttt ctcattgctg gaaaactgca ggatggactc ttgcacatca   420
ctacctgcag tttcgtggct ccctggaaca gcctgagctt agctcagcgc cggggcttca   480
ccaagaccta cactgttggc tgtgaggaat gcacagtgtt tccctgttta tccatcccct   540
gcaaactgca gagtggcact cattgcttgt ggacggacca gctcctccaa ggctctgaaa   600
agggcttcca gtcccgtcac cttgcctgcc tgcctcggga gccagggctg tgcacctggc   660
agtccctgcg gtcccagata gcctgaatcc tgcccggagt ggaactgaag cctgcacagt   720
gtccaccctg ttcccactcc catctttctt ccggacaatg aaataaagag ttaccaccca   780
gc                                                                  782

<210> SEQ ID NO 2
<211> LENGTH: 3069
<212> TYPE: DNA
<213> ORGANISM: Homo sapiens

<400> SEQUENCE: 2
tgtttccgct gcatccagac ttcctcaggc ggtggctgga ggctgcgcat ctggggcttt    60
aaacatacaa agggattgcc aggacctgcg gcggcggcgg cggcggcggg ggctggggcg   120
cggggccgga accatgagcc gctgagccgg gcaaacccca ggccaccgag ccagcggacc   180
ctcggagcgc agccctgcgc cgcggaccag gctccaacca ggcggcgagg cggccacacg   240
```

-continued

```
caccgagcca gcgaccccg ggcgacgcgc ggggccaggg agcgctacga tggaggcgct      300
aatggcccgg ggcgcgctca cgggtcccct gagggcgctc tgtctcctgg gctgcctgct      360
gagccacgcc gccgccgcgc cgtcgcccat catcaagttc cccggcgatg tcgccccccaa     420
aacggacaaa gagttggcag tgcaatacct gaacaccttc tatggctgcc ccaaggagag      480
ctgcaacctg tttgtgctga aggacacact aaagaagatg cagaagttct ttggactgcc      540
ccagacaggt gatcttgacc agaataccat cgagaccatg cggaagccac gctgcggcaa      600
cccagatgtg gccaactaca acttcttccc tcgcaagccc aagtgggaca gaaccagat       660
cacatacagg atcattggct acacacctga tctggaccca gagacagtgg atgatgcctt      720
tgctcgtgcc ttccaagtct ggagcgatgt gacccactg cggttttctc gaatccatga       780
tggagaggca gacatcatga tcaactttgg ccgctgggag catggcgatg ataccccctt      840
tgacggtaag gacggactcc tggctcatgc cttcgcccca ggcactggtg ttgggggaga      900
ctcccatttt gatgacgatg agctatggac cttgggagaa ggccaagtgg tccgtgtgaa      960
gtatggcaac gccgatgggg agtactgcaa gttccccttc ttgttcaatg caaggagta      1020
caacagctgc actgatactg ccgcagcga tggcttcctc tggtgctcca ccacctacaa      1080
ctttgagaag gatggcaagt acggcttctg tccccatgaa gccctgttca ccatgggcgg     1140
caacgctgaa ggacagccct gcaagtttcc attccgcttc cagggcacat cctatgacag     1200
ctgcaccact gagggccgca cggatggcta ccgctggtgc ggcaccactg aggactacga     1260
ccgcgacaag aagtatggct tctgccctga gaccgccatg tccactgttg gtgggaactc     1320
agaaggtgcc ccctgtgtct tcccccttcac tttcctgggc aacaaatatg agagctgcac     1380
cagcgccggc cgcagtgacg gaaagatgtg gtgtgcgacc acagccaact acgatgacga     1440
ccgcaagtgg ggcttctgcc ctgaccaagg gtacagcctg ttcctcgtgg cagcccacga     1500
gtttggccac gccatggggc tggagcactc ccaagaccct ggggccctga tggcacccat     1560
ttacacctac accaagaact tccgtctgtc ccaggatgac atcaagggca ttcaggagct     1620
ctatggggcc tctcctgaca ttgaccttgg caccggcccc accccacac tgggccctgt      1680
cactcctgag atctgcaaac aggacattgt atttgatggc atcgctcaga tccgtggtga     1740
gatcttcttc ttcaaggacc ggttcatttg gcggactgtg acgccacgtg acaagcccat     1800
ggggcccctg ctggtggcca cattctggcc tgagctcccg gaaaagattg atgcggtata     1860
cgaggcccca caggaggaga aggctgtgtt cttttgcaggg aatgaatact ggatctactc     1920
agccagcacc ctggagcgag ggtaccccaa gccactgacc agcctgggac tgcccctga      1980
tgtccagcga gtggatgccg cctttaactg gagcaaaaac aagaagacat acatctttgc     2040
tggagacaaa ttctggagat acaatgaggt gaagaagaaa atggatcctg ctttcccaa      2100
gctcatcgca gatgcctgga tgccatccc cgataacctg gatgccgtcg tggacctgca     2160
gggcggcggt cacagctact tcttcaaggg tgcctattac ctgaagctgg agaaccaaag     2220
tctgaagagc gtgaagtttg aagcatcaa atccgactgg ctaggctgct gagctggccc     2280
tggctcccac aggcccttcc tctccactgc cttcgataca ccgggcctgg agaactagag     2340
aaggacccgg aggggcctgg cagccgtgcc ttcagctcta cagctaatca gcattctcac     2400
tcctacctgg taatttaaga ttccagagag tggctcctcc cggtgcccaa gaatagatgc     2460
tgactgtact cctcccaggc gccccttccc cctccaatcc caccaaccct cagagccacc     2520
cctaaagaga tcctttgata ttttcaacgc agccctgctt gggctgcccc tggtgctgcc     2580
```

```
acacttcagg ctcttctcct ttcacaacct tctgtggctc acagaaccct tggagccaat    2640
ggagactgtc tcaagagggc actggtggcc cgacagcctg gcacagggca gtgggacagg    2700
gcatggccag gtggccactc cagaccctg gcttttcact gctggctgcc ttagaacctt    2760
tcttacatta gcagtttgct ttgtatgcac tttgtttttt tctttgggtc ttgtttttt    2820 tttccactta gaaattgcat ttcctgacag aaggactcag gttgtctgaa gtcactgcac    2880
agtgcatctc agcccacata gtgatggttc ccctgttcac tctacttagc atgtccctac    2940
cgagtctctt ctccactgga tggaggaaaa ccaagccgtg gcttcccgct cagccctccc    3000
tgcccctccc ttcaaccatt ccccatggga aatgtcaaca gtatgaata aagacaccta    3060 ctgagtggc                                                           3069
```

```
<210> SEQ ID NO 3
<211> LENGTH: 2334
<212> TYPE: DNA
<213> ORGANISM: Homo sapiens

<400> SEQUENCE: 3
```

```
agacacctct gccctcacca tgagcctctg gcagcccctg gtcctggtgc tcctggtgct     60
gggctgctgc tttgctgccc ccagacagcg ccagtccacc cttgtgctct ccctgggaga    120
cctgagaacc aatctcaccg acaggcagct ggcagaggaa tacctgtacc gctatggtta    180
cactcgggtg gcagagatgc gtggagagtc gaaatctctg gggcctgcgc tgctgcttct    240
ccagaagcaa ctgtccctgc ccgagaccgg tgagctggat agcgccacgc tgaaggccat    300 gcgaaccca cggtgcgggg tcccagacct gggcagattc caaacctttg agggcgacct    360
caagtggcac caccacaaca tcacctattg gatccaaaac tactcggaag acttgccgcg    420
ggcggtgatt gacgacgcct tgcccgcgc cttcgcactg tggagcgcgg tgacgccgct    480
caccttcact cgcgtgtaca gccgggacgc agacatcgtc atccagtttg gtgtcgcgga    540
gcacggagac gggtatccct tcgacgggaa ggacgggctc ctggcacacg cctttcctcc    600
tggccccggc attcagggag acgcccattt cgacgatgac gagttgtggt ccctgggcaa    660
gggcgtcgtg gttccaactc ggtttggaaa cgcagatggc gcggcctgcc acttccccctt    720 catcttcgag ggccgctcct actctgcctg caccaccgac ggtcgctccg acggcttgcc    780
ctggtgcagt accacggcca actacgacac cgacgaccgg tttggcttct gccccagcga    840
gagactctac acccgggacg gcaatgctga tgggaaaccc tgccagtttc cattcatctt    900
ccaaggccaa tcctactccg cctgcaccac ggacggtcgc tccgacggct accgctggtg    960
cgccaccacc gccaactacg accgggacaa gctcttcggc ttctgcccga ccgagctga   1020 ctcgacggtg atgggggca actcggcggg ggagctgtgc gtcttcccct tcactttcct   1080
gggtaaggag tactcgacct gtaccagcga gggccgcgga gatgggcgcc tctggtgcgc   1140
taccacctcg aactttgaca gcgacaagaa gtggggcttc tgcccggacc aaggatacag   1200
tttgttcctc gtggcggcgc atgagttcgg ccacgcgctg ggcttagatc attcctcagt   1260
gccggaggcg ctcatgtacc ctatgtaccg cttcactgag gggcccccct gcataagga   1320 cgacgtgaat ggcatccggc acctctatgg tcctcgcccct gaacctgagc acggcctcc   1380 aaccaccacc acaccgcagc ccacggctcc ccgacggtc tgccccaccg acccccac    1440 tgtccacccc tcagagcgcc ccacagctgg ccccacaggt ccccctcag ctggccccac   1500 aggtccccc actgctggcc cttctacggc cactactgtg cctttgagtc cggtggacga   1560
tgcctgcaac gtgaacatct cgacgccat cgcggagatt gggaaccagc tgtatttgtt   1620
```

```
caaggatggg aagtactggc gattctctga gggcaggggg agccggccgc agggcccctt    1680
ccttatcgcc gacaagtggc ccgcgctgcc ccgcaagctg gactcggtct ttgaggagcc    1740
gctctccaag aagcttttct tcttctctgg gcgccaggtg tgggtgtaca caggcgcgtc    1800
ggtgctgggc ccgaggcgtc tggacaagct gggcctggga gccgacgtgg cccaggtgac    1860
cggggccctc cggagtggca gggggaagat gctgctgttc agcgggcggc gcctctggag    1920
gttcgacgtg aaggcgcaga tggtggatcc ccggagcgcc agcgaggtgg accggatgtt    1980
ccccggggtg cctttggaca cgcacgacgt cttccagtac cgagagaaag cctatttctg    2040
ccaggaccgc ttctactggc gcgtgagttc ccggagtgag ttgaaccagg tggaccaagt    2100
gggctacgtg acctatgaca tcctgcagtg ccctgaggac tagggctccc gtcctgcttt    2160
gcagtgccat gtaaatcccc actgggacca accctgggga aggagccagt ttgccggata    2220
caaactggta ttctgttctg gaggaaaggg aggagtggag gtgggctggg ccctctcttc    2280
tcacctttgt ttttgttgg agtgtttcta ataaacttgg attctctaac cttt          2334
```

LIVER DISEASE-RELATED METHODS AND SYSTEMS

RELATED APPLICATIONS

This application is a continuation-in-part application of U.S. patent application Ser. No. 10/258,689, filed Oct. 7, 2003 now U.S. Pat. No. 7,141,380. This application claims priority to U.S. patent application Ser. No. 10/258,689 and the following related applications: PCT Patent Application PCT/EP01/04696, filed Apr. 26, 2001, and EP Patent Application EP 1150123A1, filed Apr. 28, 2000.

FIELD OF THE INVENTION

The invention provides diagnostic methods, kits, and systems, and related computer-readable media, which use multiple blood marker values, including serum and plasma marker values, to aid in the diagnosis of the status or progress of a liver disease in a patient.

The invention also provides methods and systems, and related computer-readable media, that use blood marker values, including serum and plasma marker values: (1) to screen for active ingredients useful in the treatment of a liver disease; (2) to aid in the selection of treatment regimens for patients who are predisposed to, or who suffer from, liver disease; and (3) to aid in the design of clinical programs useful in monitoring the status or progress of liver disease in one or more patients.

BACKGROUND OF THE INVENTION

Progressive fibrotic diseases of the liver are a major cause of death throughout the world. The pathogenic process of fibrosis in the liver is critically dependent on proliferation and activation of hepatic stellate cells (also called lipocytes, or fat-storing or Ito cells) and other liver extracellular matrix-producing cells (i.e. portal myofibroblasts and fibroblasts), which synthesize and secrete excess extracellular matrix proteins (1). This process is common to liver disease of all etiologies. Chronic viral hepatitis B and C, alcoholic liver disease, non-alcoholic fatty liver disease and autoimmune and genetic liver diseases all entail the common final pathway of progressive liver fibrosis and the eventual development of cirrhosis.

Hepatic fibrosis is a reversible accumulation of extracellular matrix in response to chronic injury in which nodules have not yet developed, whereas cirrhosis implies a clinically important stage in this process that is usually but not always irreversible, in which thick bands of matrix fully encircle the parenchyma, forming nodules. Cirrhosis is associated with increased risks of liver failure, liver cancer and death. Consequently, to be effective, any liver disease therapy must be directed towards patients with reversible disease (fibrosis), which requires early identification and monitoring of those at risk (2).

Diagnosis of liver fibrosis is usually made by the histological analysis of liver biopsies. A single biopsy can be highly informative in determining diagnosis, prognosis and appropriate management (1A; 2A). The role of surrogate markers in the detection of liver fibrosis is not yet established. Accordingly liver biopsy is currently regarded as the "reference-standard" index of liver fibrosis.

Obtaining biopsies however is costly (3A) and is associated with pain (4A), hemorrhage, or death (5A; 6A). Processing of biopsies is time consuming and labor intensive. For all these reasons frequent repetition of liver biopsies is deemed unacceptable to patients and doctors alike, although monitoring the evolution of disease or response to treatment may require repeated biopsies.

Due to the small size of a needle biopsy and the diffuse nature of many liver diseases, biopsies may not yield results that are truly representative of a patient's disease status (7A). The histological analysis of biopsies requires experience and skill, but remains subjective and prone to both intra- and inter-observer variation (8A; 9A).

There is a considerable clinical need to identify surrogate markers of liver fibrosis. Such markers could be used to estimate the extent of fibrosis in place of a biopsy or, alternatively, they could be used in conjunction with a single liver biopsy to follow-up progression or regression of fibrosis and response to changes in life-style, or anti-fibrotic, antiviral, or other therapies. Ideally, such markers would be based on accurate and reproducible tests that could be automated and performed repeatedly with little disruption to patients.

Serum assays for products of matrix synthesis or degradation, and the enzymes involved in these processes, have been investigated as surrogate markers of liver fibrosis in a number of studies (10A-19A). Generally, the diagnostic performance of these markers has been disappointing, although some of individual assays have shown promise in detecting cirrhosis (20A; 21A), in alcoholic liver disease (Hyaluronic Acid) (22A), or milder fibrosis in non-alcoholic fatty liver disease (NAFLD) (YKL-40) (23A). Other markers have been reported to reflect changes in liver histology attributable to antiviral therapy (11A; 24A; 25A).

Biopsy and the serum markers compare different things: serum parameters characterize dynamic processes in the liver, while the biopsy characterizes the fibrotic manifestation at a fixed time-point. There may be a highly active fibrotic process in the liver, although fibrotic tissue has not yet been developed. In contrast, there may be large clusters of fibrotic tissue in the liver but the fibrotic activity stopped or discontinued temporarily.

An alternative approach is to combine a number of serum markers to generate an algorithm capable of evaluating fibrosis over a range of severity. In chronic Hepatitis C (CHC) (18A; 26A), and chronic hepatitis B, five parameters have been identified that could detect significant fibrosis with a positive predictive value (PPV) of 80%. However, these approaches failed to determine the severity of fibrosis in approximately 50% of patients and subsequent independent validation has questioned the utility of these markers (Rossi, et al., *Clinical Chemistry*. 49(3):450-4, 2003 March).

Previous studies have suggested that serum levels of extracellular matrix proteins (or their cleavage fragments) may be used to assess the severity and progression of liver fibrosis (U.S. Pat. No. 5,316,914, and EP 0 283 779). Different serum markers have been investigated and correlations with liver biopsies and severity of liver diseases have been found (6). Some of the makers that have been used for the assessment of liver fibrosis are PIIINP, Laminin, Hyaluronan, Collagen IV, TIMP-1, Tenascin, MMP-2 and Fibronectin. These markers have been measured and their capability to assess liver fibrosis has been shown. Nevertheless, neither the diagnostic accuracy nor the specificity of diagnostic markers is adequate to predict fibrosis scores with sufficient clinical utility.

Combinations of markers have been used in an effort to increase the diagnostic value of the simple biological index PGA (which includes Prothrombin time (PT), serum gamma-glutamyl transpeptidase (GGT), apolipoprotein A1 (Apo A1)), and the index PGAA (which adds alpha-2-macroglobulin ($A_2M$) to the PGA index) have been described for the diagnosis of alcoholic liver disease in drinkers (7, 8).

Although the PGA and PGAA indices have been combined with single serum markers (9, 10), such serum markers have not yet provided a reliable means of assessing liver diseases.

More recently, $\alpha_2$-macroglobulin, $\alpha_2$-globulin (or haptoglobin), γ-globulin, apolipoprotein-A1, γ-glutamyl-transpeptidase, and total bilirubin have been combined to assess the status of liver fibrosis (11). The marker algorithm derived showed a strong diagnostic performance at the very end of the fibrosis spectrum—either for the identification or for the exclusion of severe or relatively mild fibrosis. The algorithm did not provide a diagnostic tool useful for identifying patients with moderate degrees of fibrosis.

Pilette, et al., *J. Hepatol.*, Vol. 28, No. 3, 1998, pages 439-446 (*Chemical Abstracts*, Vol. 130, No. 7, Feb. 15, 1999 (Columbus, Ohio, U.S.; abstract no. 78389)) ("Pilette") disclosed the correlation of the diagnostic markers hyaluronate, N-terminal peptide of procollagen Ill, laminin, and other serum markers by a mathematical algorithm for purposes of histopathological evaluation of liver fibrosis. Pilette determined the best morphometric method for the evaluation of hepatic fibrosis but did not combine markers algorithmically to obtain a diagnostic systems or methods that were superior to those which only used hyaluronic acid.

Guechot, et al., *Clinical Chemistry*, Vol. 42, No. 4 (April 1996) pp. 558-563 (XP002 1 49459 Winston; U.S.) ("Guechot"), provided a comparative assessment of the performance of hyaluronic acid and PIIINP as serum markers to assess liver disease. However, Guechot made no attempt to combine the results from hyaluronic acid and PIIINP in order to obtain a serum marker-based assessment of liver fibrosis that would be superior to the use of any of the two markers alone.

Accordingly, the need exists for accurate, reproducible, and computer-implementable methods, systems, kits, and media that employ two or more liver disease-related blood markers, e.g., plasma or serum markers, to aid in the determination of the status or progress of a liver disease in a patient. Such methods, systems, kits, and media would enable health care providers to ascertain the status or progress of a patient's liver disease at two or more time points without subjecting the patient to risky biopsies.

Further, such methods, systems, kits, and media would prove useful in designing or monitoring liver-disease related clinical trials, and in screening for agents useful in the treatment of liver disease.

SUMMARY OF THE INVENTION

The invention provides diagnostic methods, kits, and systems, and related computer-readable media, which use multiple blood marker values, including serum and plasma marker values, to aid in the diagnosis of the status or progress of a liver disease in a patient.

The invention also provides methods and systems, and related computer-readable media, that use blood marker values, including serum and plasma marker values: (1) to screen for active ingredients useful in the treatment of a liver disease; (2) to aid in the selection of treatment regimens for patients who are predisposed to, or who suffer from, liver disease; and (3) to aid in the design of clinical programs useful in monitoring the status or progress of liver disease in one or more patients.

The invention facilitates point of care or remote diagnoses of liver diseases and assists health care providers in monitoring the status or progress of liver disease at two or more time points. Significantly, the invention provides health care decision makers with an alternative to potentially inaccurate and risky liver biopsies.

The invention employs computer-implementable algorithmic methods which utilize two or more liver disease-related marker values. The predictive value of the invention has been validated in clinical studies which monitored the status or progress of liver disease. These clinical trials validated the invention on a cross-sectional basis, in which analyses were conducted at discrete time points, and longitudinally, in which analyses were conducted at two or more time points.

Accordingly, the invention can be used to:
(a) measure the dynamic processes of extracellular matrix synthesis (fibrogenesis) and extracellular matrix degradation (fibrolysis); and
(b) obtain results that reflect the degree of fibrosis and the dynamic changes occurring in liver tissue through prediction of a liver fibrosis histological score.

The invention is especially useful in aiding in the diagnosis and treatment of patients for whom a liver biopsy would be very risky. Such patients may suffer from coagulopathy, may be averse to undergoing a biopsy, or may not have access to expert histopathology. In addition, the invention can be used by health care decision makers to assess liver fibrosis associated with chronic liver diseases such as hereditary haemochromatosis, primary biliary cirrhosis, and primary sclerosing cholangitis. Further, the invention is especially useful in cases where fibrosis may be unevenly distributed and sampling error poses a significant problem.

In one embodiment, the invention provides a method comprising aiding in the diagnosis of the status or progress of a liver disease in a patient by determining at one or more time points a predictor value for each time point, wherein a comparison at one or more time points of the predictor value and a comparative data set is used by a health care decision maker to ascertain the status or progress of patient liver disease, and wherein patient predictor values are calculated by inputting data for two or more blood markers, e.g., two or more plasma or serum markers, and optionally one or more supplementary markers, into a linear or nonlinear function algorithm derived by correlating reference liver histopathological and blood markers, e.g., plasma or serum marker data.

A "comparative data set" can comprise any data reflecting any qualitative or quantitative indicia of histopathological conditions. In one embodiment, the comparative data set can comprise one or more numerical values, or range of numerical values, associated with histopathological conditions. For example, a comparative data set may comprise various integer sets, e.g., the integers 0 through 5, wherein different groupings of those six integers correlate to different liver disease states, e.g., 0-1 may correlate to a mild disease state, 2-3 correlate to a moderate disease state, and 4-5 may correlate to a severe disease state. Therefore, a comparative data set may correlate to an established liver biopsy scoring system, e.g., the Scheuer scoring system (0-4) and the modified Histological Activity ("HAI") fibrosis score (Ishak score) (0-6).

In a preferred embodiment, blood markers are serum markers that are selected from at least two or more of the following: N-terminal procollagen III propeptide (PIIINP), Collagen IV, Collagen VI, Tenascin, Laminin, Hyaluronan, MMP-2, TIMP-1, MMP-9/TIMP-1 complex, alanin-aminotransferase (ALT), aspartat-aminotransferase (AST). Supplementary markers include, but are not limited to, patient weight, sex, age, and transaminase level.

In another embodiment of the invention, the linear or nonlinear function algorithm is derived by correlating reference liver histopathological and blood marker, e.g., plasma and serum marker, data using either discriminant function analysis or nonparametric regression analysis. Reference liver histopathological and blood marker data e.g., plasma and serum marker data, can include data indicative of fibrogenesis or fibrolysis, elevated liver disease serum markers, or other liver disease clinical symptoms.

In one embodiment, reference liver histopathological and blood marker data, e.g., plasma and serum marker data, is based upon data relating to one or more subjects other than the diagnosed patient. In another embodiment, reference liver histopathological and blood marker data, e.g., plasma and serum marker data, is based upon data previously obtained from the diagnosed patient, and is optionally also based on data obtained from one or more other subjects.

In one embodiment, a linear or nonlinear function algorithm is derived by correlating reference liver histopathological and blood marker data e.g., plasma and serum marker data, by:
(a) compiling a data set comprising blood marker data e.g., plasma or serum marker data, and histopathological data for a first group of subjects;
(b) deriving a linear or nonlinear function algorithm from the compiled data set through application of an analytical methodology;
(c) calculating validation biopsy score values for a second group of subjects by inputting data comprising blood marker data, e.g., plasma or serum marker data, values for the second group of subjects into the algorithm derived in step (b) and;
(d) comparing validation biopsy score values calculated in step (c) with liver histopathological scores for the second group of subjects; and
(e) if the validation biopsy scores determined in step (c) do not correlate within a clinically-acceptable tolerance level with liver histopathological scores for the second group of subjects, performing the following operations (i)-(iii) until such tolerance is satisfied: (i) modifying the algorithm on a basis or bases comprising (1) revising the data set for the first group of subjects, and (2) revising or changing the analytical methodology (ii) calculating validation biopsy score values for the second group of subjects by inputting data comprising blood marker data, e.g., plasma or serum marker data values, for the second group of subjects into the modified algorithm (iii) assessing whether validation biopsy score values calculated using the modified algorithm correlate with liver histopathological scores for the second group of subjects within the clinically-acceptable tolerance level.

The analytical methodology may include statistical techniques including discriminant function analysis and nonparametric regression analysis, as well as techniques such as classification trees or neural networks.

In another embodiment, the invention provides a data structure stored in a computer-readable medium that may be read by a microprocessor and that comprises at least one code that uniquely identifies a linear or nonlinear function algorithm derived in a manner described herein.

In another embodiment, the invention provides a diagnostic kit comprising:
(a) a data structure stored in a computer-readable medium that may be read by a microprocessor and that comprises at least one code that uniquely identifies a linear or nonlinear function algorithm derived in a manner described herein; and
(b) one or more immunoassays that detect and determine patient serum marker values.

In another embodiment, the invention provides computer-implementable methods and systems for determining whether a composition is useful in the treatment of a liver disease comprising evaluating data useful in diagnosing the status or progress of a liver disease in a patient treated with the composition, wherein:
(a) the diagnosis is made by a health care provider by determining algorithmically at one or more time points a predictor value for each time point;
(b) a comparison at one or more time points of the predictor value and a comparative data set is used by a health care provider to ascertain the status or progress of patient liver disease; and
(c) patient predictor values are calculated by inputting data for two or more blood markers, e.g., plasma or serum markers, into a linear or nonlinear function algorithm derived by correlating reference liver histopathological and blood marker data, e.g., plasma or serum marker data.

The aforementioned methods, systems, and kits of the invention can also be used by health care providers: (1) to determine treatment regimens for patients that are predisposed to, or suffer from, liver disease; and (2) to design clinical programs useful in monitoring the status or progress of liver disease in one or more patients.

These and other aspects of the invention are described further in the detailed description of the invention.

BRIEF DESCRIPTION OF THE FIGURES

FIG. 2.

FIG. 3.

FIG. 4: FIG. 4 illustrates a Box and Whisker Plot for a Validation Data Set ($G_V$) showing Scheuer Fibrosis Score versus Discriminant Scores determined in accordance with the invention.

FIG. 5 depicts the nucleotide sequence for human TIMP1 mRNA (SEQ ID NO: 1).

FIG. 6 depicts the nucleotide sequence for human MMP2 mRNA (SEQ ID NO: 2).

FIG. 7 depicts the nucleotide sequence for human MMP9 mRNA (SEQ ID NO: 3).

DETAILED DESCRIPTION OF THE INVENTION

Figure 1:
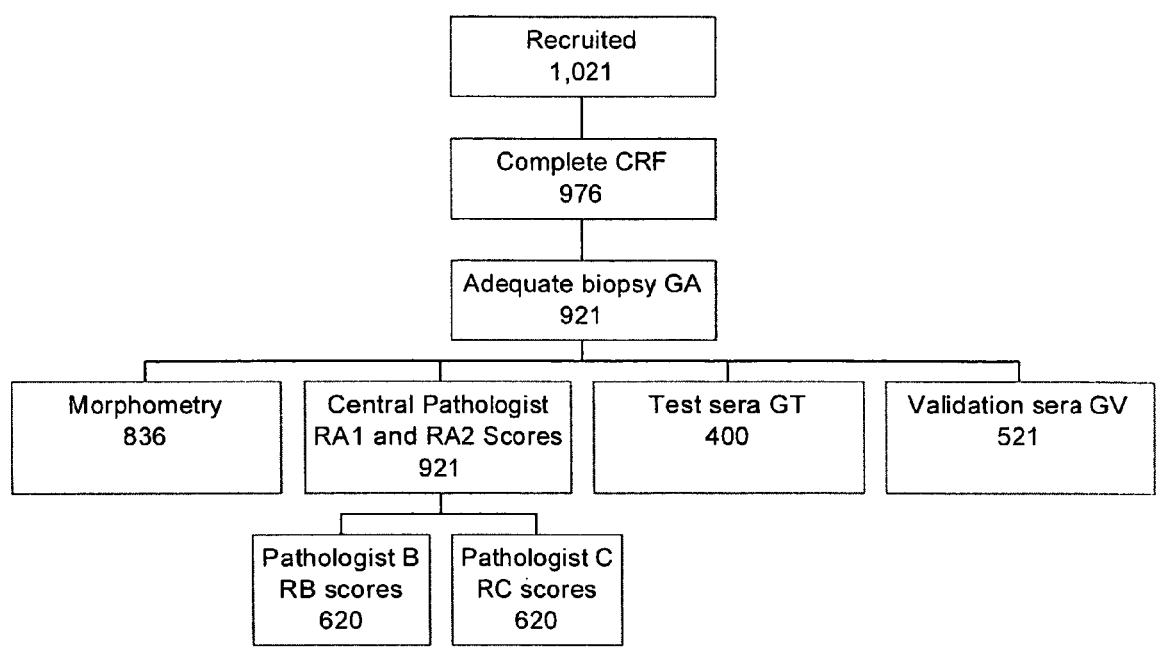
FIG. 1 illustrates a flow chart depicting the recruitment and participation of subjects in the ELF study referenced in the Detailed Description of the Invention.

As used herein, the following terms have the following respective meanings.

"Antibody" means any antibody, including polyclonal or monoclonal antibodies or any fragment thereof, that binds to patient diagnostic serum marker epitopes. Monoclonal and/or polyclonal antibodies may be used in methods and systems of the invention. "Antibody" or other similar term as used herein includes a whole immunoglobulin that is either monoclonal or polyclonal, as well as immunoreactive fragments that specifically bind to the marker, including Fab, Fab', F(ab')$_2$ and F(v). The term "Antibody" also includes binding-proteins, especially hyaluronic acid binding protein (HABP). Preferred serum marker antibodies are described hereinafter.

The human fluid samples used in the assays of the invention can be any samples that contain patient diagnostic markers, e.g. blood, serum, plasma, urine, sputum or broncho alveolar lavage (BAL) or any other body fluid. Typically a serum or plasma sample is employed.

Antibodies used in the invention can be prepared by techniques generally known in the art, and are typically generated to a sample of the markers—either as an isolated, naturally occurring protein, as a recombinantly expressed protein, or a synthetic peptide representing an antigenic portion of the natural protein. The second antibody is conjugated to a detector group, e.g. alkaline phosphatase, horseradish peroxidase, a fluorescent dye or any other labeling moiety generally usefull to detect biomolecules in diagnostic assays. Conjugates are prepared by techniques generally known in the art.

"Immunoassays" determine the presence of a patient diagnostic serum marker in a biological sample by reacting the sample with an antibody that binds to the serum marker, the reaction being carried out for a time and under conditions allowing the formation of an immunocomplex between the antibodies and the serum markers. The quantitative determination of such an immunocomplex is then performed.

In one version, the antibody used is an antibody generated by administering to a mammal (e.g., a rabbit, goat, mouse, pig, etc.) an immunogen that is a serum marker, an immunogenic fragment of a serum marker, or an anti-serum marker-binding idiotypic antibody. Other usefull immunoassays feature the use of serum marker-binding antibodies generally (regardless of whether they are raised to one of the immunogens described above). A sandwich immunoassay format may be employed which uses a second antibody that also binds to a serum marker, one of the two antibodies being immobilized and the other being labeled.

Preferred immunoassays detect an immobilized complex between a serum marker and a serum marker-binding antibody using a second antibody that is labeled and binds to the first antibody. Alternatively, the first version features a sandwich format in which the second antibody also binds a serum marker. In the sandwich immunoassay procedures, a serum marker-binding antibody can be a capture antibody attached to an insoluble material and the second a serum marker-binding antibody can be a labeling antibody. The above-described sandwich immunoassay procedures can be used with the antibodies described hereinafter.

The assays used in the invention can be used to determine a blood marker, e.g., a plasma or serum marker in samples including urine, plasma, serum, peritoneal fluid or lymphatic fluid. Immunoassay kits for detecting a serum marker can also be used in the invention, and comprise a serum marker-binding antibody and the means for determining binding of the antibody to a serum marker in a biological sample. In preferred embodiments, the kit includes one of the second antibodies or the competing antigens described above.

A "comparative data set" has been defined previously herein.

"Reference liver histopathological and blood marker data" and "histopathological data" includes but is not limited to serum or plasma data indicative of fibrogenesis or fibrolysis, interface hepatitis, necrosis, inflammation, necroinflammation, elevated liver disease serum markers, or other liver disease clinical symptoms. Thus, reference liver histopathological and serum marker data includes, but is not limited to, data reflecting application of one or more of liver biopsy tests which use the Scheuer Score (0-4) and HAI Score (Ishak Score) (0-6). Other reference liver histopathological and serum marker data can relate to the Modified Ishak Score (HAI) A—Interface Hepatitis (0-4), the Modified Ishak Score (HAI) B—Confluent Necrosis (0-6), the Modified Ishak Score (HAI) C—Spotty Necrosis (0-4), and the Modified Ishak Score (HAI) D—Portal Inflammation (0-4).

These and other applicable scoring systems are well-known to those of ordinary skill in the art. See, e.g., Scheuer, et al., "*Liver Biopsy Interpretation*" (W. B. Saunders 2000); Scheuer, *J Hepatol.* 1991; 13:372-374; Ishak, et al., *J Hepatol.* 1995; 22:696-699. Because of differences which exist with respect to the pattern of fibrosis in diseases such as alcoholic liver disease, scoring systems may need to be modified for purposes of assigning scores in non-viral liver disease cases.

"Reference liver histopathological and blood marker data" includes data reflecting values determined from all such modified scores and scoring systems.

Reference liver histopathological and blood marker, e.g., plasma and serum marker data also includes, but is not limited to, data reflecting elevated serum levels of transaminases such as alanine-aminotransferase (ALT) and aspartate-aminotransferase (AST), and qualitative or quantitative evaluations of symptoms such as jaundice.

"Validation biopsy scores" are values determined by inputting liver histopathological and serum marker data values into an algorithm.

"Discriminant function analysis" is a technique used to determine which variables discriminate between two or more naturally occurring mutually exclusive groups. The basic idea underlying discriminant function analysis is to determine whether groups differ with regard to a set of predictor variables which may or may not be independent of each other, and then to use those variables to predict group membership (e.g., of new cases).

Discriminant function analysis starts with an outcome variable that is categorical (two or more mutually exclusive levels). The model assumes that these levels can be discriminated by a set of predictor variables which, like ANOVA (analysis of variance), can be continuous or categorical (but are preferably continuous) and, like ANOVA assumes that the underlying discriminant functions are linear. Discriminant analysis does not "partition variation". It does look for canonical correlations among the set of predictor variables and uses these correlates to build eigenfunctions that explain percentages of the total variation of all predictor variables over all levels of the outcome variable.

The output of the analysis is a set of linear discriminant functions (eigenfunctions) that use combinations of the predictor variables to generate a "discriminant score" regardless of the level of the outcome variable. The percentage of total variation is presented for each function. In addition, for each eigenfunction, a set of Fisher Discriminant Functions are developed that produce a discriminant score based on combinations of the predictor variables within each level of the outcome variable.

Usually, several variables are included in a study in order to see which one(s) contribute to the discrimination between groups. In that case, a matrix of total variances and co-variances is generated. Similarly, a matrix of pooled within-group variances and co-variances may be generated. A comparison of those two matrices via multivariate F tests is made in order to determine whether or not there are any significant differences (with regard to all variables) between groups. This procedure is identical to multivariate analysis of variance or MANOVA. As in MANOVA, one could first perform the multivariate test, and, if statistically significant, proceed to see which of the variables have significantly different means across the groups.

For a set of observations containing one or more quantitative variables and a classification variable defining groups of observations, the discrimination procedure develops a discriminant criterion to classify each observation into one of the groups. In order to get an idea of how well a discriminant criterion "performs", it is necessary to classify (a priori) different cases, that is, cases that were not used to estimate the discriminant criterion. Only the classification of new cases enables an assessment of the predictive validity of the discriminant criterion.

In order to validate the derived criterion, the classification can be applied to other data sets. The data set used to derive the discriminant criterion is called the training or calibration data set or patient training cohort. The data set used to validate the performance of the discriminant criteria is called the validation data set or validation cohort.

The discriminant criterion (function(s) or algorithm), determines a measure of generalized squared distance. These distances are based on the pooled co-variance matrix. Either Mahalanobis or Euclidean distance can be used to determine proximity. These distances can be used to identify groupings of the outcome levels and so determine a possible reduction of levels for the variable.

A "pooled co-variance matrix" is a numerical matrix formed by adding together the components of the covariance matrix for each subpopulation in an analysis.

A "predictor" is any variable that may be applied to a function to generate a dependent or response variable or a "predictor value". In one embodiment of the instant invention, a predictor value may be a discriminant score determined through discriminant function analysis of two or more patient blood markers (e.g., plasma or serum markers). For example, a linear model specifies the (linear) relationship between a dependent (or response) variable Y, and a set of predictor variables, the X's, so that $$Y = b_0 + b_1 X_1 + b_2 X_2 + \ldots + b_k X_k$$

In this equation $b_0$ is the regression coefficient for the intercept and the $b_i$ values are the regression coefficients (for variables 1 through k) computed from the data.

"Classification trees" are used to predict membership of cases or objects in the classes of a categorical dependent variable from their measurements on one or more predictor variables. Classification tree analysis is one of the main techniques used in so-called Data Mining. The goal of classification trees is to predict or explain responses on a categorical dependent variable, and as such, the available techniques have much in common with the techniques used in the more traditional methods of Discriminant Analysis, Cluster Analysis, Nonparametric Statistics, and Nonlinear Estimation.

The flexibility of classification trees makes them a very attractive analysis option, but this is not to say that their use is recommended to the exclusion of more traditional methods. Indeed, when the typically more stringent theoretical and distributional assumptions of more traditional methods are met, the traditional methods may be preferable. But as an exploratory technique, or as a technique of last resort when traditional methods fail, classification trees are, in the opinion of many researchers, unsurpassed. Classification trees are widely used in applied fields as diverse as medicine (diagnosis), computer science (data structures), botany (classification), and psychology (decision theory). Classification trees readily lend themselves to being displayed graphically, helping to make them easier to interpret than they would be if only a strict numerical interpretation were possible.

"Neural Networks" are analytic techniques modeled after the (hypothesized) processes of learning in the cognitive system and the neurological functions of the brain and capable of predicting new observations (on specific variables) from other observations (on the same or other variables) after executing a process of so-called learning from existing data. Neural Networks is one of the Data Mining techniques. The first step is to design a specific network architecture (that includes a specific number of "layers" each consisting of a certain number of "neurons"). The size and structure of the network needs to match the nature (e.g., the formal complexity) of the investigated phenomenon. Because the latter is obviously not known very well at this early stage, this task is not easy and often involves multiple "trials and errors."

The neural network is then subjected to the process of "training." In that phase, computer memory acts as neurons that apply an iterative process to the number of inputs (variables) to adjust the weights of the network in order to optimally predict the sample data on which the "training" is performed. After the phase of learning from an existing data set, the new network is ready and it can then be used to generate predictions.

In one embodiment of the invention, neural networks can comprise memories of one or more personal or mainframe computers or computerized point of care device.

"Computer" refers to a combination of a particular computer hardware system and a particular software operating system. A computer or computerized system of the invention can comprise handheld calculator. Examples of useful hardware systems include those with any type of suitable data processor. The term "computer" also includes, but is not limited to, personal computers (PC) having an operating system such as DOS, Windows®, OS/2® or Linux®; Macintosh® computers; computers having JAVA®-OS as the operating system; and graphical workstations such as the computers of Sun Microsystems® and Silicon Graphics®, and other computers having some version of the UNIX operating system such as AIX® or SOLARIS® of Sun Microsystems®; embedded computers executing a control scheduler as a thin version of an operating system, a handheld device; any other device featuring known and available operating system; as well as any type of device which has a data processor of some type with an associated memory.

While the invention will be described in the general context of computer-executable instructions of a computer program that runs on a personal computer, those skilled in the art will recognize that the invention also may be implemented in combination with other program modules. Generally, program modules include routines, programs, components, and data structures that perform particular tasks or implement particular abstract data types. Moreover, those skilled in the art will appreciate that the invention may be practiced with other computer system configurations, including hand-held devices, multi-processor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

A purely illustrative system for implementing the invention includes a conventional personal computer, including a processing unit, a system memory, and a system bus that couples various system components including the system memory to the processing unit. The system bus may be any of several types of bus structure including a memory bus or memory controller, a peripheral bus, and a local bus using any of a variety of conventional bus architectures such as PCI, VESA, Microchannel, ISA and EISA, to name a few. The system memory includes a read only memory (ROM) and random access memory (RAM). A basic input/output system (BIOS), containing the basic routines that helps to transfer information between elements within the personal computer, such as during start-up, is stored in ROM.

The personal computer further includes a hard disk drive, a magnetic disk drive, e.g., to read from or write to a removable disk, and an optical disk drive, e.g., for reading a CD-ROM disk or to read from or write to other optical media. The hard disk drive, magnetic disk drive, and optical disk drive are connected to the system bus by a hard disk drive interface, a magnetic disk drive interface, and an optical drive interface, respectively. The drives and their associated computer-readable media provide nonvolatile storage of data, data structure, computer-executable instructions, etc. for the personal computer. Although the description of computer-readable media above refers to a hard disk, a removable magnetic disk and a CD, it should be appreciated by those skilled in the art that other types of media which are readable by computer, such as magnetic cassettes, flash memory card, digital video disks, Bernoulli cartridges, and the like, may also be used in the exemplary operating environment.

A number of program modules may be stored in the drive's RAM, including an operating system, one or more application programs, other program modules, and program data. A user may enter commands and information into the personal computer through a keyboard and a pointing device, such as a mouse. Other input devices may include a microphone, joystick, game pad, satellite dish, scanner, or the like. These and other input devices are often connected to the processing unit through a serial port interface that is coupled to the system bus, but may be connected by other interfaces, such as a parallel port, game port or a universal serial bus (USB). A monitor or other type of display device is also connected to the system bus via an interface, such as a video adapter. In addition to the monitor, personal computers typically include other peripheral output devices (not shown), such as speakers and printers.

The personal computer may operate in a networked environment using logical connections to one or more remote computers, such as a remote computer. The remote computer may be a server, a router, a peer device or other common network node, and typically includes many or all of the elements described relative to the personal computer. Logical connections include a local area network (LAN) and a wide area network (WAN). Such networking environments are commonplace in offices, enterprise-wide computer networks (such as hospital computers), intranets and the Internet.

When used in a LAN networking environment, the personal computer can be connected to the local network through a network interface or adapter. When used in a WAN networking environment, the personal computer typically includes a modem or other means for establishing communications over the wide area network, such as the Internet. The modem, which may be internal or external, is connected to the system bus via the serial port interface. In a networked environment, program modules depicted relative to the personal computer, or portions thereof, may be stored in the remote memory storage device. It will be appreciated that the network connections shown are exemplary and other means of establishing a communications link between the computers may be used.

One purely illustrative implementation platform of the present invention is a system implemented on an IBM compatible personal computer having at least eight megabytes of main memory and a gigabyte hard disk drive, with Microsoft Windows as the user interface and any variety of data base management software including Paradox. The application software implementing predictive functions can be written in any variety of languages, including but not limited to C++, and is stored on computer readable media as defined hereinafter. A user enters commands and information reflecting patient diagnostic markers into the personal computer through a keyboard and a pointing device, such as a mouse.

In a preferred embodiment, the invention provides a data structure stored in a computer-readable medium, to be read by a microprocessor comprising at least one code that uniquely identifies predictor functions and values derived as described hereinafter. Examples of preferred computer usable media include: nonvolatile, hard-coded type mediums such as read only memories (ROMs) or erasable, electrically programmable read only memories (EEPROMs), recordable type mediums such as floppy disks, hard disk drives and CD-ROMs, and transmission type media such as digital and analog communication links.

A "data structure" can include a collection of related data elements, together with a set of operations which reflect the relationships among the elements. A data structure can be considered to reflect the organization of data and its storage allocation within a device such as a computer.

Thus, a data structure may comprise an organization of information, usually in memory, for better algorithm efficiency, such as queue, stack, linked list, heap, dictionary, and tree, or conceptual unity, such as the name and address of a person. It may include redundant information, such as length of the list or number of nodes in a subtree. A data structure may be an external data structure, which is efficient even when accessing most of the data is very slow, such as on a disk. A data structure can be a passive data structure which is only changed by external threads or processes, in contrast to an active data structure. An active or functional data structure has an associated thread or process that performs internal operations to give the external behavior of another, usually more general, data structure. A data structure also can be a persistent data structure that preserves its old versions, that is, previous versions may be queried in addition to the latest version. A data structure can be a recursive data structure that is partially composed of smaller or simpler instances of the same data structure. A data structure can also be an abstract data type, i.e., set of data values and associated operations that are precisely specified independent of any particular implementation.

These examples of data structures, as with all exemplified embodiments herein, are illustrative only and are in no way limiting.

A diagnostic system of the invention may comprise a handheld device useful in point of care applications or may be a system that operates remotely from the point of patient care. In either case the system can include companion software programmed in any useful language to implement diagnostic methods of the invention in accordance with algorithms or other analytical techniques described herein.

"Point of care testing" refers to real time diagnostic testing that can be done in a rapid time frame so that the resulting test is performed faster than comparable tests that do not employ this system. Point of care testing can be performed rapidly and on site, such as in a doctor's office, at a bedside, in a stat laboratory, emergency room or other such locales, particularly where rapid and accurate results are required. The patient can be present, but such presence is not required. Point of care includes, but is not limited to: emergency rooms, operating rooms, hospital laboratories and other clinical laboratories, doctor's offices, in the field, or in any situation in which a rapid and accurate result is desired.

The term "patient" refers to an animal, preferably a mammal, and most preferably a human.

A "health care provider" or "health care decision maker" comprises any individual authorized to diagnose or treat a patient, or to assist in the diagnosis or treatment of a patient. In the context of identifying useful new drugs to treat liver disease, a health care provider can be an individual who is not authorized to diagnose or treat a patient, or to assist in the diagnosis or treatment of a patient.

"Blood marker", "Blood markers", and "Blood markers, e.g., plasma and serum markers" include, but are not limited to, the serum markers N-terminal procollagen III propeptide (PIIINP), Collagen IV, Collagen VI, Tenascin, Laminin, Hyaluronan, MMP-2, TIMP-1, and MMP-9/TIMP-1 complex. "Blood markers, e.g., plasma and serum markers" are referred to interchangeably as "liver disease serum marker gene polypeptides". "Supplementary markers" include but are not limited to patient weight, sex, age, and patient serum levels of transaminases such as alanin-aminotransferase (ALT) and aspartat-aminotransferase (AST).

"Liver disease" includes any disease associated with liver fibrogenesis or fibrolysis. Such diseases include but are not limited to cirrhosis, alcoholic liver disease, hepatic steatosis, steatohepatitis, nonalcoholic liver disease including nonalcoholic steatohepatitis, liver infections caused by viral infections such as hepatitis B and hepatitis C infections, responses to other pathogens such as schistosomiasis, hereditary haemochromatosis, primary biliary cirrhosis and primary sclerosing cholangitis, reactions to drugs such as methotrexate and congenital disorders such as biliary atresia.

"Validation cohort marker score values" means a numerical score derived from the linear combination of the discriminant weights obtained from the training cohort and marker values for each patient in the validation cohort "Patient diagnostic marker cut-off values" means the value of a marker of combination of markers at which a predetermined sensitivity or specificity is achieved.

"Receiver Operator Characteristic Curve-Scheuer Modified Scoring System Validation Data": the Receiver Operator Characteristic curve generated using the data generated in the validation cohort based on a bifurcated Scheurer Scoring system.

"Receiver Operator Characteristic Curve-Ishak Modified Scoring System Validation Data": the Receiver Operator Characteristic curve generated using the data generated in the validation cohort based on a bifurcated Ishak Scoring system.

"Negative Predictive Power" ("NPV"): The probability of not having a disease given that a marker value (or set of marker values) is not elevated above a defined cutoff.

"Positive Predictive Value" ("PPV"): means the probability of having a disease given that a maker value (or set of marker values) is elevated above a defined cutoff "Receiver Operator Characteristic Curve" ("ROC"): is graphical representation of the functional relationship between the distribution of a marker's sensitivity and 1-specificity values in a cohort of diseased persons and in a cohort of non-diseased persons.

"Area Under the Curve" ("AUC") is a number which represents the area under a Receiver Operator Characteristic curve. The closer this number is to one, the more the marker values discriminate between diseased and non-diseased cohorts "McNemar Chi-square Test" ("The McNemar $\chi^2$ test") is a statistical test used to determine if two correlated proportions (proportions that share a common numerator but different denominators) are significantly different from each other.

A "nonparametric regression analysis" is a set of statistical techniques that allows the fitting of a line for bivariate data that make little or no assumptions concerning the distribution of each variable or the error in estimation of each variable. Examples are: Theil estimators of location, Passing-Bablok regression, and Deming regression.

"Cut-off values" are numerical value of a marker (or set of markers) that defines a specified sensitivity or specificity.

The current reference standard to assess fibrosis in the liver is the liver biopsy. In a biopsy, tissue samples randomly taken out of the liver are cut into slices which are examined by an expert using a microscope.

There are numerous problems associated with liver biopsies, including the following sources of uncertainty: distribution of fibrosis in the liver (where there is clustered fibrosis, the needle might have hit regions of the liver not affected by fibrosis), failed sample preparation (e.g. not enough tissue material), and pathologist subjectivity. Furthermore, the fibrotic state of the liver is usually described using scores and there are many different, and possibly incompatible, scoring systems (e.g. Scheuer Score, Ishak Scores, etc.). For example, two independent pathologists may have to score the same biopsy samples for the same patient at two different timepoints using two different scoring systems. In this case, the number of assessments where the two pathologists came to identical results ranged from only 36% to 46%.

The term "equivalent", with respect to a nucleotide sequence, is understood to include nucleotide sequences encoding functionally equivalent polypeptides. Equivalent nucleotide sequences will include sequences that differ by one or more nucleotide substitutions, additions or deletions, such as allelic variants and therefore include sequences that differ due to the degeneracy of the genetic code. "Equivalent" also is used to refer to amino acid sequences that are functionally equivalent to the amino acid sequence of a mammalian homolog of a blood (e.g., sera) marker protein, but which have different amino acid sequences, e.g., at least one, but fewer than 30, 20, 10, 7, 5, or 3 differences, e.g., substitutions, additions, or deletions.

As used herein, the terms "liver disease serum marker gene" refers to a nucleic acid which: (1) encodes liver disease blood (e.g., serum) marker proteins, including liver disease serum marker proteins identified herein; and (2) which are associated with an open reading frame, including both exon and (optionally) intron sequences. A "liver disease serum marker gene" can comprise exon sequences, though it may optionally include intron sequences which are derived from, for example, a related or unrelated chromosomal gene. The term "intron" refers to a DNA sequence present in a given gene which is not translated into protein and is generally found between exons. A gene can further include regulatory sequences, e.g., a promoter, enhancer and so forth. "Liver disease serum marker gene" includes but is not limited to nucleotide sequences which are complementary, equivalent, or homologous to SEQ ID NOS: 1-3 herein.

"Homology", "homologs of", "homologous", or "identity" or "similarity" refers. to sequence similarity between two polypeptides or between two nucleic acid molecules, with identity being a more strict comparison. Homology and identity can each be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for determining sequence identity are well-known and described in the art.

Preferred nucleic acids used in the instant invention have a sequence at least 70%, and more preferably 80% identical and more preferably 90% and even more preferably at least 95% identical to, or complementary to, a nucleic acid sequence of a mammalian homolog of a liver disease serum marker gene. Particularly preferred nucleic acids used in the instant invention have a sequence at least 70%, and more preferably 80% identical and more preferably 90% and even more preferably at least 95% identical to, or complementary to, a nucleic acid sequence of a mammalian homolog of a liver disease blood (e.g., serum) marker gene.

Immunoassays.

Serum immunoassays were selected to detect and measure levels of N-terminal procollagen III propeptide (PIIINP), Collagen IV, Collagen VI, Tenascin, Laminin, Hyaluronan, MMP-2, TIMP-1 and MMP-9/TIMP-1 complex. Other diagnostic markers collected during anamnesis included weight, sex and age, and levels of transaminases like alanin-aminotransferase (ALT and aspartat-aminotransferase (AST).

Levels of (PIIINP), Collagen IV, Collagen VI, Tenascin, Laminin, Hyaluronan, MMP-2, TIMP-1 and MMP-9/TIMP-1 were measured by making use of sandwich immunoassays. In one embodiment, running the immunoassays of the invention comprised a reaction of two antibodies with human fluid samples, wherein the capture antibody specifically binds to one epitope of the marker. The second antibody of different epitope specificity is used to detect this complex. Preferably, the antibodies are monoclonal antibodies, although also polyclonal antibodies can be employed. Both antibodies used in the assays specifically bind to the analyte protein.

Concentration of patient diagnostic markers obtained from human fluids were measured and methods and systems were derived to assess the degree of fibrosis.

Sources or methods for making antibodies which can be used in the detection of the various serum markers are summarized as follows.

| Representative Anti-Marker Antibodies Used in the Serum Assays | | |
|---|---|---|
| Assay Reagents | Clone | Antibody Supplier/Reference |
| Collagen IV R1 | IV-4H12 | Fuji/Accession No. FERM BP-2847 (see U.S. Pat. No. 5,316,914) |
| Collagen IV R2 | T59106R | Biodesign Int'l Corp./ Biodesign Catalog #: A33125H |
| PIIINP R1 | P3P296/3/27 | Hoechst/Accession No. ECCAC 87042308 |
| PIIINP R2 | 35J23 | Bayer |

| Representative Antigen Sources | |
|---|---|
| Collagen VI | Rockland Immunochemicals Inc. (Gilbertsville, PA) (catalog no. 009-001-108) |
| Tenascin | Chemicon Int'l Inc. (Temecula, CA) (catalog no. CC065) |
| Laminin | Sigma (Catalog No. L6274) |
| Hyaluronic Acid (HA) | Bovine nasal cartilage/ Tengblad, Biochemica et Biophysica Acta, 1979, 578, 281-289. |

| Representative Nucleotide Sequences | |
|---|---|
| human TIMP1 mRNA | SEQ ID NO: 1 |
| human MMP2 mRNA | SEQ ID NO: 2 |
| human MMP9 mRNA | SEQ ID NO: 3 |

Antibody Pairs Used to Detect Serum Markers of Liver Fibrosis.

The HA assay used a specific HA binding protein (HABP) isolated from bovine nasal cartilage in accordance with the reference cited in the table above since no antibodies have been produced against HA. HA has a highly repetitive structure and the HA specific core protein can be used in a sandwich assay format. For capturing FITC-conjugated core protein and for detection, biotinylated core protein in combination with monoclonal anti-Biotin labelled with alkaline phosphatase was used.

The assay for collagen IV used a monoclonal antibody from Fuji (IV-4H12) (Accession No. FERM BP-2847) paired with a polyclonal antibody from Biodesign (T59106R) (Biodesign Catalog No.: T59106R). All assays were heterogeneous immunoassays employing a magnetic particle separation technique.

The assay for PIIINP used a Bayer monoclonal antibody deposited under the Budapest Treaty on May 24, 2004 with the American Type Culture Collection, 10801 University Boulevard, Manassas, Va. 20110-2209 paired with a monoclonal antibody from Hoechst (Accession No. ECCAC 87042308).

Antibodies for the detection of Collagen VI, Laminin, and Tenascin can be made by obtaining antigens corresponding to these sera markers from the sources listed in the table above and using such antigens as sera markers in accordance with the Hybridoma Development Protocol described in detail below.

Antibodies for the detection of TIMP-1, MMP-2, and MMP-9 can be made by: (1) producing antigens for these markers by expressing DNA sequences complementary to the marker mRNA sequences listed in the table above in accordance with the Expression of Polynucleotides protocol described in detail below; and (2) using such antigens as sera markers in accordance with the Hybridoma Development Protocol described in detail below.

Citations in the Hybridoma Development Protocol and the Expression of Polynucleotides Protocol are listed separately in the citation sections presented hereinafter.

Expression of Polynucleotides:

FIG. 5 depicts the nucleotide sequence for human TIMP1 mRNA (SEQ ID NO: 1).

FIG. 6 depicts the nucleotide sequence for human MMP2 mRNA (SEQ ID NO: 2).

FIG. 7 depicts the nucleotide sequence for human MMP9 mRNA (SEQ ID NO: 3).

To express these and other liver disease serum marker genes, the genes can be inserted into an expression vector which contains the necessary elements for the transcription and translation of the inserted coding sequence. Methods which are well known to those skilled in the art can be used to construct expression vectors containing sequences encoding liver fibrosis serum marker polypeptides and appropriate transcriptional and translational control elements. These methods include in vitro recombinant DNA techniques, synthetic techniques, and in vivo genetic recombination. Such techniques are described, for example, in Sambrook et al., (3) and in Ausubel et al., (4).

A variety of expression vector/host systems can be utilized to contain and express sequences encoding a liver disease serum marker polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those regions of the vector enhancers, promoters, 5' and 3' untranslated regions which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a "Liver fibrosis gene" polypeptide, vectors based on SV40 or EBV can be used with an appropriate selectable marker.

Bacterial and Yeast Expression Systems:

In bacterial systems, a number of expression vectors can be selected depending upon the use intended for the liver disease serum marker polypeptide. For example, when a large quantity of the liver disease serum marker polypeptide is needed for the induction of antibodies, vectors which direct high level expression of fusion proteins that are readily purified can be used. Such vectors include, but are not limited to, multifunctional E. coli cloning and expression vectors such as BLUE-SCRIPT (Stratagene). In a BLUESCRIPT vector, a sequence encoding the liver disease serum marker polypeptide can be ligated into the vector in frame with sequences for the amino terminal Met and the subsequent 7 residues of β-galactosidase so that a hybrid protein is produced. pIN vectors [Van Heeke & Schuster, (17)] or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al., (4) and Grant et al., (18).

Plant and Insect Expression Systems:

If plant expression vectors are used, the expression of sequences encoding liver disease serum marker polypeptides can be driven by any of a number of promoters. For example, viral promoters such as the 35S and 19S promoters of CaMV can be used alone or in combination with the omega leader sequence from TMV [Takamatsu, (19)]. Alternatively, plant promoters such as the small subunit of RUBISCO or heat shock promoters can be used [Coruzzi et al., (19); Broglie et al., (21); Winter et al., (22)]. These constructs can be introduced into plant cells by direct DNA transformation or by pathogen-mediated transfection. Such techniques are described in a number of generally available reviews (e.g., Hobbs or Murray, in MCGRAW HILL YEARBOOK OF SCIENCE AND TECHNOLOGY, (23)].

An insect system also can be used to express a liver disease serum marker polypeptide. For example, in one such system Autographa califomica nuclear polyhedrosis virus (AcNPV) is used as a vector to express foreign genes in Spodoptera frugiperda cells or in Trichoplusia larvae. Sequences encoding liver disease serum marker polypeptides can be cloned into a nonessential region of the virus, such as the polyhedrin gene, and placed under control of the polyhedrin promoter. Successful insertion of liver disease serum marker polypeptide will render the polyhedrin gene inactive and produce recombinant virus lacking coat protein. The recombinant viruses can then be used to infect S. frugiperda cells or Trichoplusia larvae in which liver disease serum marker polypeptides can be expressed [Engelhard et al., (24)].

Mammalian Expression Systems:

A number of viral-based expression systems can be used to express liver disease serum marker polypeptides in mammalian host cells. For example, if an adenovirus is used as an expression vector, sequences encoding liver disease serum marker polypeptides can be ligated into an adenovirus transcription/translation complex comprising the late promoter and tripartite leader sequence. Insertion in a nonessential E1 or E3 region of the viral genome can be used to obtain a viable virus which is capable of expressing a liver fibrosis serum marker polypeptides in infected host cells [Logan & Shenk, (25)]. If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding liver disease serum marker polypeptides. Such signals include the ATG initiation codon and adjacent sequences. In cases where sequences encoding a liver disease serum marker polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used [Scharf et al., (26)].

Host Cells:

A host cell strain can be chosen for its ability to modulate the expression of the inserted sequences or to process the expressed liver fibrosis serum marker polypeptide in the desired fashion. Such modifications of the polypeptide include, but are not limited to, acetylation, carboxylation, glycosylation, phosphorylation, lipidation, and acylation. Posttranslational processing which cleaves a "prepro" form of the polypeptide also can be used to facilitate correct insertion, folding and/or function. Different host cells which have specific cellular machinery and characteristic mechanisms for Post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express liver disease serum marker polypeptides can be transformed using expression vectors which can contain viral origins of replication and/or endogenous expression elements and a selectable marker gene on the same or on a separate vector. Following the introduction of the vector, cells can be allowed to grow for 12 days in an enriched medium before they are switched to a selective medium. The purpose of the selectable marker is to confer resistance to selection, and its presence allows growth and recovery of cells which successfully express the introduced liver fibrosis serum marker polypeptide gene sequences. Resistant clones of stably transformed cells can be proliferated using tissue culture techniques appropriate to the cell type. See, for example, R.I. Freshney, (27).

Any number of selection systems can be used to recover transformed cell lines. These include, but are not limited to, the herpes simplex virus thymidine kinase (Wigler et al., (28)] and adenine phosphoribosyltransferase [Lowy et al., (29)] genes which can be employed in $tk^-$ or $aprt^-$ cells, respectively. Also, antimetabolite, antibiotic, or herbicide resistance can be used as the basis for selection. For example, dhfr confers resistance to methotrexate [Wigler et al., (30)], npt confers resistance to the aminoglycosides, neomycin and G418 [Colbere-Garapin et al., (31)], and als and pat confer resistance to chlorsulfuron and phosphinotricin acetyltransferase, respectively. Additional selectable genes have been described. For example, trpB allows cells to utilize indole in place of tryptophan, or hisD, which allows cells to utilize histinol in place of histidine [Hartman & Mulligan, (32)]. Visible markers such as anthocyanins, β-glucuronidase and its substrate GUS, and luciferase and its substrate luciferin, can be used to identify transformants and to quantify the amount of transient or stable protein expression attributable to a specific vector system [Rhodes et al., (33)].

Detecting Expression and Gene Product:

Although the presence of marker gene expression suggests that the liver disease serum marker polypeptide gene is also present, its presence and expression may need to be confirmed. For example, if a sequence encoding a liver disease serum marker polypeptide is inserted within a marker gene sequence, transformed cells containing sequences which encode a liver disease serum marker polypeptide can be identified by the absence of marker gene function. Alternatively, a marker gene can be placed in tandem with a sequence encoding a liver fibrosis serum marker polypeptide under the control of a single promoter. Expression of the marker gene in response to induction or selection usually indicates expression of the liver fibrosis serum marker polypeptide.

Alternatively, host cells which contain a liver disease serum marker polypeptides and which express a liver fibrosis serum marker polypeptide can be identified by a variety of procedures known to those of skill in the art. These procedures include, but are not limited to, DNA-DNA or DNA-RNA hybridization and protein bioassay or immunoassay techniques which include membrane, solution, or chip-based technologies for the detection and/or quantification of nucleic acid or protein. For example, the presence of a polynucleotide sequence encoding a liver disease serum marker polypeptide can be detected by DNA-DNA or DNA-RNA hybridization or amplification using probes or fragments or fragments of polynucleotides encoding a liver disease serum marker polypeptide. Nucleic acid amplification-based assays involve the use of oligonucleotides selected from sequences encoding a liver fibrosis serum marker polypeptide to detect transformants which contain a liver fibrosis serum marker polypeptide.

A variety of protocols for detecting and measuring the expression of a liver fibrosis serum marker polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a liver disease serum marker polypeptide can be used, or a competitive binding assay can be employed. These and other assays are described in Hampton et al., (34) and Maddox et al., (35).

A wide variety of labels and conjugation techniques are known by those skilled in the art and can be used in various nucleic acid and amino acid assays. Means for producing labeled hybridization or PCR probes for detecting sequences related to poly-nucleotides encoding liver fibrosis serum marker polypeptides include oligo labeling, nick translation, end-labeling, or PCR amplification using a labeled nucleotide. Alternatively, sequences encoding a liver disease serum marker polypeptide can be cloned into a vector for the production of an MRNA probe. Such vectors are known in the art, are commercially available, and can be used to synthesise RNA probes in vitro by addition of labelled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides:

Host cells transformed with nucleotide sequences encoding a liver disease serum marker polypeptide can be cultured under conditions suitable for the expression and recovery of the protein from cell culture. The polypeptide produced by a transformed cell can be secreted or stored intracellular depending on the sequence and/or the vector used. As will be understood by those of skill in the art, expression vectors containing polynucleotides which encode liver fibrosis serum marker polypeptides can be designed to contain signal sequences which direct secretion of soluble liver fibrosis serum marker polypeptides through a prokaryotic or eukaryotic cell membrane or which direct the membrane insertion of membrane-bound liver fibrosis serum marker polypeptides.

As discussed above, other constructions can be used to join a sequence encoding a liver disease serum marker polypeptides to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the liver disease serum marker polypeptide also can be used to facilitate purification. One such expression vector provides for expression of a fusion protein containing a liver disease serum marker polypeptide and 6 histidine residues preceding a thioredoxin or an enterokinase cleavage site. The histidine residues facilitate purification by IMAC (immobilized metal ion affinity chromatography, as described in Porath et al., (36), while the enterokinase cleavage site provides a means for purifying the "Liver fibrosis gene" polypeptide from the fusion protein. Vectors which contain fusion proteins are disclosed in Kroll et al., (37).

Chemical Synthesis:

Sequences encoding a liver disease serum marker polypeptide can be synthesized, in whole or in part, using chemical methods well known in the art (see Caruthers et al., (38) and Horn et al., (39). Alternatively, a liver disease serum marker polypeptide itself can be produced using chemical methods to synthesize its amino acid sequence, such as by direct peptide synthesis using solid-phase techniques [Merrifield, (40) and Roberge et al., (41)]. Protein synthesis can be performed using manual techniques or by automation. Automated synthesis can be achieved, for example, using Applied Biosystems 431A Peptide Synthesizer (Perkin Elmer). Optionally, fragments of liver fibrosis serum marker polypeptides can be separately synthesized and combined using chemical methods to produce a full-length molecule.

The newly synthesized peptide can be substantially purified by preparative high performance liquid chromatography [Creighton, (42)]. The composition of a synthetic liver disease serum marker polypeptide can be confirmed by amino acid analysis or sequencing (e.g., the Edman degradation procedure; see Creighton, (42). Additionally, any portion of the amino acid sequence of the liver disease serum marker polypeptide can be altered during direct synthesis and/or combined using chemical methods with sequences from other proteins to produce a variant polypeptide or a fusion protein.

Hybridoma Development Protocol

Phase I: Immunization.

BALB/c mice and Swiss Webster mice (five per group) are immunized intraperitoneally with one of the above-identified liver disease sera markers (different doses) emulsified with complete Freund's adjuvant (CFA) followed by three boosts (at two weeks interval) with immunogen emulsified with incomplete Freund's adjuvant. Mice are bled one week after each boost and sera titrated against the immunogen in ELISA. The mouse with the highest titer is selected for fusion.

Phase II: Cell Fusion and Hybridoma Selection.

The mouse selected for fusion is boosted with the same dose of antigen used in previous immunizations. The boost is given four days prior to splenectomy and cell fusion. The antigen preparation is given intraperitoneally without adjuvant.

On the day of fusion the mouse is sacrificed and the spleen is removed aseptically. The spleen is minced using forceps and strained through a sieve. The cells are washed twice using Iscove's modified Eagle's media (IMDM) and are counted using a hemacytometer.

The mouse myeloma cell line P3×63Ag8.653 is removed from static, log-phase culture, washed with IMDM and counted using a hemacytometer.

Myeloma and spleen cells are mixed in a 1:5 ratio and centrifuged. The supernatant is discarded. The cell pellet is gently resuspended by tapping the bottom of the tube. One milliliter of a 50% solution of PEG (MW 1450) is added drop by drop over a period of 30 seconds. The pellet is mixed gently for 30 seconds using a pipette. The resulting cell suspension is allowed to stand undisturbed for another 30 seconds. Five milliliters of IMDM is added over a period of 90 seconds followed by another 5 ml immediately. The resulting cell suspension is left undisturbed for 5 minutes. The cell suspension is spun and the pellet resuspended in HAT medium (IMDM containing 10% FBS, 2 mM L-glutamine, 0.6% 2-mercaptoethanol (0.04% solution), hypoxanthine, aminopterin, thymidine, and 10% Origen growth factor). The cells are resuspended to 5E5 cells per milliliter. Cells are plated into 96-well plates. Two hundred microliters or 2E5 cells are added to each well.

Plates are incubated at 37° C. in a 7% $CO_2$ atmosphere with 100% humidity. Seven days after fusion, the media is removed and replaced with IMDM containing 10% FBS, 2 mM L-glutamine, 0.6% 2-mercaptoethanol stock (0.04%), hypoxanthine and thymidine. Typically, growing colonies of hybridomas are seen microscopically about seven days after the fusion. These colonies can be seen with the naked eye approximately 10-14 days after fusion.

Ten to fourteen days after fusion, the supernatant is taken from wells with growing hybridoma colonies. The volume of supernatant is approximately 150-200 microliters and contains 10-100 micrograms of antibody per milliliter. This supernatant is tested for specific antibody using the same assay(s) used to screen the sera. Positive hybridoma colonies are moved from the 96-well plate to a 24-well plate. Three to five days later, the supernatant from 24-well plate is tested to confirm the presence of specific antibody. The volume of supernatant from one well of a 24-well plate is approximately 2 mL and contains 10-100 micrograms/mL of antibody. Cells from positive wells are expanded in T-25 and T-75 flasks. Cells are frozen from T-75 flasks.

Cells from positive wells are also cloned by limiting dilution. Hybridoma cells are plated onto 96-well plates at a density of 0.25 cells per well or one cell in every fourth well. Growing colonies are tested 10-14 days later using the same assay(s) used to initially select the hybridomas. Positive clones are expanded and frozen.

Phase III: Production.

Hybridoma cells expanded to T-162 flasks followed by transferring these to roller bottles for production of cell supernatant. The cells are grown in roller bottles for about two weeks until the cells are less than 10% viable. The culture supernatant is harvested from these roller bottles for purification.

Brief description of Immunoassays.

All antibodies are heterogenous ELISA-type assays formatted for the Bayer Immuno 1 system. The system employs fluorescein-labeled capture antibodies (denoted R1) and alkaline phosphatase labled tag antibodies (denoted R2). The antibody conjugates are dissolved in a physiological buffer at a concentration between 2 and 50 mg/L. The immunoreactive reagents are incubated with a fixed amount of patient sample containing the antigen to be assayed. The patient sample is always pipetted first into a reaction cuvette followed by R1 thirty seconds later. R2 is normally added 30 seconds to 20 minutes after the R1 addition. The mixture is incubated for a maximum of 20 minutes although other embodiments of the immunoassays might require longer of shorter incubation times. Subsequently, immunomagnetic particles are added to the mixture. The particles consist of iron oxide containing polyacrylamide beads with anti-fluorescein antibodies conjugated to the particle surface. The particles are commercially available from Bayer HealthCare Diagnostics.

Upon incubation of the immunomagnetic particles with the sandwich immuno complex formed from the antigen and the R1 and R2 conjugates, the sandwich immuno complex is captured through the fluorescein label of the R1 antibody by the anti-fluorescein antibodies on the immuno magnetic particles. The super-complex formed is precipitated by an external magnetic field. All unbound material, especially R2 alkaline phosphatate conjugate is removed by washing. The washed complex is then resuspended in p-nitrophenolphosphate solution. The rate of color formation is proportional to the amount of phosphatase left in the cuvette which is proportional to the amount of antigen. Quantification is achieved by recording a six-point calibration curve and a calibration curve, constructed by a cubic regression or a Rodbard fit.

(a) Assay Performance.

The performance of each of the assays was determined in isolation. The sensitivity and specificity, inter and intra-assay variation, interferences, linearity and parallelism were determined for each immunoassay. All assays were shown to meet high clinical chemistry standards. The ranges of results obtained for healthy subjects of both sexes and a range of ages from 18 to 75 years were determined to establish "normal" values. The assays were applied to subjects with a range of pathological disorders.

(b) Statistical Background.

An observational study of liver fibrosis in 1,021 subjects ("European Liver Fibrosis" or "ELF" Study) was undertaken and resultant data were analyzed. Liver fibrosis scoring systems employed were the Scheuer Score (0-4),
the Modified Ishak Score (HAI) A—Interface Hepatitis (0-4),
the Modified Ishak Score (HAI) B—Confluent Necrosis (0-6),
the Modified Ishak Score (HAI) C—Spotty Necrosis (0-4),
the Modified Ishak Score (HAI) D—Portal Inflammation (0-4),
the Modified HAI Score (Ishak Score) (0-6).

A stepwise discriminant analysis was applied; the following functions of serum parameters are shown in Table 1 to have had a major impact on the corresponding scoring type.

TABLE 1

| Scoring Type | Surrogate Parameters | | |
|---|---|---|---|
| Scheuer Score: | ln(TIMP-1) | ln(Collagen VI/Hyaluronan) | ln(Hyaluronan/Laminin) |
| Modified Ishak Score A - Interface Hepatitis: | ln(TIMP-1) | ln(Collagen VI/Hyaluronan) | ln(Collagen VI/Tenascin) |
| Modified Ishak Score B - Confluent Necrosis: | ln(Hyaluronan) | ln(Collagen VI/MMP-2) | |
| Modified Ishak Score C - Spotty Necrosis: | ln (Hyaluronan) | ln(MMP-9/TIMP-1/complex Tenascin) | |
| Modified Ishak Score D - Portal Inflammation: | ln(Laminin) | ln(Collagen VI/TIMP-1) | |
| Modified Ishak Score - Stage: | ln(TIMP-1) | ln(Collagen VI/Hyaluronan) | ln (Hyaluronan/Laminin) |

A corresponding discriminant analysis yielded the linear discriminating functions which were used for calculation and prediction of biopsy score. The algorithms derived can be applied to every known scoring system (e.g. Scheuer Score, Ishak Score, Metavir Score, Ludwig Score, HAI Score). For example, the algorithms can be used to predict the biopsy score of a patient (e.g. score 0, 1, 2, 3, . . . ) or to predict a group of scores (category) a patient belongs to (e.g. mild fibrosis; score 0 to 1).

Discriminating functions used included combinations of markers from the list of N-terminal procollagen III propeptide (PIIINP), Collagen IV, Collagen VI, Tenascin, Laminin, Hyaluronan, MMP-2, TIMP-1 and MMP-9/TIMP-1 complex as well as age, sex and transaminase levels, most notably ALT (alanine amino transferase), AST (aspartate amino transferase) and GLDH (glutamate dehydrogenase), of the patient together with numerical factors, namely multiplicators and summands or combinations thereof, with these numerical factors having values between −1000 and +1000 nanograms/ml (ng/ml).

Values provided herein are, unless otherwise indicated, in units of nanograms/milliliter (ng/ml). Those of skill in the art can readily convert such values to any other useful units and modify the values used in the algorithms disclosed herein accordingly.

Predicting the biopsy scores identified using different scoring systems required development of different algorithms employing a different combination of the markers PIIINP, Collagen IV, Collagen VI, Tenascin, Laminin, Hyaluronan, MMP-2, TIMP-1 and MMP-9/TIMP-1 complex with age, sex and transaminase values combined with different numerical factors.

Discriminant functions are either set up as an array of as many different functions as there are histopathological scores to compare with (see algorithms 1, 2, 3, 4, 5, 6, 1b, 2b, 3b, 4b, 5b, 6b), or as one single discriminant function, often also called logistic regression (see algorithms 4a, 5a, 6a, 4c, 5c, 6c, 7, 7a, 8, 8a 9, 10, 11, 12). While discriminant functions intrins computed biomarker derived liver score, logistic regressions need one or multiple cut-off values, depending on their use as a tool to assess binary outcomes or as a tool to compute a marker score. In order to yield a marker score the discriminant function requires as many different cutoff values as there are disease grades reduced by one.

In order to compute a histopathology score, the results of the individual serum markers or other parameters have to be put in each of the equations to calculate the discriminant scores. In case of models employing a set of several discriminant functions, each function represents a different score. The function yielding the highest numerical discriminant score upon computation with the values put in, will result in its associated disease score as the biomarker derived calculated liver disease score.

(c) Algorithms for Scheuer Score.

The following algorithms 1 to 6 and 4a to 6a were calculated by correlating biopsies assessed by the Scheuer scoring system and serum marker concentrations of a group of patients with liver diseases. All algorithms were derived using marker results and pathology scores from one group of patients (marker finding cohort) and then used to predict biopsy scores (the calculated scores) in a separate group of patients (the validation cohort). The calculated scores were compared with scores determined by a single pathologist (case B), with a consensus score of three pathologists (case C) and with the range covered by all pathologists (case A). Kappa values were computed to assess the power of the algorithm. In order to be able to use the criteria normally used to assess the power of new diagnostics methods (sensitivity, specificity, positive predictive value (PPV), negative predictive value (NPV) and the area under the curve in a receiver operator characteristics analysis (ROC AUC), the liver disease scores derived from the histological analysis and the calculated scores derived from the serum marker algorithm were dichtomized calling a score 0 to 1 a negative reading and a score 2 to 4 a positive reading (Scheuer Score). Accordingly the concordance of both methods in terms of true positives, true negatives, false negatives and false positives could be assessed yielding the sensitivity, specificity, NPV, PPV and ROC AUC of each of the algorithm. See Algorithms 4a, 5a, 6a. In all instances the biopsy results were used as the gold standard to assess each different algorithm.

| Abbreviations used in Algorithms: | |
|---|---|
| Abbreviation | Marker |
| Col IV or COL_IV: | Collagen type IV |
| Col VI or COL_VI: | Collagen type VI |
| Hya or HYA or HA: | Hyaluronic Acid |
| TIMP-1 or TIMP1: | Tissue Inhibitor of Melloproteinases type 1 |
| Lam or LAM: | Laminin |
| PIIINP: | Aminoterminal Propeptide of Procollagen type III |
| MMP2: | Matrix Metalloproteinases type 2 |
| MMP9 or MMP9/TIMP1: | Matrix Metalloproteinases type 9 (MMP9); and MMP9 complexed with TIMP-1 (MMP9/TIMP1). |
| Ten or TEN: | Tenascin |
| CRATIO: | The analytical value [ng/mL] of Collagen type IV divided by the analytical value of Collagen type VI. |

Algorithm 1: (employing Col VI with Hyaluronic Acid, Laminin and TIMP-1)

[0]   −108.861+0.283*LOG(COL_VI/HYAL)−1.050*LOG(HYAL/LAM)+35.372*LOG(TIMP1)
[1]   −114.231+0.195*LOG(COL_VI/HYAL)−0.654*LOG(HYAL/LAM)+36.158*LOG(TIMP1)
[2]   −120.649−0.998*LOG(COL_VI/HYAL)−2.102*LOG(HYAL/LAM)+36.925*LOG(TIMP1)
[3]   −123.672−1.281*LOG(COL_VI/HYAL)−1.344*LOG(HYAL/LAM)+37.163*LOG(TIMP1)
[4]   −133.207−2.186*LOG(COL_VI/HYAL)−1.602*LOG(HYAL/LAM)+38.188*LOG(TIMP1)

Algorithm 2: (employing Col VI with Hyaluronic Acid, Laminin, TIMP-1)

[0]   −75.18797+23.04542*LOG(TIMP1)−0.583641*LOG(COL_VI/HYAL)−0.140956*LOG(HYAL/LAM)
[1]   −76.1526+23.15895*LOG(TIMP1)−0.963402*LOG(COL_VI/HYAL)−0.009472*LOG(HYAL/LAM)
[2]   −78.62662+23.32161*LOG(TIMP1)−1.227332*LOG(COL_VI/HYAL)−0.067969*LOG(HYAL/LAM)
[3]   −83.09285+23.64493*LOG(TIMP1)−2.181493*LOG(COL_VI/HYAL)−0.300241*LOG(HYAL/LAM)
[4]   −93.89732+24.86246*LOG(T1MP1)−2.841299*LOG(COL_VI/HYAL)−0.136885*LOG(HYAL/LAM)

Algorithm 3: (employing Col VI with Hyaluronic Acid, Col IV and PIIINP)

[0]   −95.39661+17.66025*LOG(HYAL)−0.820836*LOG(COL_IV)+0.245778*LOG(COL_VI/PIIINP)−
      17.79663*LOG(COL_VI/TIMP1)−14.96754*LOG(HYAL/MMP2)−0.279356*LOG(LAM/MMP9T)
[1]   −95.84457+17.62365*LOG(HYAL)−0.667854*LOG(COL_IV)+0.155707*LOG(COL_VI/PIIINP)−
      18.0407*LOG(COL_VI/TIMP1)−14.42688*LOG(HYAL/MMP2)−0.554323*LOG(LAM/MMP9T)
[2]   −99.13575+17.76656*LOG(HYAL)−0.978731*LOG(COL_IV)−0.12995*LOG(COL_VI/PIIINP)−
      18.69948*LOG(COL_VI/TIMP1)−14.49353*LOG(HYAL/MMP2)−0.647247*LOG(LAM/MMP9T)
[3]   −104.4554+18.38886*LOG(HYAL)−0.202832*LOG(COL_IV)−0.157058*LOG(COL_VI/PIIINP)−
      18.70409*LOG(COL_VI/TIMP1)−14.49716*LOG(HYAL/MMP2)−0.340197*LOG(LAM/MMP9T)
[4]   −119.8887+20.14719*LOG(HYAL)+0.959792*LOG(COL_IV)−0.80876*LOG(COL_VI/PIIINP)−
      18.69873*LOG(COL_VI/TIMP1)−15.57103*LOG(HYAL/MMP2)−0.229757*LOG(LAM/MMP9T)

-continued

Algorithm 4 (employing Col VI with Hyaluronic Acid, Laminin and TIMP-1)

[0]  −84.8884+1.314094*LOG(COL_VI/HYAL)+2.163728*LOG(HYAL/LAM)+26.86543*LOG(TIMP1)
[1]  −87.1291+1.152303*LOG(COL_VI/HYAL)+2.507536*LOG(HYAL/LAM)+27.13607*LOG(TIMP1)
[2]  −89.7304+0.766894*LOG(COL_VI/HYAL)+2.361471*LOG(HYAL/LAM)+27.43159*LOG(TIMP1)
[3]  −94.3078−0.074816*LOG(COL_VI/HYAL)+2.251909*LOG(HYAL/LAM)+27.81493*LOG(TIMP1)
[4]  −104.774−1.087963*LOG(COL_VI/HYAL)+2.110437*LOG(HYAL/LAM)+28.88894*LOG(TIMP1)

Algorithm 4a (binary Algorithm employing Col VI with Hyaluronic Acid, Laminin and TIMP-1)

Logit  −8.33001−1.104523*LOG(COL_VI/HYAL)−0.127521*LOG(HYAL/LAM)+0.841806*LOG(TIMP1)

Algorithm 5 (employing Col VI with Hyaluronic Acid, Col IV, PIIINP, MMP2)

[0]  −510.728+22.96526*(LOG(HYAL))−66.83994*(LOG(COL_IV))−114.5438*(LOG(COL_VI)/LOG
     (HYAL))−8.772354*(LOG(PIIINP))+29.61084*(LOG(COL_IV)/LOG(HYAL))+155.1575*(LOG
     (MMP2))+523.6594*(LOG(COL_IV)/LOG(MMP2))−184.6677*(LOG(HYAL)/LOG(MMP2))
[1]  −507.105+21.13922*(LOG(HYAL))−64.02849*(LOG(COL_IV))−116.0789*(LOG(COL_VI)/LOG
     (HYAL))−8.710835*(LOG(PIIINP))+28.83564*(LOG(COL_IV)/LOG(HYAL))+154.0848*(LOG
     (MMP2))+513.7398*(LOG(COL_IV)/LOG(MMP2))−174.771*(LOG(HYAL)/LOG(MMP2))
[2]  −517.258+21.9922*(LOG(HYAL))−67.10076*(LOG(COL_IV))−122.2884*(LOG(COL_VI)/LOG
     (HYAL))−7.559512*(LOG(PIIINP))+30.00615*(LOG(COL_IV)/LOG(HYAL))+156.4279*(LOG
     (MMP2))+527.1177*(LOG(COL_IV)/LOG(MMP2))−182.0914*(LOG(HYAL)/LOG(MMP2))
[3]  −521.186+17.72648*(LOG(HYAL))−61.20226*(LOG(COL_IV))−120.3493*(LOG(COL_VI)/LOG
     (HYAL))−7.928957*(LOG(PIIINP))+30.4852*(LOG(COL_IV)/LOG(HYAL))+155.6176*(LOG
     (MMP2))+493.4266*(LOG(COL_IV)/LOG(MMP2))−146.0582*(LOG(HYAL)/LOG(MMP2))
[4]  −562.9+30.0182*(LOG(HYAL))−71.36396*(LOG(COL_IV))−124.3929*(LOG(COL_VI)/LOG
     (HYAL))−7.39815*(LOG(PIIINP))+31.28702*(LOG(COL_IV)/LOG(HYAL))+160.534*(LOG
     (MMP2))+566.915*(LOG(COL_IV)/LOG(MMP2))−223.449*(LOG(HYAL)/LOG(MMP2))

Algorithm 5a (binary Algorithm employing Col VI with Hyaluronic Acid, Col IV, PIIINP, MMP2)

Logit  −19.3878+2.217337*(LOG(HYAL))−2.493531*(LOG(COL_IV))−
       6.686058*(LOG(COL_VI)/LOG(HYAL))+1.04518*(LOG(PIIINP))+1.356867*(LOG(COL_IV)/LOG
       (HYAL))+2.546269*(LOG(MMP2))+16.17252*(LOG(COL_IV)/LOG(MMP2))−11.51533*(LOG
       (HYAL)/LOG(MMP2))

Algorithm 6 (employing Hyaluronic Acid with Col IV, PIIINP, TIMP-1)

[0]  −139.611−0.550172*(LOG(HYAL))+31.12324*(LOG(COL_IV))−17.36457*(LOG(PIIINP))+
     24.38884*(LOG(TIMP1))
[1]  −142.886−0.287819*(LOG(HYAL))+31.77958*(LOG(COL_IV))−17.39204*(LOG(PIIINP))+
     24.28051*(LOG(TIMP1))
[2]  −141.391−0.36426*(LOG(HYAL))+30.81993*(LOG(COL_IV))−16.4064*(LOG(PIIINP))+
     24.5837*(LOG(TIMP1))
[3]  −148.365+0.453879*(LOG(HYAL))+31.74657*(LOG(COL_IV))−16.61532*(LOG(PIIINP))+
     24.50483*(LOG(TIMP1))
[4]  −164.746+1.023888*(LOG(HYAL))+33.94289*(LOG(COL_IV))−16.35512*(LOG(PIIINP))+
     24.66699*(LOG(TIMP1))

Algorithm 6a (binary outcome employing Hyaluronic Acid with Col IV, PIIINP, TIMP-1)

Logit  −19.3878+2.217337*(LOG(HYAL))−2.493531*(LOG(COL_IV))−6.686058*(LOG(COL_VI)/
       LOG(HYAL))+1.04518*(LOG(PIIINP))+1.356867*(LOG(COL_IV)/LOG(HYAL))+2.546269*(LOG
       (MMP2))+16.17252*(LOG(COL_IV)/LOG(MMP2))−11.51533*(LOG(HYAL)/LOG(MMP2))

Table 2 below shows the diagnostic performance of algorithms 1, 2 and 3. Column C reports the results of the comparisons between a consensus score of three pathologists and the marker based results for a given algorithm; column A reports the results of the comparisons between a range of scores reported by three different pathologists and the marker based results; column B reports the results of the comparisons between a score reported by a studies central pathologists (single pathologist) and the marker based results. Hit rate is the percentage of scores reported to be identical by the marker based algorithm and the pathologist's Scheurer score; The Kappa value reports agreements between the groups of results, L_Kappa and U_Kappa gives the lower and upper limit of confidence for the Kappa value (95% CI), NPV is the negative predictive value for a dichotomized scoring system, PPV is the positive predictive value for a dichotomized system.

Table 3 shows the diagnostic performance of algorithm 4, 5 and 6. Column C reports the results of the comparisons between a consensus score of three pathologists and the marker based results for a given algorithm; column A reports the results of the comparisons between a range of scores reported by three different pathologists and the marker based results; column B reports the results of the comparisons between a score reported by a studies central pathologists (single pathologist) and the marker based results; Hit rate is the percentage of scores reported to be identical by the marker based algorithm and the pathologist's Scheurer score; The Kappa value reports agreements between the groups of results, L_Kappa and U_Kappa gives the lower and upper limit of confidence for the Kappa value (95% CI), NPV is the negative predictive value for a dichotomized scoring system, PPV is the positive predictive value for a dichotomized system.

TABLE 2

|  | Algorithm 1 | | | Algorithm 2 | | | Algorithm 3 | | |
| --- | --- | --- | --- | --- | --- | --- | --- | --- | --- |
|  | C | A | B | C | A | B | C | A | B |
| Hit-Rate (%) [0] | 33.3 | 38.9 | 35.0 | 17.1 | 40.0 | 13.7 | 20.0 | 41.4 | 16.8 |
| Hit-Rate (%) [1] | 36.8 | 42.7 | 36.0 | 80.7 | 81.6 | 75.8 | 74.6 | 77.2 | 71.7 |
| Hit-Rate (%) [2] | 25.8 | 42.4 | 19.0 | 0.0 | 36.8 | 0.0 | 0.0 | 34.2 | 5.1 |
| Hit-Rate (%) [3] | 26.1 | 34.8 | 22.2 | 6.4 | 17.0 | 5.2 | 12.8 | 21.3 | 9.3 |
| Hit-Rate (%) [4] | 63.0 | 63.0 | 55.9 | 62.5 | 62.5 | 52.9 | 43.8 | 43.8 | 47.1 |
| Hit-Rate (%) All | 35.9 | 42.9 | 33.8 | 42.2 | 54.2 | 36.7 | 39.5 | 51.2 | 36.7 |
| N | 468 | 468 | 793 | 301 | 301 | 626 | 301 | 301 | 626 |
| Kappa | 0.175 | 0.268 | 0.151 | — | 0.199 | — | 0.124 | 0.310 | 0.121 |
| L_Kappa | 0.119 | 0.211 | 0.109 | — | 0.134 | — | 0.056 | 0.235 | 0.077 |
| U_Kappa | 0.231 | 0.325 | 0.192 | — | 0.265 | — | 0.191 | 0.385 | 0.165 |
| P(Kappa = 0) | <0.0001 | <0.0001 | <0.0001 | — | <0.0001 | — | <0.0001 | <0.0001 | <0.0001 |
| NPV (%) [0-1] | 61.6 | 63.8 | 62.8 | 91.8 | 92.4 | 85.5 | 88.0 | 89.1 | 81.6 |
| PPV (%) [2-4] | 66.1 | 75.1 | 66.3 | 31.6 | 46.2 | 35.4 | 35.0 | 48.7 | 39.0 |
| Hit-Rate (%) All | 63.5 | 68.4 | 64.2 | 68.4 | 74.4 | 65.8 | 67.4 | 73.4 | 64.9 |
| Kappa | 0.268 | 0.372 | 0.280 | 0.261 | 0.417 | 0.226 | 0.252 | 0.404 | 0.219 |
| L_Kappa | 0.182 | 0.291 | 0.214 | 0.160 | 0.315 | 0.152 | 0.146 | 0.299 | 0.142 |
| U_Kappa | 0.354 | 0.454 | 0.346 | 0.363 | 0.520 | 0.300 | 0.358 | 0.508 | 0.295 |
| P(Kappa = 0) | <0.0001 | <0.0001 | <0.0001 | <0.0001 | <0.0001 | <0.0001 | <0.0001 | <0.0001 | <0.0001 |
| Sensitivity | 0.539 | 0.584 | 0.540 | 0.712 | 0.794 | 0.613 | 0.651 | 0.740 | 0.578 |
| Specificity | 0.729 | 0.791 | 0.739 | 0.679 | 0.730 | 0.671 | 0.681 | 0.732 | 0.674 |

TABLE 3

|  | C Alg. 4 | C Alg. 5 | C Alg. 6 | B Alg. 4 | B Alg. 5 | B Alg. 6 | A Alg. 4 | A Alg 5 | A Alg 6 |
| --- | --- | --- | --- | --- | --- | --- | --- | --- | --- |
| Hit-Rate (%) All | 32.8 | 36.1 | 34.4 | 35.8 | 35.5 | 34.3 | 43.1 | 45.8 | 44.1 |
| Hit-Rate (%) [0] | 53.6 | 43.5 | 47.8 | 52.3 | 43.2 | 45.8 | 62.2 | 50.7 | 56.7 |
| Hit-Rate (%) [1] | 18.6 | 35.4 | 33.6 | 24.9 | 30.6 | 27.8 | 27.9 | 43.4 | 42.1 |
| Hit-Rate (%) [2] | 15.8 | 13.2 | 15.8 | 18.2 | 20.8 | 20.8 | 29.4 | 35.9 | 35.7 |
| Hit-Rate (%) [3] | 27.7 | 38.3 | 25.5 | 31.9 | 36.3 | 29.7 | 37.8 | 50.0 | 34.1 |
| Hit-Rate (%) [4] | 65.6 | 46.9 | 43.8 | 57.4 | 48.5 | 50.0 | 71.4 | 50.0 | 48.6 |
| N | 299 | 299 | 299 | 600 | 600 | 600 | 299 | 299 | 299 |
| Kappa | 0.146 | 0.176 | 0.154 | 0.174 | 0.176 | 0.164 | 0.274 | 0.302 | 0.280 |
| L_Kappa | 0.079 | 0.107 | 0.086 | 0.125 | 0.127 | 0.116 | 0.204 | 0.230 | 0.209 |
| U_Kappa | 0.213 | 0.246 | 0.223 | 0.223 | 0.225 | 0.212 | 0.344 | 0.374 | 0.351 |
| P(Kappa = 0) | <0.0001 | <0.0001 | <0.0001 | <0.0001 | <0.0001 | <0.0001 | <0.0001 | <0.0001 | <0.0001 |
| Binary Outcome: | Alg 4b | Alg 5b | Alg 6b | Alg 4b | Alg 5b | Alg 6b | Alg 4b | Alg 5b | Alg 6b |
| PPV (%) [2-4] | 57.1 | 55.8 | 55.7 | 61.5 | 57.1 | 55.8 | 59.4 | 57.8 | 58.6 |
| NPV (%) [0-1] | 75.3 | 77.0 | 75.5 | 77.3 | 78.8 | 77.4 | 78.9 | 80.3 | 77.4 |
| Hit-Rate (%) All | 67.2 | 66.6 | 66.2 | 70.5 | 67.8 | 66.5 | 70.2 | 69.2 | 68.6 |
| Kappa | 0.328 | 0.329 | 0.315 | 0.391 | 0.358 | 0.331 | 0.389 | 0.382 | 0.363 |
| L_Kappa | 0.221 | 0.224 | 0.208 | 0.317 | 0.285 | 0.258 | 0.284 | 0.280 | 0.258 |
| U_Kappa | 0.436 | 0.434 | 0.422 | 0.466 | 0.431 | 0.405 | 0.493 | 0.485 | 0.468 |
| P(Kappa = 0) | <0.0001 | <0.0001 | <0.0001 | <0.0001 | <0.0001 | <0.0001 | <0.0001 | <0.0001 | <0.0001 |
| Sensitivity | 65.0 | 70.1 | 66.7 | 66.9 | 73.3 | 71.6 | 69.3 | 73.9 | 69.5 |
| Specificity | 68.7 | 64.3 | 65.9 | 72.8 | 64.3 | 63.2 | 70.8 | 66.3 | 68.0 |
| N(AUC) | 299 | 299 | 299 | 600 | 600 | 600 | 299 | 299 | 299 |
| AUC(ROC) | 0.748 | 0.756 | 0.768 | 0.765 | 0.765 | 0.771 | 0.839 | 0.846 | 0.860 |

(d) Algorithms for Ishak Score.

The following algorithms 1b, 2b, 3b, 4b, 5b, 6b, 4c, 5c and 6c were calculated by correlating biopsies assessed by the Ishak scoring system and serum marker concentrations of a group of patients with liver diseases:

All algorithms were derived using marker results and pathology scores from one group of patients (marker finding cohort) and then used to predict biopsy scores (the calculated scores) in a separate group of patients (the validation cohort). The calculated scores were compared with scores determined by a single pathologist (case B), with a consensus score of 3 pathologists (case C) and with the range covered by all pathologists (case A). Kappa values were computed to assess the power of the algorithm.

In order to be able to use the criteria normally used to assess the power of new diagnostics methods (sensitivity, specificity, positive predictive value (PPV), negative predictive value (NPV), and the area under the curve in a receiver operator characteristics analysis, the liver disease scores derived from the histological analysis and the calculated scores derived from the serum marker algorithm were dichotomized calling a score 0 to 2 a negative reading and a score 3 to 6 a positive reading (Ishak Score). Accordingly the concordance of both methods in terms of true positives, true negatives, false negatives and false positives could be assessed yielding the sensitivity, specificity, NPV, PPV and ROC AUC of each of the algorithm. See Algorithms 4a, 5a, 6a. In all instances the biopsy results were used as the gold standard to assess each different algorithm.

Algorithm 1b: (employing Col VI with Hyaluronic Acid, Laminin and TIMP-1)

[0]: −107.752−0.347*LOG(COL_VI/HYAL)−1.493*LOG(HYAL/LAM)+34.879*LOG(TIMP1)
[1]: −112.550−0.301*LOG(COL_VI/HYAL)−1.086*LOG(HYAL/LAM)+35.617*LOG(TIMP1)
[2]: −114.626−0.760*LOG(COL_VI/HYAL)−1.270*LOG(HYAL/LAM)+35.819*LOG(TIMP1)
[3]: −121.339−2.065*LOG(COL_VI/HYAL)−2.910*LOG(HYAL/LAM)+36.593*LOG(TIMP1)
[4]: −119.289−1.009*LOG(COL_VI/HYAL)−1.271*LOG(HYAL/LAM)+36.449*LOG(TIMP1)
[5]: −125.551−2.966*LOG(COL_VI/HYAL)−2.536*LOG(HYAL/LAM)+36.797*LOG(TIMP1)
[6]: −133.055−3.256*LOG(COL_VI/HYAL)−2.329*LOG(HYAL/LAM)+37.695*LOG(TIMP1)

Algorithm 2b: (employing Col VI with Hyaluronic Acid, Laminin and TIMP-1)

[0]: −75.94035+23.20826*LOG(TIMP1)−0.911827*LOG(COL_VI/HYAL)−0.295297*LOG(HYAL/LAM)
[1]: −76.0885+23.14058*LOG(TIMP1)−1.221511*LOG(COL_VI/HYAL)−0.155608*LOG(HYAL/LAM)
[2]: −80.17664+23.65506*LOG(TIMP1)−3.41651*LOG(COL_VI/HYAL)−0.210415*LOG(HYAL/LAM)
[3]: −79.12945+23.42277*LOG(TIMP1)−1.582733*LOG(COL_VI/HYAL)−0.175959*LOG(HYAL/LAM)
[4]: −83.24617+23.7777*LOG(TIMP1)−2.174834*LOG(COL_VI/HYAL)−0.311583*LOG(HYAL/LAM)
[5]: −89.60186+24.2615*LOG(TIMP1)−3.237993*LOG(COL_VI/HYAL)−0.914309*LOG(HYAL/LAM)
[6]: −95.5774+25.11333*LOG(TIMP1)−3.293235*LOG(COL_VI/HYAL)−0.347014*LOG(HYAL/LAM)

Algorithm 3b: (employing Col VI with Hyaluronic Acid, Col IV and PIIINP)

[0]: −100.6452+17.18813*LOG(HYAL)+15.20461*LOG(COL_IV/HYAL)+0515498*LOG(COL_VI/PIIINP)
+3.309452*LOG(LAM)−15.47806*LOG(COL_IV/MMP2)−17.50773*LOG(COL_VI/TIMP1)
[1]: −98.87092+17.18161*LOG(HYAL)+14.7876*LOG(COL_IV/HYAL)+0.53007*LOG(COL_VI/PIIINP)
+3.067209*LOG(LAM)−14.74001*LOG(COL_IV/MMP2)−17.62455*LOG(COL_VI/TIMP1)
[2]: −104.8869+17.78543*LOG(HYAL)+15.25944*LOG(COL_IV/HYAL)+0.352181*LOG(COL_VI/PIIINP)
+3.175207*LOG(LAM)−15.56044*LOG(COL_IV/MMP2)−17.97986*LOG(COL_VI/TIMP1)
[3]: −102.8131+17.32281*LOG(HYAL)+14.69307*LOG(COL_IV/HYAL)+0.176959*LOG(COL_VI/PIIINP)
+2.822227*LOG(LAM)−15.15272*LOG(COL_IV/MMP2)−18.37351*LOG(COL_VI/TIMP1)
[4]: −109.2574+18.44309*LOG(HYAL)+15.53464*LOG(COL_IV/HYAL)−0.152374*LOG(COL_VI/PIIINP)
+2.957847*LOG(LAM)−15.02773*LOG(COL_IV/MMP2)−18.59138*LOG(COL_VI/TIMP1)
[5]: −116.8556+19.00778*LOG(HYAL)+1547539*LOG(COL_IV/HYAL)+0.436656*LOG(COL_VI/PIIINP)
+3.995456*LOG(LAM)−15.54302*LOG(COL_IV/MMP2)−18.53013*LOG(COL_VI/TIMP1)
[6]: −127.2084+21.66093*LOG(HYAL)+17.77795*LOG(COL_IV/HYAL)−0.631902*LOG(COL_VI/PIIINP)
+3.589129*LOG(LAM)−16.1393*LOG(COL_IV/MMP2)−18.40445*LOG(COL_VI/TIMP1)

Algorithm 4b (employing Col VI with Hyaluronic Acid, Laminin and TIMP-1)

[0] −85.3739+0.961665*LOG(COL_VI/HYAL)+1.975774*LOG(HYAL/LAM)+26.93966*LOG(TIMP1)
[1] −86.2963+0.913679*LOG(COL_VI/HYAL)+2.357299*LOG(HYAL/LAM)+27.03427*LOG(TIMP1)
[2] −89.8724+0.593663*LOG(COL_VI/HYAL)+2.211646*LOG(HYAL/LAM)+27.50832*LOG(TIMP1)
[3] −90.0047+0.396858*LOG(COL_VI/HYAL)+2.230884*LOG(HYAL/LAM)+27.45883*LOG(TIMP1)
[4] −94.3636−0.0239*LOG(COL_VI/HYAL)+2.264267*LOG(HYAL/LAM)+27.95567*LOG(TIMP1)
[5] −98.1958−1.374361*LOG(COL_VI/HYAL)+1.418031*LOG(HYAL/LAM)+28.09921*LOG(TIMP1)
[6] −106.131−1.60933*LOG(COL_VI/HYAL)+1.83107*LOG(HYAL/LAM)+29.03373*LOG(TIMP1)

Algorithm 4c (binary outcome employing Col VI with Hyaluronic Acid, Laminin and TIMP-1)

Logit −8.5031−1.124282*LOG(COL-VI/HYAL)−0.111367*LOG(HYAL/LAM)+0.853129*LOG(TIMP1)

Algorithm 5b (employing Col VI with Hyaluronic Acid, Col IV, PIIINP, MMP2)

[0] −509.93+21.03464*(LOG(HYAL))−65.28201*(LOG(COL_IV))−115.3817*(LOG(COL_VI)/
LOG(HYAL))−7.871581*(LOG(PIIINP))+30.02069*(LOG(COL_IV)/LOG(HYAL))+154.8779*
(LOG(MMP2))+510.2511*(LOG(COL_IV)/LOG(MMP2))−169.4857*(LOG(HYAL)/LOG(MMP2))
[1] −503.533+19.84081*(LOG(HYAL))−62.38579*(LOG(COL_IV))−116.4901*(LOG(COL_VI)/
LOG(HYAL))−8.121259*(LOG(PIIINP))+29.14816*(LOG(COL_IV)/LOG(HYAL))+153.1154*
(LOG(MMP2))+502.5139*(LOG(COL_IV)/LOG(MMP2))−163.8827*(LOG(HYAL)/LOG(MMP2))
[2] −510.288+18.37673*(LOG(HYAL))−62.65484*(LOG(COL_IV))−117.3728*(LOG(COL_VI)/
LOG(HYAL))−7.333193*(LOG(PIIINP))+29.35728*(LOG(COL_IV)/LOG(HYAL))+154.7774*
(LOG(MMP2))+497.5602*(LOG(COL_IV)/LOG(MMP2))−153.9391*(LOG(HYAL)/LOG(MMP2))
[3] −516.935+20.14755*(LOG(HYAL))−65.87736*(LOG(COL_IV))−123.3229*(LOG(COL_VI)/
LOG(HYAL))−6.496054*(LOG(PIIINP))+30.54844*(LOG(COL_IV)/LOG(HYAL))+156.3209*
(LOG(MMP2))+514.0645*(LOG(COL_IV)/LOG(MMP2))−166.8154*(LOG(HYAL)/LOG(MMP2))
[4] −522.377+14.67237*(LOG(HYAL))−59.18186*(LOG(COL_IV))−122.7296*(LOG(COL_VI)/
LOG(HYAL))−6.823173*(LOG(PIIINP))+30.7857*(LOG(COL_IV)/LOG(HYAL))+155.904*
(LOG(MMP2))+478.6378*(LOG(COL_IV)/LOG(MMP2))−127.6343*(LOG(HYAL)/LOG(MMP2))
[5] −526.233+18.20806*(LOG(HYAL))−61.05469*(LOG(COL_IV))−120.2586*(LOG(COL_VI)/
LOG(HYAL))−7.691697*(LOG(PIIINP))31.24435*(LOG(COL_IV)/LOG(HYAL))+155.7383*
(LOG(MMP2))+489.0154*(LOG(COL_IV)/LOG(MMP2))−140.9856*(LOG(HYAL)/LOG(MMP2))
[6] −563.804+28.52903*(LOG(HYAL))−70.11008*(LOG(COL_IV))−125.5272*(LOG(COL_VI)/
LOG(HYAL))−6.321247*(LOG(PIIINP))+31.79617*(LOG(COL_IV)/LOG(HYAL))+160.3625*
(LOG(MMP2))+555.8114*(LOG(COL_IV)/LOG(MMP2))−210.7424*(LOG(HYAL)/LOG(MMP2))

Algorithm 5c (binary outcome employing Col VI with Hyaluronic Acid, Col IV, PIIINP, MMP2)

Logit −20.8717+2.11973*(LOG(HYAL))−2.531717*(LOG(COL_IV))−7.252597*(LOG(COL_IV)/
LOG(HYAL))+1.083647*(LOG(PIIINP))+1.493234*(LOG(COL_IV)/LOG(HYAL))+2.794571*
(LOG(MMP2))+16.07724*(LOG(COL_IV)/LOG(MMP2))−10.7448*(LOG(HYAL)/LOG(MMP2))

Algorithm 6b (employing Hyaluronic Acid with Col IV, PIIINP, TIMP-1)

[0] −140.369−0.35106*(LOG(HYAL))+31.3799*(LOG(COL_IV))−1.39524*
(LOG(PIIINP))+24.34635*(LOG(TIMP1))

-continued

[1]  −143.724−0.15137*(LOG(HYAL))+32.39861*(LOG(COL__IV))−17.67661*(LOG(PIIINP))+24.06137*(LOG(TIMP1))
[2]  −143.915+0.002613*(LOG(HYAL))+31.49065*(LOG(COL__IV))−17.03323*(LOG(PIIINP))+24.55546*(LOG(TIMP1))
[3]  −141.045−0.097252*(LOG(HYAL))+30.88321*(LOG(COL__IV))−16.27152*(LOG(PIIINP))+24.43888*(LOG(TIMP1))
[4]  −148.921+0.314333*(LOG(HYAL))+32.14539*(LOG(COL__IV))−16.54838*(LOG(PIIINP))+24.51316*(LOG(TIMP1))
[5]  −154.316+1.19843*(LOG(HYAL))+32.1963*(LOG(COL__IV))−17.33983*(LOG(PIIINP))+24.91516*(LOG(TIMP1))
[6]  −166.646+1.258962*(LOG(HYAL))+34.30716*(LOG(COL__IV))−16.25685*(LOG(PIIINP))+24.63731*(LOG(TIMP1))

Algorithm 6c (binary outcome employing Hyaluronic Acid with Col IV, PIIINP, TIMP-1)

Logit  −7.86615+0.590389*(LOG(HYAL))+0.329412*(LOG(COL__IV))+0.981143*(LOG(PIIINP))+0.314869*(LOG(TIMP1))

Table 4 below shows the diagnostic performance of algorithm 1a, 2a and 3a. Column C reports the results of the comparisons between a consensus score of three pathologists and the marker based results for a given algorithm; column A reports the results of the comparisons between a range of scores reported by three different pathologists and the marker based results; column B reports the results of the comparisons between a score reported by a studies central pathologists (single pathologist) and the marker based results. Hit rate is the percentage of scores reported to be identical by the marker based algorithm and the pathologist's Scheurer score. The Kappa values report agreements between the groups of results. L_Kappa and U_Kappa give the lower and upper limit of confidence for the Kappa value (95% CI); NPV is the negative predictive value for a dichotomized scoring system and PPV is the positive predictive value for a dichotomized system.

TABLE 4

|  | Algorithm 1a | | | Algorithm 2a | | | Algorithm 3a | | |
| --- | --- | --- | --- | --- | --- | --- | --- | --- | --- |
|  | C | A | B | C | A | B | C | A | B |
| Hit-Rate (%) [0] | 28.7 | 31.5 | 29.5 | 45.7 | 58.6 | 41.0 | 45.7 | 57.1 | 39.8 |
| Hit-Rate (%) [1] | 25.0 | 34.0 | 29.2 | 50.8 | 60.7 | 50.8 | 27.9 | 41.0 | 37.7 |
| Hit-Rate (%) [2] | 10.7 | 24.0 | 9.7 | 0.0 | 22.4 | 1.1 | 1.7 | 15.5 | 1.1 |
| Hit-Rate (%) [3] | 23.0 | 27.9 | 20.2 | 0.0 | 3.1 | 0.0 | 9.4 | 12.5 | 6.9 |
| Hit-Rate (%) [4] | 22.2 | 37.8 | 25.6 | 0.0 | 0.0 | 0.0 | 0.0 | 7.7 | 3.3 |
| Hit-Rate (%) [5] | 32.0 | 44.0 | 24.4 | 4.5 | 18.2 | 2.6 | 0.0 | 18.2 | 2.6 |
| Hit-Rate (%) [6] | 57.4 | 57.4 | 51.1 | 71.9 | 71.9 | 60.9 | 43.8 | 43.8 | 52.2 |
| Hit-Rate (%) All | 27.1 | 34.6 | 27.3 | 28.9 | 39.5 | 28.1 | 22.3 | 32.6 | 25.2 |
| N | 468 | 468 | 794 | 301 | 301 | 627 | 301 | 301 | 627 |
| Kappa | 0.138 | 0.228 | 0.136 | — | — | — | 0.031 | 0.093 | 0.041 |
| L_Kappa | 0.090 | 0.177 | 0.100 | — | — | — | −0.02 | 0.039 | 0.006 |
| U_Kappa | 0.186 | 0.279 | 0.173 | — | — | — | 0.084 | 0.147 | 0.076 |
| P(Kappa = 0) | <0.0001 | <0.0001 | <0.0001 | — | — | — | 0.2293 | 0.0003 | 0.0152 |
| NPV (%) [0-2] | 57.2 | 59.4 | 59.1 | 89.9 | 91.0 | 83.9 | 77.8 | 80.4 | 75.1 |
| PPV (%) [3-6] | 71.9 | 79.5 | 74.2 | 40.2 | 50.9 | 41.5 | 47.3 | 55.4 | 48.1 |
| Hit-Rate (%) All | 63.0 | 67.3 | 65.0 | 71.4 | 76.1 | 67.6 | 66.4 | 71.1 | 64.8 |
| Kappa | 0.274 | 0.362 | 0.312 | 0.330 | 0.450 | 0.271 | 0.259 | 0.366 | 0.238 |
| L_Kappa | 0.191 | 0.283 | 0.249 | 0.223 | 0.346 | 0.195 | 0.147 | 0.257 | 0.160 |
| U_Kappa | 0.356 | 0.441 | 0.374 | 0.437 | 0.554 | 0.347 | 0.371 | 0.475 | 0.316 |
| P(Kappa = 0) | <0.0001 | <0.0001 | <0.0001 | <0.0001 | <0.0001 | <0.0001 | <0.0001 | <0.0001 | <0.0001 |
| Sensitivity | 0.524 | 0.561 | 0.537 | 0.703 | 0.770 | 0.617 | 0.558 | 0.626 | 0.547 |
| Specificity | 0.757 | 0.816 | 0.781 | 0.717 | 0.758 | 0.697 | 0.714 | 0.752 | 0.699 |

Table 5 below shows the diagnostic performance of algorithm 4b, 5b and 6b. Column C reports the results of the comparisons between a consensus score of three pathologists and the marker based results for a given algorithm; column A reports the results of the comparisons between a range of scores reported by three different pathologists and the marker based results; column B reports the results of the comparisons between a score reported by a studies central pathologists (single pathologist) and the marker based results; Hit rate is the percentage of scores reported to be identical by the marker based algorithm and the pathologist's Scheurer score; The Kappa value reports agreements between the groups of results, L_Kappa and U_Kappa gives the lower and upper limit of confidence for the Kappa value (95% CI), NPV is the negative predictive value for a dichotomized scoring system, PPV is the positive predictive value for a dichotomized system. In all tables "binary outcome" means that groups of marker scores are formed denoting a group of low marker scores as "negative" and a group of high markers scores as "positive". Using this approach a binary or dichotomized outcome can be defined allowing for a statistical analysis in terms of sensitivity, specificity, NPV, PPV and ROC AUC.

TABLE 5

|  | C Alg. 4b | C Alg. 5b | C Alg 6b | B Alg. 4b | B Alg. 5b | B Alg. 6b | A Alg. 4b | A Alg. 5b | A Alg 6b |
| --- | --- | --- | --- | --- | --- | --- | --- | --- | --- |
| Hit-Rate (%) All | 27.4 | 28.4 | 28.1 | 28.8 | 26.6 | 28.5 | 38.1 | 39.1 | 39.8 |
| Hit-Rate (%) [0] | 44.9 | 34.8 | 43.5 | 43.9 | 29.0 | 41.9 | 54.8 | 40.9 | 50.7 |
| Hit-Rate (%) [1] | 21.7 | 41.7 | 40.0 | 31.2 | 32.8 | 30.4 | 37.7 | 52.9 | 53.5 |
| Hit-Rate (%) [2] | 3.4 | 12.1 | 6.9 | 6.7 | 12.2 | 8.9 | 9.3 | 21.4 | 14.3 |
| Hit-Rate (%) [3] | 12.5 | 12.5 | 9.4 | 5.7 | 17.1 | 15.7 | 21.9 | 31.3 | 31.4 |
| Hit-Rate (%) [4] | 26.9 | 15.4 | 11.5 | 27.3 | 14.5 | 10.9 | 36.0 | 36.0 | 28.0 |
| Hit-Rate (%) [5] | 18.2 | 45.5 | 40.9 | 12.8 | 35.9 | 33.3 | 26.3 | 55.0 | 47.6 |
| Hit-Rate (%) [6] | 65.6 | 34.4 | 34.4 | 53.7 | 43.3 | 44.8 | 71.4 | 37.5 | 38.7 |
| N | 299 | 299 | 299 | 601 | 601 | 601 | 299 | 299 | 299 |
| Kappa | 0.129 | 0.098 | 0.147 | 0.137 | 0.133 | 0.148 | 0.253 | 0.182 | 0.281 |
| L_Kappa | 0.070 | 0.043 | 0.089 | 0.095 | 0.092 | 0.106 | 0.189 | 0.124 | 0.217 |
| U_Kappa | 0.188 | 0.152 | 0.205 | 0.180 | 0.174 | 0.189 | 0.318 | 0.241 | 0.345 |
| P(Kappa = 0) | <0.0001 | <0.0001 | <0.0001 | <0.0001 | <0.0001 | <0.0001 | <0.0001 | <0.0001 | <0.0001 |
| Binary Outcome: | Alg. 4c | Alg. 5c | Alg 6c | Alg 4c | Alg 5c | Alg 6c | Alg. 4c | Alg. 5c | Alg. 6c |
| PPV (%) [3-6] | 54.8 | 56.0 | 54.7 | 60.7 | 56.4 | 55.1 | 55.6 | 57.4 | 56.8 |
| NPV (%) [0-2] | 74.9 | 79.1 | 77.5 | 76.6 | 78.4 | 78.5 | 76.0 | 82.3 | 79.4 |
| Hit-Rate (%) All | 66.6 | 68.2 | 66.9 | 70.2 | 67.7 | 66.7 | 67.6 | 70.6 | 68.9 |
| Kappa | 0.301 | 0.355 | 0.326 | 0.376 | 0.350 | 0.336 | 0.321 | 0.402 | 0.367 |
| L_Kappa | 0.192 | 0.251 | 0.220 | 0.301 | 0.276 | 0.263 | 0.212 | 0.300 | 0.262 |
| U_Kappa | 0.411 | 0.460 | 0.432 | 0.452 | 0.423 | 0.409 | 0.430 | 0.504 | 0.471 |
| P(Kappa = 0) | <0.0001 | <0.0001 | <0.0001 | <0.0001 | <0.0001 | <0.0001 | <0.0001 | <0.0001 | <0.0001 |
| Sensitivity | 60.7 | 70.5 | 67.9 | 63.6 | 71.0 | 72.3 | 67.3 | 74.3 | 70.5 |
| Specificity | 70.1 | 66.8 | 66.3 | 74.3 | 65.7 | 63.2 | 70.7 | 68.4 | 67.9 |
| N(AUC) | 299 | 299 | 299 | 601 | 601 | 601 | 299 | 299 | 299 |
| AUC(ROC) | 0.756 | 0.764 | 0.775 | 0.769 | 0.769 | 0.775 | 0.840 | 0.846 | 0.862 |

(e) Receiver Operating Characteristic (ROC) Curves for Scheuer Score.

Grouping the patients into categories no/mild fibrosis (score 0-1) and moderate/severe fibrosis (score 2-4) for the Scheuer score and calculating algorithms for the dichotomous outcome gave the following results:

Algorithm 7:

LOGIT = 7.11957755−0.67952658 LOG(TIMP1)+1.01832374*LOG(COL_VI/HYAL)+0.09461778*LOG(HYAL/LAM)

Algorithm 8:

LOGIT = 8.6908419−0.76944684*LOG(HYAL)−0.47836706*LOG(COL_IV)+0.43870798*LOG(COL_VI/PIIINP)+0.74453459*LOG(COL_VI/TIMP1)+0.05605262*LOG(HYAL/MMP2)−0.01871531*LOG(LAM/MMP9T)

The algorithms were used to calculate receiver operating characteristic curves for the categories no/mild fibrosis (score 0-1) and moderate/severe fibrosis (score 2-4) for the Scheuer score. The calculated scores were compared with scores determined by a single pathologist (case B), with a consensus score of 3 pathologists (case C) and with the range covered by all pathologists (case A). Area under curve (AUC) values have been calculated.

Table 6 shows the diagnostic performance of algorithm 7 and 8. Column C reports the results of the comparisons between a consensus score of three pathologists and the marker based results for a given algorithm; column A reports the results of the comparisons between a range of scores reported by three different pathologists and the marker based results; column B reports the results of the comparisons between a score reported by a studies central pathologists (single pathologist) and the marker based results; The table summarized a "binary outcome" means that groups of marker scores are formed denoting the group of score 0 and 1 as "negative" and a group of scores 2 to 4 as "positive" (Scheurer). AUC denotes the Area under the Curve in a receiver operator characteristics analysis. N is the number of subjects investigated.

TABLE 6

|  | Algorithm 7 | | | Algorithm 8 | | |
| --- | --- | --- | --- | --- | --- | --- |
|  | C | A | B | C | A | B |
| AUC | 0.759 | 0.899 | 0.759 | 0.746 | 0.871 | 0.756 |
| N | 295 | 295 | 569 | 291 | 291 | 562 |

(f) Receiver Operating Characteristic (ROC) Curves for Ishak Score.

Grouping the patients into categories no/mild fibrosis (score 0-2) and moderate/severe fibrosis (score 3-6) for the Ishak score and calculating algorithms for the dichotomous outcome gave the following results:

summarized a "binary outcome" means that groups of marker scores are formed denoting the group of score 0 and 2 as "negative" and a group of scores 3 to 6 as "positive" (Ishak). AUC denotes the Area under the Curve in a receiver operator characteristics analysis. N is the number of subjects investigated.

TABLE 7

|  | Algorithm 7a | | | Algorithm 8a | | |
| --- | --- | --- | --- | --- | --- | --- |
|  | C | A | B | C | A | B |
| AUC | 0.763 | 0.887 | 0.763 | 0.751 | 0.861 | 0.757 |
| N | 295 | 295 | 570 | 292 | 292 | 564(g) |

Grouped Scores and Multiple Markers.

The liver fibrosis serum markers PIIINP, Collagen IV, Collagen VI, Tenascin, Laminin, Hyaluronan, MMP-2, TIMP-1 and MMP-9/TIMP-1 complex together with age, sex and transaminase values are also useful to stratify patients into groups of none/mild fibrosis, moderate fibrosis and severe fibrosis by grouping the Ishak Scores into the three following groups: Group 1 Ishak Score 0 and 1; Group 2: Ishak Score 2, 3 and 4 and Group 3: Ishak Score 5 and 6. Although the concentrations of the individual markers like Hyaluronic Acid, PIIINP, MMP2, Collagen IV and TIMP-1 correlate with the severity of liver fibrosis, combinations of markers yield a clearly superior diagnostic performance. This aspect of the study shows the correlation of single markers with the severity of liver fibrosis as assessed by grouped scores while algorithms 9, 10, and 11 exemplify the improvements that can be achieved by combining more than one marker into an algorithm.

Hyaluronic Acid.

Hyaluronic Acid has historically shown the best association with stages of liver fibrosis. The discriminant function for Hyaluronic Acid (in Natural log units) was developed on the

---

Algorithm 7a:

LOGIT = 7.22920269−0.68033581*LOG(TIMP1)+1.04300795*LOG(COL__VI/HYAL)+0.08483109*LOG(HYAL/LAM)

Algorithm 8a:

LOGIT = 8.92321331−1.28340678*LOG(HYAL)−0.54350583*LOG(COL__IV/HYAL)+
0.47836792*LOG(COL__VI/PIIINP)+0.02076678*LOG(LAM)+0.07719237*LOG(COL__IV/MMP2)+
0.76194671*LOG(COL__VI/TIMP1)

---

The algorithms were used to calculate receiver operating characteristic curves for the categories no/mild fibrosis (score 0-2) and moderate/severe fibrosis (score 3-6) for the Ishak score. The calculated scores were compared with scores determined by a single pathologist (case B), with a consensus score of 3 pathologists (case C) and with the range covered by all pathologists (case A). Area under curve (AUC) values have been calculated as shown in Table 7.

Table 7 shows the diagnostic performance of algorithm 7a and 8a. Column C reports the results of the comparisons between a consensus score of three pathologists and the marker based results for a given algorithm; column A reports the results of the comparisons between a range of scores reported by three different pathologists and the marker based results; column B reports the results of the comparisons between a score reported by a studies central pathologists (single pathologist) and the marker based results; The table training cohort also used for the development of all other algorithms. The discriminant score ($D_{HA}$) is given by $$D_{HA} = -3.97 + 1.016 Ln(HA)$$

Examination of the discriminant scores compared to the biopsy readings suggests that the Ishak scores be grouped as follows:

| Ishak Score | Disease State |
| --- | --- |
| 0-1 | None or Mild Fibrosis |
| 2-4 | Moderate Fibrosis |
| 5-6 | Severe Fibrosis |

Modifying the Ishak system in the manner above produced the following training set discriminant function $$D_{HA} = -3.70 + 0.992 Ln(HA)$$

Processing the Hyaluronic Acid marker results from the validation set used for the validation of all markers indicates a clear and distinct separation of the three groups based on this marker alone. Cutoff values were picked to achieve 85% sensitivity to detect severe and moderate fibrosis. The specificity to separate these groups from the none/mild fibrosis group was the computed. Table 7a below shows the cutoffs with the respective specificities.

TABLE 7a

Cutoffs at 85% Sensitivity
With Specificity compared to None or Mild Fibrosis
Hyaluronic Acid

| Disease State | Cutoff | Specificity |
|---|---|---|
| Severe Fibrosis | −0.135 | 43.1% |
| Moderate Fibrosis | −1.23 | 22.9% |

Amionoterminal Propeptide of Procollagen Type 3 (PIIINP)

The discriminant function for this marker determined in the training cohort was determined As $$D_{PIIINP} = -2.657 + 1.646 * Ln(PIIINP)$$

Computing the discriminant scores derived from the PIIINP concentration in the validation group show that there is a clear separation between the groups. The specificity of the marker PIIINP to separate between non/mild and moderate respectively severe disease at the 85% sensitivity level is depicted in Table 7b below.

TABLE 7b

Cutoffs at 85% Sensitivity
With Specificity compared to None or Mild Fibrosis
PIIINP

| Disease State | Cutoff | Specificity |
|---|---|---|
| Severe Fibrosis | −0.135 | 65.3% |
| Moderate Fibrosis | −0.855 | 30.5% |

Matrixmetaloproteinases type 2 (MMP2)

The discriminant function for this assay, again determined in the training cohort is $$D_{MMP2} = 15.0 + 2.354 Ln(MMP2)$$

Computing the discriminant scores derived from the MMP2 concentration in the validation group show that there is a clear separation between the groups. The specificity of the marker MMP2 to separate between non/mild and moderate respectively severe disease at the 85% sensitivity level is depicted in Table 7c below.

TABLE 7c

Cutoffs at 85% Sensitivity
With Specificity compared to None/Mild Fibrosis
MMP2

| Disease State | Cutoff | Specificity |
|---|---|---|
| Severe Fibrosis | −0.276 | 43.3% |
| Moderate Fibrosis | −0.664 | 12.7% |

Collagen IV

The discriminant function for Type IV collagen, again as assessed in the training cohort is $$D_{Co/4} = -11.341 + 2.273 Ln(CollagenIV)$$

Computing the discriminant scores derived from the Collagen IV concentration in the validation group show that there is a clear separation between the groups. The specificity of the marker collagen IV to separate between non/mild and moderate respectively severe disease at the 85% sensitivity level is depicted in Table 7d below.

TABLE 7d

Cutoffs at 85% Sensitivity
With Specificity compared to None or Mild Fibrosis
Collagen IV

| Disease State | Cutoff | Specificity |
|---|---|---|
| Severe Fibrosis | −0.421 | 52.6% |
| Moderate Fibrosis | −0.887 | 22.6% |

Tissue Inhibitor of Metalloproteinases Type I (TIMP-1)

The only other single marker that significantly discriminated the grouped Ishak categories was TIMP-1. The discriminant function is $$D_{TIMP1} = -13.289 + 2.036 * Ln(TIMP-1)$$

Computing the discriminant scores derived from the Collagen IV concentration in the validation group show that there is a clear separation between the groups. The specificity of the marker TIMP-1 to separate between non/mild and moderate respectively severe disease at the 85% sensitivity level is depicted in Table 7e below.

TABLE 7e

Cutoffs at 85% Sensitivity
With Specificity compared to None or Mild Fibrosis
TIMP-1

| Disease State | Cutoff | Specificity |
|---|---|---|
| Severe Fibrosis | −0.673 | 34.1% |
| Moderate Fibrosis | −1.014 | 21.1% |

(h) Multiple Markers.

This aspect of the study shows the improvement that can be achieved by combining more than one serum marker into a diagnostic algorithm.

Algorithm 9 contains PIINP and Collagen IV. The discriminant function derived from the marker finding cohort is:

$$D_{M1} = -7.522 + 1.21 Ln(CollagenIV) + 0.947 Ln(PIIINP)$$

Computing the discriminant scores derived from the Algorithm 9 in the validation group show that there is a clear separation between the groups. The specificity of the achieved with algorithm 9 to separate between non/mild and moderate respectively severe disease at the 85% sensitivity level is depicted in Table 7f below.

TABLE 7f

Cutoffs at 85% Sensitivity
With Specificity compared to None or Mild Fibrosis
Algorithm 9

| Disease State | Cutoff | Specificity |
|---|---|---|
| Severe Fibrosis | −0.074 | 71.9% |
| Moderate Fibrosis | −0.862 | 24.8% |

Although the figures show a remarkable specificity increase at the 85% sensitivity level a comparison of the specificities for Algorithm 9 and PIIINP alone for severe disease, a McNemar test for correlated proportions indicates that the increase is not significant at the 0.05 level. It should be noted that the exact p of 0.07 is tending toward significance. It is significant at the 0.1 level though showing that Algorithm 9 outperforms all single marker derived Ishak scores. There is no significant increase in the specificity compared to the moderate disease group.

Algorithm 10

Hyaluronic Acid was added to Algorithm 9 with the marker finding cohort yielding the following discriminant function: (Algorithm 10).

$D_{ModelII} = -6.704 + 0.749 Ln(CollagenIV) + 0.607 Ln(HyaluronicAcid) + 0.436 Ln(PIIINP)$ Computing the discriminant scores derived from the Algorithm 10 in the validation group show that there is a clear separation between the groups. The specificity of the achieved with algorithm 10 to separate between non/mild and moderate respectively severe disease at the 85% sensitivity level is depicted in Table 7g below.

TABLE 7g

Cutoffs at 85% Sensitivity
With Specificity compared to None or Mild Fibrosis
Algorithm 10

| Disease State | Cutoff | Specificity |
|---|---|---|
| Severe Fibrosis | −0.080 | 79.3% |
| Moderate Fibrosis | −0.919 | 31.4% |

The McNemar $\chi^2$ is highly significant indicating that the specificity of Algorithm 10 is far superior to PIIINP alone or any other single marker. Also Algorithm 10 is superior over Algorithm 9 at the 0.05 significance level.

Algorithm 11 (PIIINP, Collagen IV, Hyaluronic Acid and MMP2)

Computing the discriminant scores derived from the Algorithm 11 in the validation group show that there is a clear separation between the groups. The specificity achieved with algorithm 11 to separate between non/mild, and moderate respectively severe disease at the 85% sensitivity level is depicted in Table 7h below.

TABLE 7h

Cutoffs at 85% Sensitivity
With Specificity compared to None or Mild Fibrosis
Algorithm 11

| Disease State | Cutoff | Specificity |
|---|---|---|
| Severe Fibrosis | −0.229 | 80.6% |
| Moderate Fibrosis | −0.662 | 32.5% |

Although algorithm 11 shows a specificity improvement at the 85% sensitivity level compared to the results of each single marker, the improvement of Algorithm 11 over Algorithm 10 has not reached significance in the sample size investigated: McNemar $\chi^2=2.18$, p=0.14. As for all other improvements of the performance that has not reached sensitivity it is highly likely that it will once larger patient cohorts will be investigated.

2. Longitudinal Monitoring of the Progression of Liver Disease.

Eighty-five patients were monitored over two years with a liver biopsy taken in the beginning and at the end of the study. Serum was drawn from all patients and at one to eight different time points during the study.

The marker derived calculated pathology score was computed from the following logistic regression:

$D = -10.06 + 0.814 Ln(CRATIO) + 0.640 Ln(HYALURON) + 0.639 Ln(MMP2) + 0.431 Ln(P3NP)$ (Algorithm 12)

In algorithm 12, CRATIO means the ratio of serum values of collagen VI and collagen IV.

The following Table 8 summarizes how the discriminant scores (Algorithm 12) from patients from the assay validation cohort are clustering around their corresponding histopathology scores:

TABLE 8

| Ishak Score | n | Mean | SD | SE | 95% CI of Mean | | Median | 95% CI of Median | |
|---|---|---|---|---|---|---|---|---|---|
| 0 | 155 | −0.770 | 0.823 | 0.066 | −0.900 | −0.639 | −0.890 | −1.040 | −0.730 |
| 1 | 125 | −0.612 | 0.795 | 0.071 | −0.753 | −0.471 | −0.620 | −0.820 | −0.480 |
| 2 | 90 | −0.203 | 1.041 | 0.109 | −0.421 | 0.016 | −0.325 | −0.500 | −0.090 |
| 3 | 70 | −0.001 | 1.102 | 0.132 | −0.264 | 0.261 | −0.220 | −0.400 | 0.280 |
| 4 | 55 | 0.291 | 1.126 | 0.152 | −0.013 | 0.596 | 0.170 | −0.190 | 0.550 |
| 5 | 39 | 0.907 | 1.176 | 0.188 | 0.526 | 1.288 | 0.690 | 0.260 | 1.290 |
| 6 | 67 | 1.538 | 1.396 | 0.171 | 1.197 | 1.878 | 1.520 | 1.310 | 1.890 |

Cutoff values to allow making a call for individual scores were established by taking the average of the corresponding discriminant scores to be separated. Using the calculated liver disease scores a non parametric regression was computed to obtain a slope (severity of disease vs. time; Theil estimator of the regression coefficient). 95% confidence intervals were computed for each slope with a confidence variable v defined for each slope. v has the following values:

1 (positive) if the slope>0 and the 95% CI does not contain zero v=0 if the 95% CI for the slope contains zero −1 (negative) if the slope is negative and the 95% CI does not does not contain zero Accordingly w was defined as:

−1 (improvement) if the Ishak score decreased by at least 2 levels w=0 (no change) if the Ishak score was ±1

1 (progression) if the Ishak score increased by at least 2 levels

With these two definitions a three by three concordance table for the results of the 85 patients was set up yielding the following results shown in Table 9.

TABLE 9

| Slope (v) | Change in Pathology (w) | | | Total |
|---|---|---|---|---|
| | −1 | 0 | 1 | |
| −1 | 1 | 11 | 0 | 12 |
| 0 | 6 | 41 | 7 | 54 |
| 1 | 1 | 13 | 5 | 19 |
| Total | 8 | 65 | 12 | 85 |

Table 9 shows that for the 12 patients that had a disease progression (assessed by pathology) no patient had a declining discriminant score. Also, for those patients who had improvement in their disease only one had a positive slope. Overall, the concordance is significant at the 0.1 level proving the ability of the serum marker based algorithms to monitor the progression and regression of liver disease longitudinally.

Further analyses of the Multicenter ("ELF") Study.

The data collected in the ELF study were reanalyzed using an alternative approach to the statistical analyses of the data.

The performance of embodiments of the invention in the ELF study was compared to two extensively accepted histological staging systems. It is recognized that histological staging is based upon flawed assumptions. First, all staging systems require the pathologist to assign categorical values to biopsies in order to differentiate stages that represent a range of fibrosis from "none" to "cirrhosis." This range of pathology would be more accurately represented by a continuous variable score. Secondly, both the Scheuer and Ishak histological staging systems assume linearity of progression between stages, but it is widely recognized that a stage of 4 is not necessarily twice as bad as a stage of 2(30A; 31A)

To address this second assumption, an embodiment of the invention was used to determine the distribution of algorithm scores across a range of fibrosis in order to determine how the scores vary with histological disease severity. Previous surrogate marker studies have arbitrarily bifurcated histological stages into two groups taken to represent "no or mild fibrosis" and "moderate or severe fibrosis", based upon the opinions of experts and the assumption that progression through the histological stages is linear. These bifurcated stages were then used to compare the performance of histology to serum marker scores.

In the present analysis, no assumption was made about the grouping of liver histological stages and their correlation with marker scores. The marker data were plotted, revealing two natural groupings with a clear division that correlated with bifurcation of the histology stages at a point between Scheuer stages 2 and 3, and Ishak stages 3 and 4. The data indicate that these changes in stage represent biologically significant step points in disease progression.

Specifically, the relationship between levels of nine serum fibrosis markers and liver fibrosis was assessed by histological examination of liver biopsies from 1,021 subjects obtained as part of the investigation of chronic liver disease at 13 centers in the previously described ELF study. The recruitment of patients in the study is shown in FIG. 1.

In the ELF Study, subjects were considered eligible if they were due to undergo liver biopsy for the investigation of chronic liver disease, defined as abnormal biochemical liver function tests persisting for more than 6 months. Additional inclusion criteria were the ability to provide informed consent, age over 18 years and less than 75 years. Patients were excluded from the study if their age fell outside this range; if they had any disorder associated with extra-hepatic fibrosis including rheumatic, renal or lung disease; if they had cardiovascular disease or cancer; advanced cirrhosis with evidence of decompensation (Child-Pugh class C) ; consumption of regular aspirin; or had hepatocellular carcinoma or drug-induced liver disease.

Of the 1,021 subjects recruited the numbers in each diagnostic category were: Chronic Hepatitis C 496; Alcoholic liver disease 64; Primay Biliary Cirrhosis or Primary Sclerosing Cholangitis 53; Fatty liver 61; Hepatitis B 61; Recurrent disease Post Liver Transplant 48; Autoimmune Hepatitis 45; Haemochromatosis 32; Cryptogenic cirrhosis 19; Hepatitis B&C 4; Other (including granulomatous disease of unknown aetiology and normal 138. Men represented 63% of the sample; the average age was 44.1 years, standard deviation=12.8 years, range=19-25 years. There were no significant differences between the subjects in GA, GT, GV or morphometry groups.

Serum samples in addition to routine blood tests, were obtained at the time of liver biopsy and processed immediately. Nine different immunoassays were developed to run on the Bayer IMMUNO 1™ system. The heterogenous ELISA-type assays formatted for the Bayer Immuno 1 system described previously herein were used. The full panel of molecular targets was selected as surrogate markers of matrix synthesis or degradation, based upon knowledge of the basic mechanisms involved in liver fibrosis. The antibody pairs used in the assays, and their sources, were the same as the antibody pairs and sources described previously in connection with the discussion herein of the use of discriminant function analysis to determine variables that discriminate between the different liver fibrosis scores. No serum marker scores were deemed indeterminate.

All biopsies were analyzed locally and by one central pathologist (A). Clinical details or biochemical samples were incomplete for 45 subjects and 55 of the remaining 976 biopsies were considered to be inadequate for full histological analysis due to inadequate length (<12mm) or too few portal tracts. Biopsies, serum samples and clinical details were available for 921 subjects who were included in the final analysis constituting group $G_A$.

Three expert liver pathologists participated in the study. The Central Pathologist (A) assessed 921 biopsies using the Scheuer (27) and Ishak (28) staging systems. For conditions other than chronic viral or immune hepatitis modifications of the criteria statements were made to reflect the distribution of fibrosis (e.g. in alcoholic and non-alcoholic steatohepatitis, perivenular and pericellular fibrosis replaced portal and periportal fibrosis). This group was denoted as $G_A$ and it was from this group of samples that the test and validation sets were derived. Pathologist A and B used a separate "coaching" set of slides, reflecting the range of chronic liver diseases represented in the study to initially harmonize their scoring prior to assessing the study biopsies. Pathologist C used the same descriptors for the Ishak and Scheuer systems as A and B but staged biopsies without having undergone "coaching". Pathologist A re-staged all 921 biopsies including a "consensus set" of 620 designated $G_C$ that were also staged independently by pathologists B and C. Individual fibrosis stages (Scheuer 0-4 and Ishak 0-6) were recorded.

In this way four series of sets of staging were generated. Those of the central pathologist are designated $R_{A1}$ and $R_{A2}$, those pathologist B, $R_B$, and pathologist C, $R_C$. Comparison of these stagings allows investigation of intra-observer variation ($R_{A1}$ versus $R_{A2}$), inter-observer variation between "coached" pathologists reflecting the research setting ($R_{A1}$ versus $R_B$) and inter-observer variation between expert hepato-pathologists working independently but using shared scoring systems ($R_{A1}$ versus $R_C$, and $R_B$ versus $R_C$). These latter comparisons accurately reflect the situation that pertains in clinical practice.

(a) Analytical Techniques.

In order to derive algorithms combining serum markers a group of 400 cases ($G_T$) was selected at random from the group of 921 patients with biopsies. Algorithms were developed by including a marker if its addition to the algorithm increased the overall generalized distance between groups. Clinical chemistry and haematology test results were also examined in this way. An optimal algorithm was selected and the performance of this algorithm was then validated in the remaining set of 521 biopsies from $G_A$ designated as the validation group ($G_V$) using the staging assigned by pathologist A. Analysis of the performance characteristics of this algorithm in relation to its ability to distinguish between histological fibrosis staging was used to identify the break point that distinguishes between cases with lower histological fibrosis staging from those with higher staging, thus creating binary outcomes that may reflect the true biological progression of liver fibrosis. This approach avoided assumptions about the linearity of fibrosis progression. The reproducibility of the performance of the algorithm was evaluated by determining its performance against biopsy staging assigned by pathologists B and C.

Morphometric image analysis was conducted using a Kontron image analyser and an interactive programme allowing field editing to measure the area of fibrosis as a percentage of total liver tissue detected after staining 836 suitable biopsies with Pico Sirius Red/Fast Green. The percentage of the entire section stained positive for fibrous tissue was determined in each case and a mean value generated (20A).

Applied statistical methods included analysis of variance (ANOVA), discriminant analysis, and logistic regression for binary grouped biopsy stage. Kappa statistics were calculated to determine agreement between pathologists. Sensitivity, specificity, positive predictive value (PPV), negative predictive value (NPV), and prevalence for the binary outcomes were assesses using ROC analysis. All analyses were performed using the SPSS® software package (SPSS, Inc., Chicago, Ill. USA).

(b) Results.

In all cases agreement between pathologists for the Scheuer staging exceeded that for the Ishak staging. The level of agreement between the two sets of staging assigned by pathologist A ($R_{A1}$ and $R_{A2}$) was high, (kappa>0.9 for Scheuer and 0.76 for Ishak).

The primary aim of the study was to investigate the ability of serum markers to identify significant histological fibrosis. The mean, median and standard error of the mean (SEM) for each marker in $G_T$ and $G_V$ were determined. A multivariate ANOVA indicated that there were no between group differences for all markers taken together (Hotelling's T=0.01, F=1.14, df1=9, df2=911, p=0.33). An examination of the associated individual t-tests revealed no significant differences between the groups on any individual marker. Chi-square analysis indicated that there are no differences in the etiologic breakdown for each group. (Likelihood Ratio Chi-square=6.34, df=6, p=0.38) (data not shown).

Algorithms combining the serum markers were evaluated for each scoring system for their ability to discriminate between the biopsy stages in the $G_T$ group.

Similar performance characteristics were found with algorithms that incorporate hyaluronic acid, collagen IV, collagen VI, laminin, amino terminal peptide of procollagen III (PIIINP), tissue inhibitor of metaloproteinase 1 (TIMP-1) and matrix metalloproteinase 2 (MMP-2) in varying combinations. The addition of other serum markers, the results of clinical chemistry tests including liver function tests, or haematological indices including platelet count and prothrombin time did not improve the performance of the algorithms.

Figure 2A:
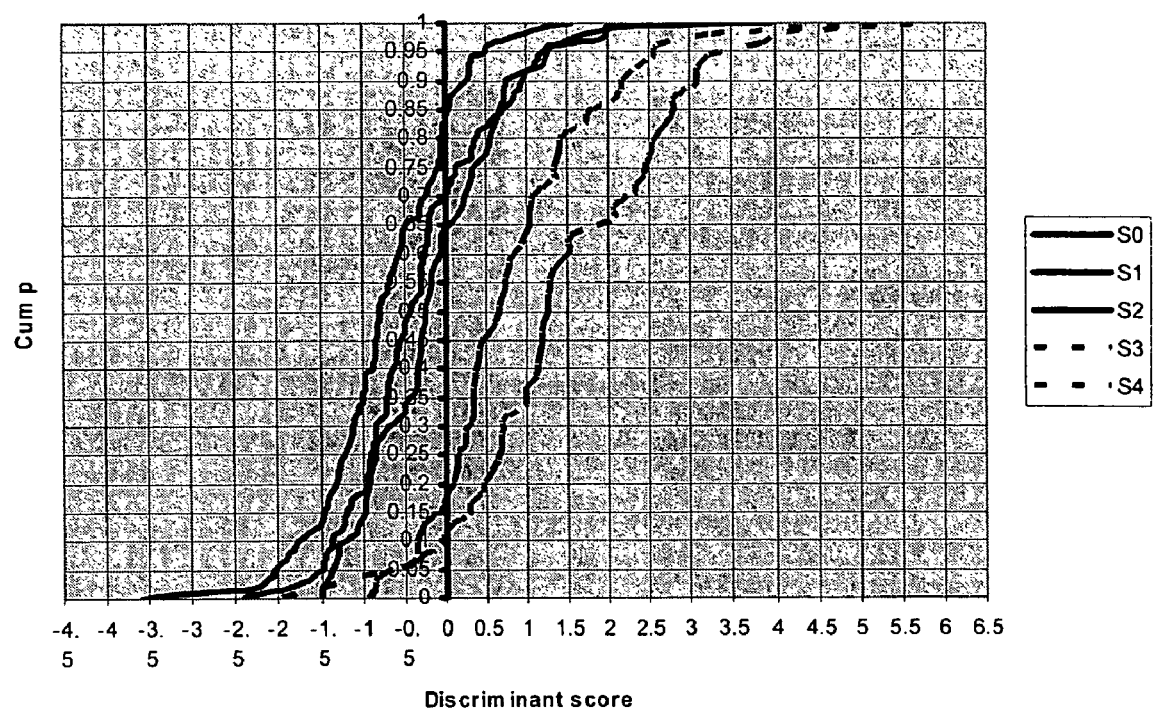
FIG. 2a depicts a graph of cumulative p scores against discriminant scores and reflects the cumulative distribution of Scheuer stage scores ascertained by methods of the invention.
Figure 2B:
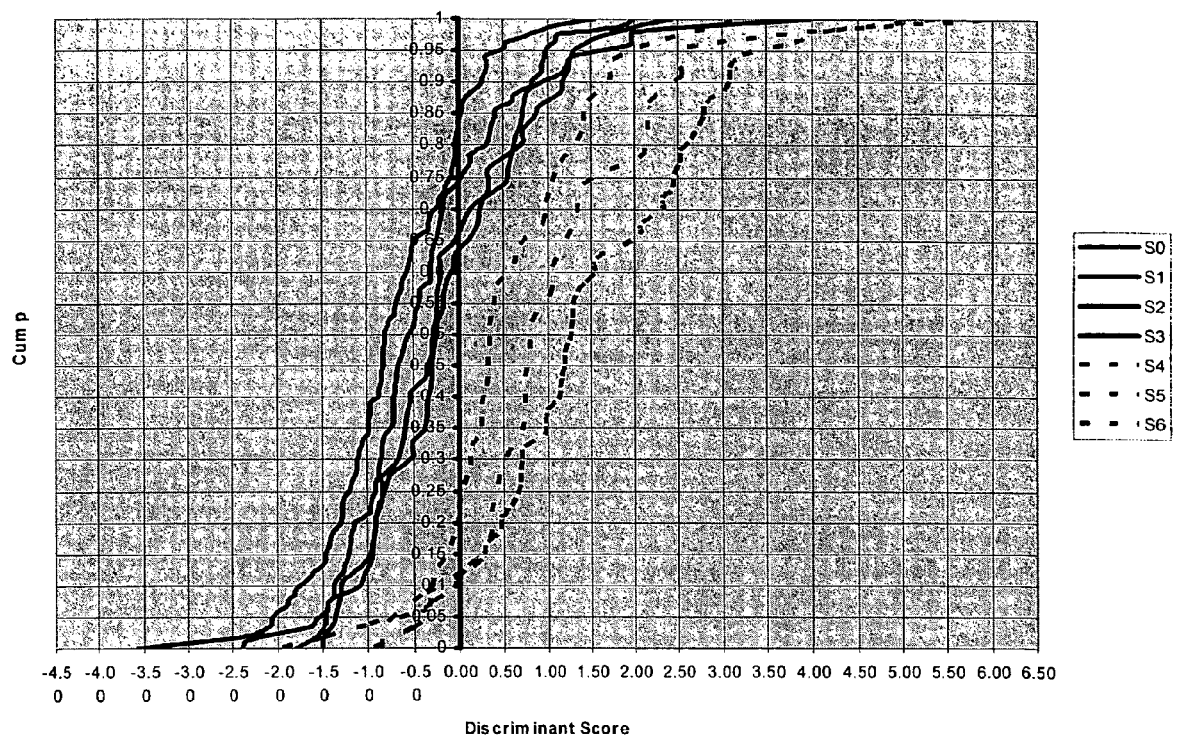
FIG. 2b depicts a graph of cumulative p scores against discriminant scores and reflects the cumulative distribution of Ishak Stage scores ascertained by methods of the invention.
Figure 3A:
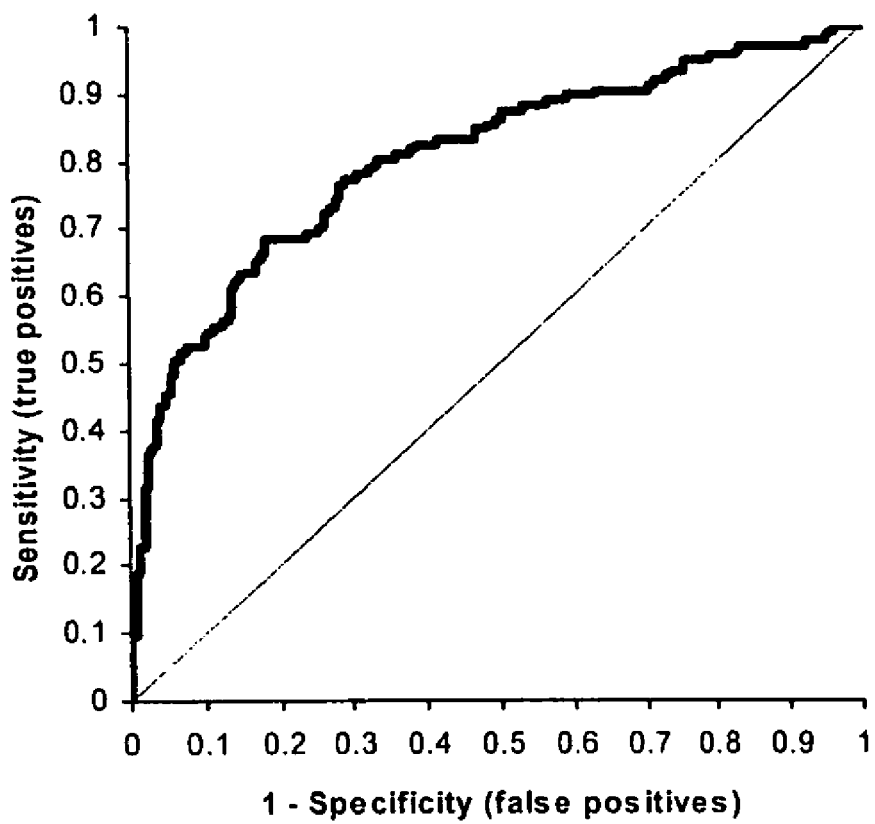
FIG. 3a illustrates Receiver Operator Characteristic Curve-Scheuer Modified Scoring System Validation Data determined in accordance with the invention.
Figure 3B:
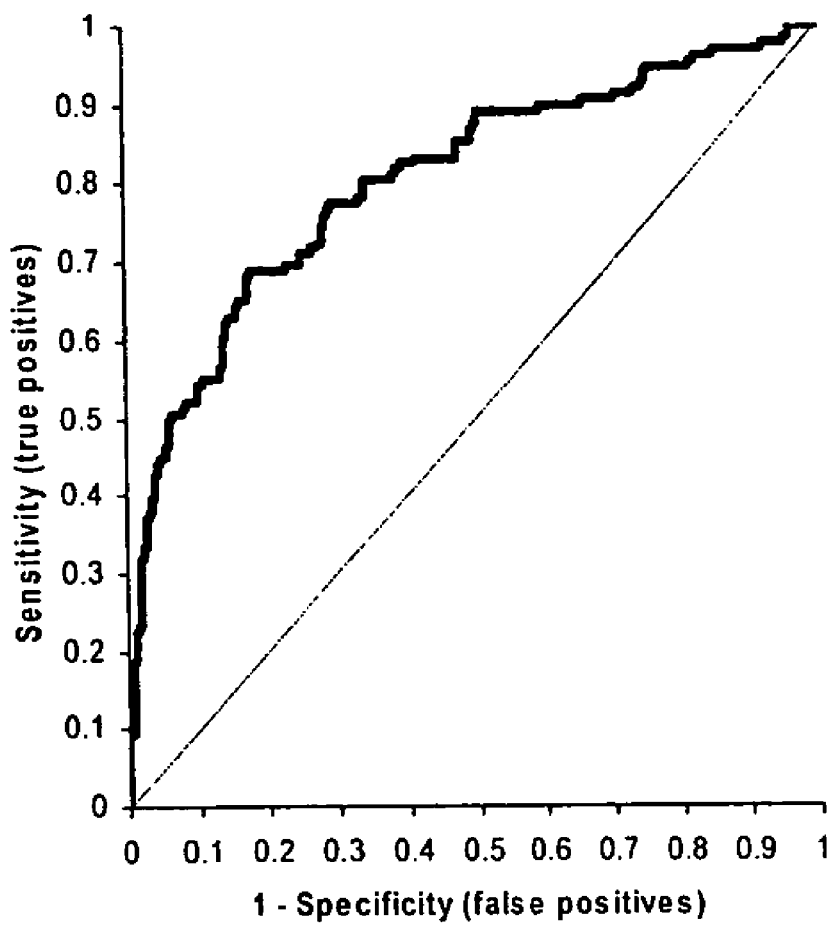
FIG. 3b illustrates Receiver Operator Characteristic Curve-Ishak Modified Scoring System Validation Data determined in accordance with the invention.

We present the results for the algorithm that resulted in the maximum separation of the biopsy groups over the full range of stages (Scheuer stages 0-4, Ishak stages 0-6). The results from all similar combinations indicated that the biopsy stages within each scale could be bifurcated. FIG. 2a demonstrates the cumulative distribution for the 3 marker "best fit" model for the Scheuer staging system. FIG. 2b demonstrates the cumulative distribution for the model in the Ishak system. The model contained values for hyaluronic acid, amino terminal peptide of procollagen III (PIIINP), tissue inhibitor of metaloproteinase 1 (TIMP-1) and age. The formulae for these algorithms were as follows.

The formulae for the algorithms used in these analyses are as follows:

Scheuer:

$$\text{Score} = \frac{1}{1 + e^{-z}}$$

$$Z = -0.132\ln(\text{age}) + 0.97\ln(HyaluronicAcid) + 0.772\ln(PIIINP) + 0.477\ln(TIMP1) - 8.821$$

Ishak:

$$\text{Score} = \frac{1}{1 + e^{-z}}$$

With:

$$Z = -0.196 \cdot ln(\text{age}) + 0.959 \cdot ln(\text{HyaluronicAcid}) + 0.761 \cdot ln(\text{PIIINP}) + 0.539 \cdot ln(\text{TIMPI}) - 8.92$$

Examination of the distributions indicated a natural division at the Ishak stage of 3 or at a Scheuer stage of 2. This was substantiated by examination of the generalized distances between stages on each system (data not shown) generating two categories of "No/Mild" and "Moderate/Severe" fibrosis corresponding to Scheuer 0-2, Ishak 0-3 and Scheuer 3-4, Ishak 4-6 respectively (see FIG. 4). Logistic regression was used to fit the bifurcated staging for each system to the model presented above. Logistic scores were obtained for patients in the test ($G_T$) and validation ($G_V$) groups. Table 10(a) demonstrates the AUC for each bifurcated system in both groups. Both systems yield identical results in term of AUC. For the $G_V$ cohort the AUC are 0.804; SE=0.023; p<0.0001; 95% CI=0.758 to 0.851 for Scheuer and 0.804; SE=0.023; p<0.0001; 95% CI=0.758 to 0.850 for Ishak.

Referring to FIG. 1, the middle horizontal line is the median, the notched region denotes the estimated 95% CI on the median. The end lines are the $25^{th}$ and $75^{th}$ percentile. The dashed lines indicate the "acceptable range" for data. Crosses and circles indicate potential "outliers." The data plotted shows the distribution of discriminant scores for biopsies of Scheuer stage 0-2 and 3-4.

Performance of the algorithm in specific chronic liver diseases was evaluated. The AUC for the three most common liver disorders in the cohort are also shown in Tables 10(a) and (b) for both the Scheuer and Ishak stage systems. The data represent the performance of the algorithm in detecting bifurcated outcomes (0,1,2:3,4 for Scheuer and 0,1,2,3:4,5,6 for Ishak) for the 400 Test (GT) and 521 Validation (GV) samples from the whole cohort of patients with diverse chronic liver diseases; and for patients with hepatitis C, Non-alcoholic fatty liver disease and alcoholic liver disease. Area Under the Curve for Receiver Operator Characteristic curves, standard errors (SE), associated p values and 95% confidence intervals for the AUC are presented.

TABLE 10(a)

Area Under the Curve of Receiver Operator Characteristic curves By Group and System

| Group | System | Area | SE | p | 95% CI of Area |
|---|---|---|---|---|---|
| $G_T$ | Scheuer** | 0.863 | 0.0212 | <0.0001 | 0.822 to 0.905 |
| $G_V$ | Scheuer** | 0.804 | 0.0235 | <0.0001 | 0.758 to 0.851 |
| $G_T$ | Ishak* | 0.860 | 0.0211 | <0.0001 | 0.818 to 0.901 |
| $G_V$ | Ishak* | 0.804 | 0.0234 | <0.0001 | 0.758 to 0.850 |

TABLE 10 (b)

Performance in Subgroups

| Group | System | Area | SE | p | 95% CI of Area |
|---|---|---|---|---|---|
| Hepatitis C $G_V$ | Scheuer** | 0.773 | 0.0386 | <0.0001 | 0.697 to 0.848 |
| Hepatitis C $G_V$ | Ishak* | 0.842 | 0.0391 | <0.0001 | 0.765 to 0.919 |
| NAFLD $G_V$ | Scheuer** | 0.870 | 0.1040 | 0.0002 | 0.666 to 1.000 |
| NAFLD $G_V$ | Ishak* | 0.931 | 0.0373 | <0.0001 | 0.858 to 1.000 |
| Alcohol $G_V$ | Scheuer** | 0.944 | 0.0555 | <0.0001 | 0.836 to 1.000 |
| Alcohol $G_V$ | Ishak* | 0.923 | 0.0671 | <0.0001 | 0.792 to 1.000 |

*Bifurcated (0, 1, 2, 3):(4, 5, 6)
**Bifurcated (0, 1, 2):(3, 4)

Using the Scheuer staging system, for Hepatitis C AUC=0.773; SE=0.0386; p<0.0001; 0.697 to 0.848; for NAFLD AUC=0.870; SE=0.104; p<0.0002; 95% CI=0.666 to 1.000; for Alcoholic liver disease (ALD) AUC=0.944; SE=0.0555; p<0.0001; 95% CI=0.836 to 1.000.

Tables 11a and 11b demonstrate specific coordinates for the validation ($G_V$) curves at different score thresholds for both the Ishak (11a) Scheuer (11b) systems.

TABLE 11(a)

Specific Coordinates of the ROC Curve in Gv Ishak Scoring System - Algorithm: Pathologist A

| Score | Sensitivity | Specificity | Positive Predictive Power | Negative Predictive Power |
|---|---|---|---|---|
| 0.066 | 95% | 25% | 31% | 93% |
| 0.102 | 90% | 41% | 35% | 92% |
| 0.130 | 85% | 52% | 39% | 91% |
| 0.178 | 80% | 66% | 46% | 90% |
| 0.241 | 69% | 80% | 56% | 88% |
| 0.285 | 63% | 85% | 60% | 86% |
| 0.364 | 53% | 90% | 66% | 84% |
| 0.468 | 44% | 95% | 76% | 83% |
| 0.820 | 19% | 99% | 90% | 77% |
| Performance of algorithm relative to Pathologists B and C | | | | |
| $0.102^B$ | 87.9% | 42.8% | 37.2% | 90.2% |
| $0.102^C$ | 89.3% | 42.2% | 34.2% | 92.2% |

TABLE 11(b)

Specific Coordinates of the ROC Curve in $G_v$ Scheuer Scoring System - Algorithm: Pathologist A

| Score | Sensitivity | Specificity | Positive Predictive Power | Negative Predictive Power |
|---|---|---|---|---|
| 0.063 | 95% | 24% | 31% | 93% |
| 0.102 | 90% | 41% | 35% | 92% |
| 0.130 | 85% | 53% | 40% | 91% |
| 0.179 | 80% | 67% | 46% | 90% |
| 0.238 | 69% | 80% | 55% | 88% |
| 0.273 | 64% | 85% | 60% | 87% |
| 0.358 | 54% | 90% | 65% | 84% |
| 0.457 | 47% | 95% | 75% | 83% |
| 0.507 | 44% | 96% | 80% | 83% |
| 0.826 | 19% | 99% | 90% | 77% |
| Performance of algorithm relative to Pathologists B and C | | | | |
| $0.102^B$ | 86.7% | 51.2% | 40.7% | 90.9% |
| $0.102^C$ | 86.5% | 49.5% | 36.2% | 91.7% |

The specific coordinates for the ROC curve for the Gv cohort are shown in the table. Sensitivity, specificity, positive predictive value and negative predictive value have been calculated for a range of algorithm threshold scores. In addition performance characteristics are presented for the algorithm compared to the staging assigned by pathologists B and C using an algorithm threshold score of 0.102, the score that gave a sensitivity of 90% in detection of significant fibrosis in the series staged by pathologist A. Data are presented for comparison with the Ishak staging (12a) and Scheuer staging (12b).

In addition to sensitivity and specificity, positive and negative predictive values are shown. The sensitivity for the detection of Scheuer Stage 3 or 4 fibrosis is 90% at a threshold algorithm score of 0.102 yielding a NPV=92%. Specificity is 99% at a threshold score of 0.82 yielding a PPV=90%. The corresponding values for Ishak Stages 4–6 are 90% and 92% at a threshold of 0.102.

The performance of the algorithm was evaluated by comparison with the biopsy stages assigned by the other two pathologists using a threshold score of 0.102. The sensitivity for the detection of Scheuer stage 3 or 4 fibrosis is 86.7% for B and 86.5% for C at a threshold algorithm score of 0.102 yielding NPV=90.9% and 91.7% respectively. Using a threshold algorithm score of 0.102 the corresponding values for Ishak stages 4–6 for B are sensitivity=87.9%; NPV=90.2% and for C sensitivity=89.3%; NPV=92.2%.

Results for the performance of the algorithm in the three most prevalent chronic liver diseases represented in the $G_V$ cohort staged by Pathologist A, chronic hepatitis C (CHC), Non-alcoholic fatty liver disease (NAFLD) and alcoholic liver disease (ALD) are shown in Tables 12a and 12b. These tables present the ROC coordinates, sensitivity, specificity and negative and positive predictive values for algorithm score thresholds yielding results exceeding 90%.

TABLE 12a

Sensitivity and Specificity in $G_V$ Patients
Scheuer Staging

| Disease | Score | Sensitivity | Specificity | PPV | NPV |
|---|---|---|---|---|---|
| Hepatitis C | 0.063 | 95% | 29% | 27.7% | 94.9% |
| | 0.067 | 90% | 31% | 27.5% | 92.3% |
| | 0.090 | 85% | 43% | 29.9% | 91.1% |
| | 0.126 | 80% | 58% | 35.2% | 91.0% |
| | 0.190 | 63% | 80% | 47.9% | 88.5% |
| | 0.219 | 52% | 85% | 50.0% | 86.2% |
| | 0.268 | 47% | 90% | 57.8% | 85.6% |
| | 0.426 | 38% | 95% | 70.0% | 84.3% |
| | 0.564 | 30% | 99% | 89.5% | 83.3% |
| NAFLD | 0.375 | 89% | 96% | 80% | 98% |
| | 0.462 | 78% | 98% | 87% | 96% |
| ALD | 0.087 | 100.0% | 16.7% | 75.0% | 100.0% |
| | 0.431 | 93.3% | 100.0% | 100.0% | 85.7% |

TABLE 12b

Ishak Staging

| Disease | Score | Sensitivity | Specificity | PPV | NPV |
|---|---|---|---|---|---|
| Hepatitis C | 0.065 | 100% | 28% | 19.2% | 100.0% |
| | 0.067 | 95% | 29% | 18.5% | 96.8% |
| | 0.076 | 91% | 33% | 19.0% | 95.9% |
| | 0.130 | 86% | 56% | 25.2% | 96.0% |
| | 0.177 | 80% | 72% | 32.9% | 95.6% |
| | 0.196 | 77% | 80% | 40.0% | 95.5% |
| | 0.230 | 69% | 85% | 44.6% | 94.2% |
| | 0.286 | 61% | 90% | 51.2% | 93.1% |
| | 0.418 | 50% | 95% | 62.1% | 91.7% |
| | 0.710 | 30% | 99% | 84.6% | 89.3% |
| NAFLD | 0.381 | 100% | 88% | 40% | 100% |
| | 0.462 | 75% | 90% | 37% | 98% |
| | 0.855 | 25% | 98% | 49% | 94% |
| ALD | 0.092 | 100.0% | 12.5% | 83.8% | 100.0% |
| | 0.447 | 92.3% | 87.5% | 97.1% | 71.5% |
| | 0.621 | 84.6% | 100.0% | 100.0% | 59.0% |

The specific coordinates for the ROC curve for the GV cohort are shown in the table. Sensitivity, specificity, positive predictive value and negative predictive value have been calculated for a range of algorithm scores. Data are presented for comparison with the Scheuer staging (12a) and Ishak staging (12b). In each case the table (a) refers to Scheuer staging and (b) to Ishak staging. At a threshold value of 0.065, for Ishak fibrosis stage 4–6, the Sensitivity-100%, Negative Predictive Value=100%.

For NAFLD comparison to the Scheuer system, for fibrosis stage 3 or 4, using an algorithm score threshold value of 0.375 the sensitivity-89%, specificity-96%, PPV=80% and NPV=98%. In alcoholic liver disease, for detecting Scheuer fibrosis stage 3 or 4, using a threshold score of 0.087 the sensitivity=100% and NPV=100%, while a threshold of 0.431 yields a sensitivity=93.3%, specificity=100%, PPV=100% and NPV=85.7%.

By convention clinicians and pathologists differentiate three categories of liver fibrosis as "mild", "moderate" and "severe" fibrosis corresponding to Scheuer stages 0,1; 2,3 and 4. The transition from mild to moderate fibrosis is frequently recognized as a significant step in disease progression, reflecting a milestone that has significance for prognosis and influencing decisions on patient management. Accordingly the data were analyzed using bifurcation between Scheuer stages 0,1 and 2,3,4 rather than the bifurcation based on the distribution of algorithm discriminant scores between stages 0,1,2 and 3,4.

The results reveal a comparable level of performance. Results yielding 90% sensitivity for the detection of moderate/severe fibrosis are shown in Table 13 below for bifurcation between Scheuer stages 0,1:2,3,4 (A) and 0,1,2:3,4 (B). The data were also analyzed for the ability to detect stage 4 fibrosis (cirrhosis) with 90% sensitivity (C).

TABLE 13

| Scheuer Score | AUC | SE | P | 95% CI of Area | DST | Sensitivity | Specificity |
|---|---|---|---|---|---|---|---|
| A = 0, 1 v 2, 3, 4 | 0.782 | 0.0213 | <0.0001 | 0.740 to 0.823 | −0.864 | 90.3% | 29.6% |
| B = 0, 1, 2 v 3, 4 | 0.804 | 0.0236 | <0.0001 | 0.757 to 0.850 | −0.671 | 90.5% | 37.5% |
| C = 0, 1, 2, 3 v 4 | 0.887 | 0.0256 | <0.0001 | 0.837 to 0.937 | 0.025 | 90.7% | 69.2% |

The data in Table 13 represent the performance of the algorithm in detecting bifurcated outcomes (A=0,1: 2-4 B=0,1,2: 3,4 and C=0,1,2,3:4 for the Scheuer system) for the 400 Test ($G_T$) and 521 Validation ($G_V$) samples from the whole cohort of patients with diverse chronic liver diseases. The results presented include area under the curve (AUC) of receiver operator characteristic curves, associated standard errors and p values with 95% confidence intervals. The sensitivity and specificity for the detection of fibrosis are presented for specific Discriminant Score Threshold values (DST). "A" represents the bifurcation conventionally used to differentiate mild from moderate and severe liver fibrosis. "B" is the bifurcation suggested representing the differentiation between mild and moderate fibrosis derived from analysis of the distribution of scores in the cohort. "C" represents the differentiation between severe fibrosis/cirrhosis and mild/moderate fibrosis.

(d) Conclusions

Analyses of the ELF study verified that embodiments of the invention which combine serum markers of liver fibrosis can be used to identify significant liver fibrosis in patients with a range of chronic liver diseases with a sensitivity of 90%. The invention provided a similar level of sensitivity when compared to the scoring of three different pathologists, illustrating that it can be employed with similar accuracy in different settings.

Embodiments of the invention have been validated by assessing levels of agreement between expert pathologists, agreement with image analysis, the performance of individual markers of fibrosis, and the performance of the invention in diagnosing a range of chronic liver diseases, including the three of the most common conditions encountered in our clinical practice.

The cohort of patients tested included patients suffering from a wide range of chronic liver diseases. The performance of embodiments of the invention in evaluating this cohort indicates that it can be used to identify patients with significant degrees of fibrosis in a wide range of liver disorders. The change in sensitivity and specificity with changes in the threshold score of the algorithm reveals that the invention can be used with a high degree of accuracy to detect either the presence or absence of significant liver fibrosis depending on the test threshold employed.

Furthermore, the instant results indicate that the invention is useful in monitoring therapeutic interventions directed at preventing fibrosis in patients with progressive chronic liver diseases. Recognition that liver fibrosis is a reversible process has lead to considerable interest in the development of anti-fibrotic therapies. The evaluation of anti-fibrotic drugs will depend upon the use of diagnostic tests that will allow investigators to determine their efficacy. Repeated and frequent use of liver biopsies is neither ethical nor practical; biopsies are also subject to sampling error and variability in interpretation. The invention provides a more practical and acceptable alternative to evaluate changes in histological stage as outcome measures used in the evaluation of new anti-fibrotic therapies.

In addition, we have shown that embodiments of the invention are useful in monitoring disease progression or response to alterations in life-style, such as reduction in alcohol intake, hepatitis C or alcoholic liver disease, and weight loss in NAFLD and hepatitis C.

The aforementioned results show that embodiments of the invention performed particularly well in diagnosis of the status and progress of hepatitis C, NAFLD and alcoholic liver disease, the three most common conditions encountered in clinical hepatology practice. In each of these conditions, by selecting an appropriate test threshold, a PPV or NPV exceeding 90% can be attained, indicating that the invention will be of considerable use in clinical practice to either confirm or refute the presence of significant fibrosis in patients with these disorders.

Recent studies in hepatitis C have reported similar levels of performance for indices combining readily available biochemistry and haematology tests. Forns, et al., *Hepatology* 2002; 36:986-992; Wai, et al., *Hepatology* 38, 518-526. 2003. These studies made assumptions about the point at which fibrosis became significant and employed bivariate logistic regression to derive algorithms, rather than deriving the step-point in fibrosis from analysis of the data in the test sets.

In diagnosing the status or progression of hepatitis C, the invention could be used to determine the potential benefit and timing of anti-viral therapy. Our analyses indicate that in patients with non-alcoholic fatty liver disease, the invention could be used to differentiate the minority of patients at risk of significant fibrosis from the majority who have relatively benign steatosis without significant fibrosis (32A).

In patients with alcoholic liver disease, our results show that embodiments of the invention performed at the highest level, attaining sensitivities and specificity of 100%.

These data indicate that embodiments of the invention could be used both to identify those patients at risk of significant fibrosis and to identify the majority of patients with alcoholic liver disease that have little hepatic fibrosis.

Citations:
1. Friedman SL
   The cellular basis of hepatic fibrosis: Mechanism and treatment strategies.
   N Engl J Med 1993; 328: 1828-1835
2. Friedman SL
   Molecular mechanism of hepatic fibrosis and principle of therapy
   J Gastroenterol 1997; 32: 424-430
3. Hayasaka A, Saisho H
   Serum markers as tools to monitor liver fibrosis
   Digestion 1998; 59: 381-384
4. Schuppan D, Stolzel U, Oesterling C, Somasundaram R
   Serum assays for liver fibrosis.
   J Hepatol 1995; 22 (Suppl 2): 82-88
5. Murawaki Y, Ikuta Y, Nishimura Y, Koda M, Kawasaki H
   Serum markers for connective tissue turnover in patients with chronic hepatitis C; A comparative analysis.
   J Hepatol 1995; 23: 145-152
6. Wong V S, Hughes V, Trull A, Wight D G D, Petrik J, Alexander G J M Serum hyaluronic acid is a useful marker of liver fibrosis in chronic hepatitis C virus infection
   J Viral Hepatitis 1998; 5: 187-192
7. Poynard T, Aubert A, Bedossa P, Abella A, Naveau S, Paraf F, Chapu J C
   A simple biological index for detection of alcoholic liver disease in drinkers Gastroenterology 1991; 100: 1397-1402
8. Naveau S, Poynard T, Benattat C, Bedossa P, Chaput J C
   Alpha-2 macroglobulin and hepatic fibrosis:diagnostic interest Dig Dis Sci 1994; 11: 2426-2432
9. Oberti F, Valsesia E, Pilette C, Rousselet M C, Bedossa P, Aube C, Gallois Y, Rifflet
   H, Maiga M Y, Penneau-Fontbonne D, Cales P
   Noninvasive diagnosis of hepatic fibrosis and cirrhosis Gastroenterology 1997; 113: 1609-1616
10. Teare J P, Sherman D, Greenfield S M, Simpson J, Catterall A P, Murray-Lyon I M, Peters T J, Williams R, Thompson R P H
    The Lancet 1993; 342: 895-898
11. Imbert-Bismut F, Ratziu V, Pieroni L, Charlotte F, Benhamou Y, Poynard T, Lancet 2001; 357: 1069-75.

Citations Related to the ELF Study:
1A. Desmet V, Fevery J. Liver biopsy. Baillieres Clin Gastroenterol 1995; 9:811-828.
2A. Scheuer P J. Chronic hepatitis: what is activity and how should it be assessed? Histopathology 1997; 30:103-105.
3A. Pasha T, Gabriel S, Themeau T, Dickson E R, Lindor K D. Cost-effectiveness of ultrasound-guided liver biopsy. Hepatology 1998; 27:1220-1226.
4A. Gilmore I T, Burroughs A, Murray-Lyon I M, Williams R, Jenkins D, Hopkins A. Indications, methods, and outcomes of percutaneous liver biopsy in England and Wales: an audit by the British Society of Gastroenterology and the Royal College of Physicians of London. Gut 1995; 36:437-441.
5A. McGill D B, Rakela J, Zinsmeister A R, Ott B J. A 21-year experience with major hemorrhage after percutaneous liver biopsy. Gastroenterology 1990; 99:1396-1400.
6A. Sherlock S, Dooley J. Diseases of the liver and biliary system. 10 ed. London: Blackwell Scientific, 1997.
7A. Regev A, Berho M, Jeffers L J, Milikowski C, Molina E G, Pyrsopoulos N T, Feng Z Z, Reddy K R, Schiff E R. Sampling error and intraobserver variation in liver biopsy in patients with chronic HCV infection. American Journal of Gastroenterology 2002; 97:2614-2618.

8A. Theodossi A, Skene A M, Portmann B, Knill-Jones R P, Patrick R S, Tate R A, Kealey W, Jarvis K J, O'Brian D J, Williams R. Observer variation in assessment of liver biopsies including analysis by kappa statistics. Gastroenterology 1980; 79:232-241.

9A. Scheuer P J, Lefkowitch J H. Liver biopsy interpretation. 6 ed. London: W. B. Saunders, 2002.

10A. Yamauchi M, Mizuhara Y, Maezawa Y, Toda G. Serum tenascin levels in chronic liver disease. Liver 1994; 14:148-153.

11A. McHutchison J G, Blatt L M, de Medina M, Craig J R, Conrad A, Schiff E R, Tong M J. Measurement of serum hyaluronic acid in patients with chronic hepatitis C and its relationship to liver histology. Consensus Interferon Study Group. Journal of Gastroenterology & Hepatology 2000; 15:945-951.

12A. Hayasaka A, Schuppan D, Ohnishi K, Okuda K, Hahn E G. Serum concentrations of the carboxyterminal cross-linking domain of procollagen type IV (NC1) and the aminoterminal propeptide of procollagen type III (PIIIP) in chronic liver disease. J Hepatol 1990; 10:17-22.

13A. Schuppan D, Cantaluppi M C, Becker J, Veit A, Bunte T, Troyer D, Schuppan F, Schmid M, Ackermann R, Hahn E G. Undulin, an extracellular matrix glycoprotein associated with collagen fibrils. J Biol Chem 1990; 265:8823-8832.

14A. Murawaki Y, Ikuta Y, Koda M, Kawasaki H. Serum type III procollagen peptide, type IV collagen 7S domain, central triple-helix of type IV collagen and tissue inhibitor of metalloproteinases in patients with chronic viral liver disease: relationship to liver histology. Hepatology 1994; 20:780-787.

15A. Kasahara A, Hayashi N, Mochizuki K, Oshita M, Katayama K, Kato M, Masuzawa M, Yoshihara H, Naito M, Miyamoto T, Inoue A, Asai A, Hijioka T, Fusamoto H, Kamada T. Circulating matrix metalloproteinase-2 and tissue inhibitor of metalloproteinase-1 as serum markers of fibrosis in patients with chronic hepatitis C. Relationship to interferon response. J Hepatol 1997; 26:574-583.

16A. Murawaki Y, Ikuta Y, Okamoto K, Koda M, Kawasaki H. Serum matrix metalloproteinase-3 (stromelysin-1) concentration in patients with chronic liver disease. J Hepatol 1999; 31:474-481.

17A. Trinchet J C. Clinical use of serum markers of fibrosis in chronic hepatitis. J Hepatol 1995; 22:89-95.

18A. Imbert-Bismut F, Ratziu V, Pieroni L, Charlotte F, Benhamou Y, Poynard T.
Biochemical markers of liver fibrosis in patients with hepatitis C virus infection: a prospective study. Lancet 2001; 357: 1069-1075.

19A. Castera L, Hartmann D J, Chapel F, Guettier C, Mall F, Lons T, Richardet J P, Grimbert S, Morassi O, Beaugrand M, Trinchet J C. Serum laminin and type IV collagen are accurate markers of histologically severe alcoholic hepatitis in patients with cirrhosis. J Hepatol 2000; 32:412-418.

20A. Pilette C, Rousselet M C, Bedossa P, Chappard D, Oberti F, Rifflet H, Maiga M Y, Gallois Y, Cales P. Histopathological evaluation of liver fibrosis: quantitative image analysis vs semi-quantitative scores. Comparison with serum markers. Journal of Hepatology 1998; 28:439-446.

21A. Guechot J, Laudat A, Loria A, Serfaty L, Poupon R, Giboudeau J. Diagnostic accuracy of hyaluronan and type III procollagen amino-terminal peptide serum assays as markers of liver fibrosis in chronic viral hepatitis C evaluated by ROC curve analysis. Clin Chem 1996; 42:558-563.

22A. Murawaki Y, Ikuta Y, Koda M, Nishimura Y, Kawasaki H. Clinical significance of serum hyaluronan in patients with chronic viral liver disease. J Gastroenterol Hepatol 1996; 11:459-465.

23A. Johansen J S, Christoffersen P, Moller S, Price P A, Henriksen J H, Garbarsch C, Bendtsen F. Serum YKL-40 is increased in patients with hepatic fibrosis. J Hepatol 2000; 32:911-920.

24A. Nojgaard C, Johansen J S, Krarup H B, Holten-Andersen M, Moller A, Bendtsen F, Danish Viral Hepatitis Study Group. Effect of antiviral therapy on markers of fibrogenesis in patients with chronic hepatitis C. Scandinavian Journal of Gastroenterology 2003; 38:659-665.

25A. Patel K, Lajoie A, Heaton S, Pianko S, Behling C A, Bylund D, Pockros P J, Blatt L M, Conrad A, McHutchison J G. Clinical use of hyaluronic acid as a predictor of fibrosis change in hepatitis C. Journal of Gastroenterology & Hepatology 2003; 18:253-257.

26A. Myers R P, Benhamou Y, Imbert-Bismut F, Thibault V, Bochet M, Charlotte F, Ratziu V, Bricaire F, Katlama C, Poynard T. Serum biochemical markers accurately predict liver fibrosis in HIV and hepatitis C virus co-infected patients. AIDS 2003; 17:721-725.

27A. Scheuer P J. Classification of chronic viral hepatitis: a need for reassessment. J Hepatol 1991; 13:372-374.

28A. Ishak K, Baptista A, Bianchi L, Callea F, De Groote J, Gudat F, Denk H, Desmet V, Korb G, MacSween R N, et al. Histological grading and staging of chronic hepatitis. J Hepatol 1995; 22:696-699.

29A. Bedossa P, Poynard T, Naveau S, Martin E D, Agostini H, Chaput J C. Observer variation in assessment of liver biopsies of alcoholic patients. Alcohol Clin Exp Res 1988; 12:173-178.

30A. Arthur M J. Reversibility of liver fibrosis and cirrhosis following treatment for hepatitis C. Gastroenterology 2002; 122:1525-1528.

31A. Rosenberg W M. Rating fibrosis progression in chronic liver diseases. Journal of Hepatology 2003; 38:357-360.

32A. Teli M R, James O F, Burt A D, Bennett M K, Day C P. The natural history of nonalcoholic fatty liver: a follow-up study. Hepatology 1995; 22:1714-1719.

33A. Lichtinghagen R, Huegel O, Seifert T, Haberkorn C I, Michels D, Flemming P, Bahr M, Boeker K H. Expression of matrix metalloproteinase-2 and -9 and their inhibitors in peripheral blood cells of patients with chronic hepatitis C. Clin Chem 2000; 46:183-192.

34A. Tran A, Benzaken S, Saint-Paul M C, Guzman-Granier E, Hastier P, Pradier C, Barjoan E M, Demuth N, Longo F, Rampal P. Chondrex (YKL-40), a potential new serum fibrosis marker in patients with alcoholic liver disease. Eur J Gastroenterol Hepatol 2000; 12:989-993.

35A. Guyader D, Jacquelinet C, Moirand R, Turlin B, Mendler M H, Chaperon J, David V, Brissot P, Adams P, Deugnier Y. Noninvasive prediction of fibrosis in C282Y homozygous hemochromatosis. Gastroenterology 1998; 115:929-936.

36A. Beaton M, Guyader D, Deugnier Y, Moirand R, Chakrabarti S, Adams P. Noninvasive prediction of cirrhosis in C282Y-linked hemochromatosis. Hepatology 2002; 36:673-678.

Publications cited: Expression of Polynucleotides and Hybridoma Development Protocol:

(1) Sambrook et al., MOLECULAR CLONING: A LABORATORY MANUAL, 2d ed., (1989)

(2) Ausubel et al., CURRENT PROTOCOLS IN MOLECULAR BIOLOGY, John Wiley & Sons, New York, N.Y., (1989).

(3) Van Heeke & Schuster, J. Biol. Chem. 264, 5503-5509, (1989)
(4) Grant et al., Methods Enzymol. 153, 516-544, (1987)
(5) Takamatsu, EMBO J. 6, 307-311, (1987)
(6) Coruzzi et al., EMBO J. 3, 1671-1680, (1984)
(7) Broglie et al., Science 224, 838-843, (1984)
(8) Winter et al., Results Probl. Cell Differ. 17, 85-105, (1991)
(9) McGraw Hill Yearbook of Science and Technology, McGraw Hill, New York, N.Y., pp. 191-196, (1992)
(10) Engelhard et al., Proc. Nat. Acad. Sci. 91, 3224-3227, (1994)
(11) Logan & Shenk, Proc. Natl. Acad. Sci. 81, 3655-3659, (1984)
(12) Scharf et al., Results Probl. Cell Differ. 20, 125-162, (1994)
(13) Freshney R.I., ed., Animal Cell Culture, (1986)
(14) Wigler et al., Cell 11, 223-232, (1977)
(15) Lowy et al., Cell 22, 817-823, (1980)
(16) Wigler et al., Proc. Natl. Acad. Sci. 77, 3567-3570, (1980)
(17) Colbere-Garapin et al., J. Mol. Biol. 150, 114, (1981)
(18) Hartman & Mulligan, Proc. Natl. Acad. Sci. 85, 8047-8051, (1988)
(19) Rhodes et al., Methods Mol. Biol. 55, 121-131, (1995)
(20) Hampton et al., Serological Methods: A Laboratory Manual, APS Press, St. Paul, Minn., (1990)
(21) Maddox et al., J. Exp. Med. 158, 1211-1216, (1983)
(22) Porath et al., Prot. Exp. Purif. 3, 263-281, (1992)
(23) Kroll et al., DNA Cell Biol. 12, 441-453, (1993)
(24) Caruthers et al., Nucl. Acids Res. Symp. Ser. 215-223, (1980)
(25) Horn et al. Nucl. Acids Res. Symp. Ser. 225-232, (1980)
(26) Merrifield, J. Am. Chem. Soc. 85, 2149-2154, (1963)
(27) Roberge et al., Science 269, 202-204, (1995)
(28) Creighton, Proteins: Structures and Molecular Principles, WH and Co., New York, N.Y., (1983)

What is claimed is:

1. A method for aiding in the diagnosis of liver fibrosis comprising:
   (a) obtaining a sample of body fluid from an individual;
   (b) selecting two or more diagnostic markers of a dynamic process of extracellular matrix synthesis and/or extracellular matrix degradation from said sample;
   (c) measuring the amount of each said selected two or more diagnostic markers in said sample to obtain a measured value for each of said selected diagnostic markers; and
   (d) combining said measured value of each said selected diagnostic markers using a mathematical algorithm to obtain a liver fibrosis score.

2. The method according to claim 1 wherein said sample of body fluid is blood, serum, plasma or urine.

3. The method according to claim 1 wherein said liver fibrosis score is used to support, predict or substitute the histological score of a liver biopsy.

4. The method according to claim 1 wherein said mathematical algorithm is a discriminant function algorithm.

5. The method according to claim 4 wherein said discriminant function algorithm is a linear discriminant function algorithm.

6. The method according to claim 4 wherein said liver fibrosis score corresponds to a pathology score obtained by a histological assessment of a liver biopsy.

7. The method according to claim 6 wherein said pathology score is obtained by using any one of the following scoring systems: the Scheuer scoring system, the Ishak scoring system, the HAI scoring system, the Ludwig scoring system, or the Metavir scoring system.

8. The method according to claim 1 wherein said liver fibrosis score is at least one factor to determine a treatment strategy for said individual.

9. The method according to claim 1 wherein said liver fibrosis score is at least one factor used to monitor the efficacy of an implemented treatment strategy for said individual.

10. The method according to claim 1 wherein said liver fibrosis score is at leas one factor used to determine whether said individual should obtain a liver biopsy.

11. The method according to claim 1 wherein said liver fibrosis score is at least one factor used to distinguish liver fibrosis from liver cirrhosis.

12. The method according to claim 1 wherein said liver fibrosis score is at least one factor used to evaluate the degree of liver fibrosis in said individual.

13. The method according to claim 1 wherein at least one of said two or more selected diagnostic markers is Hyaluronan.

14. The method according to claim 1 wherein at least one of said two or more selected diagnostic markers is PIIINP.

15. The method according to claim 1 wherein at least one of said two or more selected diagnostic markers is TIMP-1.

16. The method according to claim 2 wherein said body fluid is blood, serum, plasma or urine.

17. The method according to claim 3 wherein said liver fibrosis score is at least one factor used to determine a treatment strategy for said individual.

18. The method according to claim 1 wherein said liver fibrosis score is at least one factor used to monitor the efficacy of an implemented treatment strategy for said individual.

19. The method according to claim 1, wherein said liver fibrosis score is measured at two or more time points.

* * * * *

UNITED STATES PATENT AND TRADEMARK OFFICE
CERTIFICATE OF CORRECTION

PATENT NO. : 7,668,661 B2  Page 1 of 1
APPLICATION NO. : 10/868437
DATED : February 23, 2010
INVENTOR(S) : Volker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1009 days.

Signed and Sealed this

Twenty-eighth Day of December, 2010

David J. Kappos
*Director of the United States Patent and Trademark Office*